US007364876B2

(12) United States Patent
Takai et al.

(10) Patent No.: US 7,364,876 B2
(45) Date of Patent: Apr. 29, 2008

(54) ADIP PROTEIN AND USE THEREOF

(75) Inventors: Yoshimi Takai, Hyogo (JP); Kenji Irie, Osaka (JP); Masanori Asada, Miyagi (JP)

(73) Assignee: EISAI R & D Management Co., Ltd., Tokyo (JP)

( * ) Notice: Subject to any disclaimer, the term of this patent is extended or adjusted under 35 U.S.C. 154(b) by 406 days.

(21) Appl. No.: 10/644,084

(22) Filed: Aug. 20, 2003

(65) Prior Publication Data

US 2006/0160092 A1    Jul. 20, 2006

(30) Foreign Application Priority Data

Sep. 27, 2002    (JP) ............................. 2002-284263

(51) Int. Cl.
*C07H 21/04* (2006.01)
*C12N 15/00* (2006.01)
*C12N 15/63* (2006.01)
*C12N 15/12* (2006.01)
*C07K 14/00* (2006.01)

(52) U.S. Cl. .................. 435/69.1; 435/235.1; 435/325; 435/320.1; 536/23.1; 536/23.5; 530/350

(58) Field of Classification Search ...................... None
See application file for complete search history.

(56) References Cited

U.S. PATENT DOCUMENTS 5,739,008 A * 4/1998 Hayashi et al. ............ 435/69.1
6,180,760 B1 * 1/2001 Takai et al. ................. 530/350
6,943,241 B2 * 9/2005 Isogai et al. ............... 536/23.1

OTHER PUBLICATIONS

Mammalian Gene Collection (MGC) Program team, PNAS, vol. 99, pp. 16899-16903, Dec. 24, 2002.*
Carninci et al. Genome Resaerch, vol. 10, pp. 1617-1630, 2000.*
The RIKEN Genome Exploration Research group Phase II Team and the FANTOM Consortium, Nature, vol. 409, pp. 685-690, Feb. 8, 2001.*
Aoki, J., et al., "Mouse Homolog of Poliovirus Receptor-Related Gene 2 Product, mPRR2, Mediates Homophilic Cell Aggregation," *Exp. Cell. Res.* 235:374-384, Academic Press (1997).
Aoki, J., et al., "Amino Acid Residues on Human Poliovirus Receptor Involved in Interaction with Poliovirus," *J. Biol. Chem.* 269:8431-8438, The American Society for Biochemistry and Molecular Biology, Inc. (1994).
Bazzoni, G., et al., "Interaction of Junctional Adhesion Molecule with the Tight Junction Components ZO-1, Cingulin, and Occludin," *J. Biol. Chem.* 275:20520-20526, The American Society for Biochemistry and Molecular Biology, Inc. (2000).
Böhl, F., et al., "She2p, a novel RNA-binding protein tethers *ASH1* mRNA to the Myo4p myosin via She3p," *EMBO J.* 19:5514-5524, European Molecular Biology Organization (2000).
Cocchi, F., et al., "The V domain of herpesvirus lg-like receptor (HlgR) conatins a major functional region in herpes simplex virus-1 entry into cells and interacts physically with the viral glycoprotein D," *Proc. Natl. Acad. Sci. USA* 95:15700-15705, The National Academy of Sciences (1998).
Cocchi, F., et al., "Cell-to-Cell Spread of Wild-Type Herpes Simplex Virus Type 1, but Not of Syncytial Strains, is Mediated by the Immunoglobulin-Like Receptors That Mediate Virion entry, Nectin 1 (PRR1/HveC/HlgR) and Nectin2 (PRR2/HveB)," *J. Virol.* 74:3909-3917, American Society for Microbiology (2000).
Eberlé, F., et al., "The human *PRR2* gene, related to the human poliovirus receptor gene (*PVR*), is the true homolog of the murine *MPH* gene," Gene 159:267-272, Elsevier Science B.V. (1995).
Ebnet, K., et al., "Junctional Adhesion Molecule Interacts with the PDZ Domain-containing Proteins AF-6 and ZO-1," *J. Biol. Chem.* 275:27979-27988, The American Society for Biochemistry and Molecular Biology, Inc. (2000).
Farquhar, M.G. and Palade, G.E., "Junctional Complexes in Various Epithelia," *J. Cell. Biol.* 17:375-412, The Rockefeller University Press (1963).
Fukuhara, A., et al., "Involvement of nectin in the localization of junctional adhesion molecule at tight junctions," *Oncogene* 21:7642-7655, Nature Publishing Group (Oct. 2002).
Fukuhara, A., et al., "Role of nectin in organization of tight junctions in epithelial cells," *Genes Cells* 7:1059-1072, Blackwell Science Limited (Oct. 2002).
Furuse, M., et al., "A Single Gene Product, Claudin-1 or -2, Reconstitutes Tight Junction Strands and Recruits Occludin in Fibroblasts," *J. Cell. Biol.* 143:391-401, The Rockefeller University Press (1998).
Fururse, M., et al., "Claudin-1 and -2: Novel Integral Membrane Proteins Localizing at Tight Junctions with No Sequence Similarity to Occludin," *J. Cell Biol.* 141:1539-1550, The Rockefeller University Press (1998).
Furuse, M., et al., "Direct Association of Occludin with ZO-1 and Its Possible Involvement in the Localization of Occludin at Tight Junctions," *J. Cell. Biol.* 127:1617-1626, The Rockefeller University Press (1994).
Geraghty, R.J., et al., "Entry of Alphaherpesviruses Mediated by Poliovirus Receptor-Related Protein 1 and Poliovirus Receptor," *Science* 280:1618-1620, American Association for the Advancement of Science (1998).
Gumbiner, B.M., "Cell Adhesion: The Molecular Basis of Tissue Architecture and Morphogenesis," *Cell* 84:345-357, Cell Press (1996).
Haskins, J., et al., "ZO-3, a Novel Member of the MAGUK Protein Family Found at the Tight Junction, Interacts with ZO-1 and Occludin," *J. Cell Biol.* 141:199-208, The Rockefeller University Press (1998).

(Continued)

*Primary Examiner*—Christine J. Saoud
*Assistant Examiner*—Nirmal S. Basi
(74) *Attorney, Agent, or Firm*—Sterne, Kessler, Goldstein & Fox, P.L.L.C.

(57) ABSTRACT

The objective of the present invention is to provide a gene encoding novel afadin DIL domain-binding protein (ADIP) and use of the novel ADIP protein.

The present inventors successfully identified a novel afadin-binding protein (ADIP) using yeast two-hybrid screening in order to identify how the nectin and afadin system organize tight junctions and adherens junctions at the cell-cell junctions. The novel protein is useful for evaluating actin cytoskeleton-controlling agents.

6 Claims, 10 Drawing Sheets

OTHER PUBLICATIONS

Ikeda, W., et al., "Afadin: A Key Molecule Essential for Structural Organization of Cell-Cell Junctions of Polarized Epithelia during Embryogenesis," *J. Cell. Biol.* 146:1117-1131, The Rockefeller University Press (1999).

Imamura, Y., et al., "Functional Domains of α-Catenin Required for the Strong State of Cadherin-based Cell Adhesion," *J. Cell Biol.* 144:1311-1322, The Rockefeller University Press (1999).

Itoh, M., et al., "The 220-kD Protein Colocalizing with Cadherins in Non-Epthelial Cells Is Identical to ZO-1, a Tight Junction-associated Protein in epithelial Cells: cDNA Cloning and Immunoelectron Microscopy," *J. Cell. Biol..* 121:491-502, The Rockefeller University Press (1993).

Itoh, M., et al., "Involvement of ZO-1 in Cadherin-based Cell Adhesion through Its Direct Binding to α Catenin and Actin Filaments," *J. Cell Biol.* 138:181-192, The Rockefeller University Press (1997).

Itoh, M., et al., "Characterization of ZO-2 as a MAGUK Family Member Associated with Tight as well as Adherens Junctions with a Binding Affinity to Occludin and α Catenin," *J. Biol. Chem.* 274:5981-5986, The American Society for Biochemistry and Molecular Biology, Inc. (1999).

Itoh, M., et al., "Direct Binding of Three Tight Junction-associated MAGUKs, ZO-1, ZO-2, and ZO-3, with the COOH Termini of Claudins," *J. Cell. Biol.* 147:1351-1363, The Rockefeller University Press (1999).

Itoh, M., et al., "Junctional adhesion molecule (JAM) binds to PAR-3: a possible mechanism for the recruitment of PAR-3 tight junctions," *J. Cell Biol.* 154:491-497, The Rockefeller University Press (Aug. 2001).

Knudsen, K.A., et al., "Interaction of α-Actinin with the Cadherin/Catenin Cell-Cell Adhesion Complex via α-Catenin," *J. Cell Biol.* 130:67-77, The Rockefeller University Press (1995).

Long, R.M., et al., "She2p is a novel RNA-binding protein that recruits the Myo4p-She3p complex to *ASH1* mRNA," *EMBO J.* 19:6592-6601, European Molecular Biology Organization (2000).

Lopez, M., et al., "The Human Poliovirus Receptor Related 2 Protein Is a New Hematopoietic/Endothelial Homophilic Adhesion Molecule," *Blood* 92:4602-4611, American Society of Hematology (1998).

Lopez, M., et al., "Complementary DNA characterization and chromosomal localization of a human gene related to the poliovirus receptor-encoding gene," *Gene* 155:261-265, Elsevier Science B.V. (1995).

Lopez, M., et al., "Nectin2α (PRR2α or HveB) and Nectin2δ Are Low-Efficiency Mediators for Entry of Herpes Simplex Virus Mutants Carrying the Leu25Pro Substitution in Glycoprotein D," *J. Virol.* 74:1267-1274, American Society for Microbiology (2000).

Mandai, K., et al., "Afadin: A Novel Actin Filament-binding Protein with one PDZ Domain Localized at Cadherin-based Cell-to-Cell Adherins Junction," *J. Cell Biol.* 139:517-528, The Rockefeller University Press (1997).

Martin-Padura, I., et al., "Junctional Adhesion Molecule, a Novel Member of the Immunoglobuliin Superfamily That Distributes at Intercellular Junctions and Modulates Monocyte Transmigration," *J. Cell Biol.* 142:117-127, The Rockefeller University Press (1998).

Miyahara, M., et al., "Interaction of Nectin with Afadin Is Necessary for Its Clustering at Cell-Cell Contact Sites but Not for Its *cis* Dimerization or *trans* Interaction," *J. Biol. Chem.* 275:613-618, The American Society for Biochemistry and Molecular Biology, Inc. (2000).

Mizoguchi, A., et al., "Nectin: an adhesion molecule involved in formation of synapses," *J. Cell. Biol.* 156:555-565, The Rockefeller University Press (Feb. 2002).

Morrison, M.E. and Racaniello, V.R., "Molecular Cloning and Expression of a Murine Homolog of the Human Poliovirus Receptor Gene," *J. Virol.* 66:2807-2813, American Society for Microbiology (1992).

Nagafuchi, A., "Molecular architecture of adherens junctions," *Curr. Opin. Cell—Biol.* 13:600-603, Elsevier Science Ltd. (Dec. 2001).

Nagafuchi, A., et al., "The 102 kd Cadherin-Associated Protein: Similarity to Vinculin and Posttranscriptional Regulation of Expression," *Cell* 65:849-857, Cell Press (1991).

Ozaki-Kuroda, K., et al., "Nectin Couples Cell-Cell Adhesion and the Actin Scaffold at Heterotypic Testicular Junctions," *Curr. Biol.* 12:1145-1150, Elsevier Science Ltd. (Jul. 2002).

Ozawa, M., et al., "The cytoplasmic domain of the cell adhesion molecule uvomorulin associates with three independent proteins structurally related in different species," *EMBO J.* 8:1711-1717, IRL Press (1989).

Ponting, C.P., "AF-6/cno: neither a kinesin nor a myosin, but a bit of both," *Trends Biochem. Sci.* 20:265-266, Elsevier Science Ltd. (1995).

Prasad, R., et al., "Cloning of the ALL-1 Fusion Partner, the AF-6 Gene, Involved in Acute Myeloid Leukemias with the t(6;11) Chromosome Translocation," *Cancer Res.* 53:5624-5628, The American Association for Cancer Research (1993).

Provost, E. and Rimm, D.L., "Controversies at the cytoplasmic face of the cadherin-based adhesion complex," *Curr. Opin. Cell Biol.* 11:567-572, Elsevier Science Ltd. (1999).

Reymond, N., et al., "Nectin4/PRR4, a New Afadin-associated Member of the Nectin Family That Trans-interacts with Nectin1/PRR1 through V Domain Interaction," *J. Biol. Chem.* 276:43205-43215, The American Society for Biochemistry and Molecular Biology, Inc. (Nov. 2001).

Rimm, D.L., et al., "$α_1$(E)-Catenin is an actin-binding and -bundling protein mediating the attachment of F-actin to the membrane adhesion complex," *Proc. Natl. Acad. Sci. USA* 92:8813-8817, The National Academy of Sciences (1995).

Sakisaka, T., et al., "Requirement of Interaction of Nectin-1α/HveC with Afadin for Efficient Cell-Cell Spread of Herpes Simplex Virus Type 1," *J. Virol.* 75:4734-4743, American Society for Microbiology (May 2001).

Satoh-Horikawa, K., et al., "Nectin-3, a New Member of Immunoglobulin-like Cell Adhesion Molecules That Shows Homophilic and Heterophilic Cell-Cell Adhesion Activities," *J. Biol. Chem.* 275:10291-10299, The American Society for Biochemistry and Molecular Biology, Inc. (2000).

Stevenson, B.R., et al., Identification of ZO-1: A High Molecular Weight Polypeptide Associated with the Tight Junction (Zonula Occludens) in a Variety of Epithelia, *J. Cell. Biol.* 103:755-766, The Rockefeller University Press (1986).

Suzuki, K., et al., "Mutations of *PVRL1*, encoding a cell-cell adhesion molecule/herpesvirus receptor, in cleft/palate-ectodermal dysplasia," *Nature Genet.* 25:427-430, Nature America, Inc. (2000).

Tachibana, K., et al., "Two Cell Adhesion Molecules, Nectin and Cadherin, Interact through Their Cytoplasmic Domain-associated Proteins," *J. Cell. Biol.* 150:1161-1175, The Rockefeller University Press (2000).

Takahashi, K., et al., "Nectin/PRR: An Immunoglobulin-like Cell Adhesion Molecule Rcruited to Cadherin-based Adherens Junctions through Interaction with Afadin, a PDZ Domain-containing Protein," *J. Cell Biol.* 145:539-549, The Rockefeller University Press (1999).

Takeichi, M., "Cadherin Cell Adhesion Receptors as a Morphogenetic Regulator," *Science* 251:1451-1455, American Association for the Advancement of Science (1991).

Takeichi, M., "Morphogenetic roles of classic cadherins," *Curr. Opin. Cell Biol.* 7:619-627, Current Biology Ltd. (1995).

Takeichi, M., et al., "Patterning of cell assemblies regulated by adhesion receptors of the cadherin superfamily," *Phil. Trans. R. Soc. Lond. B.* 355:885-890, The Royal Society (2000).

Tepass, U., et al,. "Cadherins in Embryonic and Neural Morphogenesis," *Nat. Rev. Mol. Cell. Biol.* 1:91-100, Nature Publishing Group (2000).

Tsukita, S., et al., "Molecular linkage between cadherins and actin filaments in cell-cell adherens junctions," *Curr. Opin. Cell Biol.* 4:834-839, Current Biology Ltd. (1992).

Tsukita, S., et al., "Occludin and claudins in tight-junction strands: leading or supporting players?," *Trends Cell Biol. 9*:268-273, Elsevier Science (1999).

Tsukita, S., et al., "Structural and signaling molecules come together at tight junctions," *Curr. Opin. Cell Biol. 11*:628-633, Elsevier Science Ltd. (1999).

Vleminckx, K. and Kemler, R., "Cadherins and tissue formation: integrating adhesion and signaling," *BioEssays 21*:211-220, John Wiley & Sons, Inc. (1999).

Warner, M.S., et al., "A Cell Surface with Herpesvirus Entry Activity (HveB) Confers Susceptibility to Infection by Mutants of Herpes Simplex Virus Type 1, Herpes Simplex Virus Type 2, and Pseudorabies Virus," *Virol. 246*:179-189, Academic Press (1998).

Watabe-Uchida, M., et al., "α-Catenin-Vinculin Interaction Functions to Organize the Apical Junctional Complex in Epithelial Cells," *J. Cell Biol. 142*:847-857, The Rockefeller University Press (1998).

Weiss, E.E., et al., "Vinculin Is Part of the Cadherin-Catenin Junctional Complex: Complex Formation between α-Catenin and Vinculin," *J. Cell Biol. 141*:755-764, The Rockefeller University Press (1998).

Willott, E., et al., "The tight junction protein ZO-1 is homologous to the *Drosophila* discs-large tumor suppressor protein of septate junctions," *Proc. Natl. Acad. Sci. USA 90*:7834-7838, The National Academy of Sciences (1993).

Wittchen, E.S., et al., "Exogenous Expression of the Amino-terminal Half of the Tight Junction Protein ZO-3 Perturbs Junctional Complex Assembly," *J. Cell Biol. 151*:825-836, The Rockefeller University Press (2000).

Yagi, T. and Takeichi, M., "Cadherin superfamily genes: functions, genomic organization, and neurologic diversity," *Genes Dev. 14*:1169-1180, Cold Spring Harbor Laboratory Press (2000).

Yokoyama, S., et al., "α-Catenin-independent Recruitment of ZO-1 to Nectin-based Cell-Cell Adhesion Sites through Afadin," *Mol. Biol Cell 12*:1595-1609, The American Society for Cell Biology (Jun. 2001).

Asada, M., et al., "Cloning and characterization of a novel afadin-binding protein localized at adherens junctions," *Jpn. J. Cancer Res. 93*:107, abs. No. 1096, Japanese Cancer Association (Oct. 2002).

Unverified English Translation of Asada, M., et al., "Cloning and characterization of a novel afadin-binding protein localized at adherens junctions," *Jpn. J. Cancer Res. 93*:107, abs. No. 1096, Japanese Cancer Association (Oct. 2002).

de Bruijn, D.R.H., et al., "The Cancer-Related Protein SSX2 Interacts With the Human Homologue of a Ras-like GTPase Interactor, RAB3IP, and a Novel Nuclear Protein, SSX2IP," *Genes, Chromosomes & Cancer 34*:285-298, Wiley-Liss, Inc. (Jul. 2002).

\* cited by examiner

FIG. 2

ADIP PROTEIN AND USE THEREOF

FIELD OF THE INVENTION

The present invention relates to a novel afadin DIL domain-binding protein (ADIP) and a gene encoding the protein, as well as methods of screening for pharmaceutical agents for diseases using the gene and diagnostic methods for the diseases.

BACKGROUND OF THE INVENTION

Cells in multicellular organisms recognize neighboring cells, adhere to each other and form intercellular junctions. Such junctions play essential roles in various cellular functions, including morphogenesis, differentiation, proliferation and migration (see M. Takeichi, "Cadherin cell adhesion receptors as a morphogenetic regulator." Science 1991, 251: 1451-1455; B. M. Gumbiner, "Cell adhesion: the molecular basis of tissue architecture and morphogenesis." Cell 1996, 84: 345-357; K. Vleminckx and R. Kemler, "Cadherins and tissue formation: integrating adhesion and signaling." Bioassays 1999, 21: 211-220; U. Tepass et al., "Cadherins in embryonic and neural morphogenesis." Nat. Rev. Mol. Cell Biol. 2000, 1: 91-100; M. Takeichi et al., "Patterning of cell assemblies regulated by adhesion receptors of the cadherin superfamily." Philos. Trans. R. Soc. Lond. B. Biol. Sci. 2000, 355: 885-890; T. Yagi and M. Takeichi, "Cadherin superfamily genes: functions, genomic organization, and neurologic diversity." Genes Dev. 2000, 14: 1169-1180). In polarized epithelial cells, intercellular adhesion is mediated through a junctional complex composed of tight junctions (TJs), adherens junctions (AJs) and desmosomes. The junctional structures are typically aligned from the apical to basal sides, while desmosomes are independently distributed in other areas.

According to ultrastructural analysis, AJs were originally defined as closely apposed plasma membrane domains fortified with dense cytoplasmic plaques, lined with actin filament (F-actin) bundles (see M. G. Farquhar and G. E. Palade, "Junctional complexes in various epithelia." J. Cell Biol. 1963, 17: 375-412). Molecular analysis showed that AJs are cell-cell adhesion sites assembled with actin-based cytoskeleton and several cytoplasmic components wherein typical cadherins function as cell adhesion molecules (see E. Provost and D. L. Rimm, "Controversies at the cytoplasmic face of the cadherin-based adhesion complex." Curr. Opin. Cell Biol. 1999, 11: 567-572; A. Nagafuchi, "Molecular architecture of adherens junctions." Curr. Opin. Cell Biol. 2001, 13: 600-603). Similar to other typical cadherins, E-cadherin is a single-pass transmembrane protein whose extracellular domain mediates homophilic recognition and adherens junction in a $Ca^{2+}$-dependent manner (see M. Takeichi, "Morphogenetic roles of classic cadherins." Curr. Opin. Cell Biol. 1995, 7: 619-627). E-cadherin associates with actin cytoskeleton through peripheral membrane proteins, including α-catenins, β-catenins, γ-catenins, α-actin and vinculin (see M. Ozawa et al., "The cytoplasmic domain of the cell adhesion molecule uvomorulin associates with three independent proteins structurally related in different species." EMBO J. 1989, 8: 1711-1717; A. Nagafuchi et al., "The 102 kd cadherin-associated protein: similarity to vinculin and posttranscriptional regulation of expression." Cell 1991, 65: 849-857; M. Watabe-Uchida et al., "α-Catenin-vinculin interaction functions to organize the apical junctional complex in epithelial cells." J. Cell Biol. 1998, 142: 847-857; E. E. Weiss et al., "Vinculin is part of the cadherin-catenin junctional complex: complex formation between alpha-catenin and vinculin." J. Cell Biol. 1998, 141: 755-764). β-Catenin directly interacts with the cytoplasmic tail of E-cadherin and connects E-cadherin to α-catenin that directly binds to F-actin (see D. L. Rimm et al., "Alpha 1(E)-catenin is an actin-binding and -bundling protein mediating the attachment of F-actin to the membrane adhesion complex." Proc. Nat. Acad. Sci. USA. 1995, 92: 8813-8817). α-Actinin and vinculin are F-actin-binding proteins that directly bind to α-catenin (see M. Watabe-Uchida et al., "α-Catenin-vinculin interaction functions to organize the apical junctional complex in epithelial cells." J. Cell Biol. 1998, 142: 847-857; E. E. Weiss et al., "Vinculin is part of the cadherin-catenin junctional complex: complex formation between alpha-catenin and vinculin." J. Cell Biol. 1998, 141: 755-764; K. A. Knudsen et al., "Interaction of alpha-actinin with the cadherin/catenin cell-cell adhesion complex via alpha-catenin." J. Cell Biol. 1995, 130: 67-77).

The association of E-cadherin with the actin cytoskeleton through these peripheral membrane proteins potentiate cell-cell adhesion by E-cadherin (see M. Takeichi, "Cadherin cell adhesion receptors as a morphogenetic regulator." Science 1991, 251: 1451-1455; Y. Imamura et al., "Functional domains of alpha-catenin required for the strong state of cadherin-based cell adhesion." J. Cell Biol. 1999, 144: 1311-1322).

The present inventors discovered that another cell-cell adhesion molecule (nectin) and F-actin-binding protein (afadin), which associates with nectin, also localize at AJs (see K. Mandai et al., "Afadin: A novel actin filament-binding protein with one PDZ domain localized at cadherin-based cell-to-cell adherens junction." J. Cell Biol. 1997, 139: 517-528; K. Takahashi et al., "Nectin/PRR: an immunoglobulin-like cell adhesion molecule recruited to cadherin-based adherens junctions through interaction with Afadin, a PDZ domain-containing protein." J. Cell Biol. 1999, 145: 539-549). Nectin and afadin strictly localized at AJs and, using ultrastructural analysis, they were defined as closely apposed plasma membrane domains fortified with dense cytoplasmic plaques lined with F-actin bundles (see M. G. Farquhar and G. E. Palade, "Junctional complexes in various epithelia." J. Cell Biol. 1963, 17: 375-412; K. Mandai et al., "Afadin: A novel actin filament-binding protein with one PDZ domain localized at cadherin-based cell-to-cell adherens junction." J. Cell Biol. 1997, 139: 517-528; K. Takahashi et al., "Nectin/PRR: an immunoglobulin-like cell adhesion molecule recruited to cadherin-based adherens junctions through interaction with Afadin, a PDZ domain-containing protein." J. Cell Biol. 1999, 145: 539-549). In contrast, E-cadherin is concentrated at AJs but is more widely distributed from the apical to basal sides of the lateral plasma membranes (see B. M. Gumbiner, "Cell adhesion: the molecular basis of tissue architecture and morphogenesis." Cell 1996, 84: 345-357; S. Tsukita et al., "Molecular linkage between cadherins and actin filaments in cell-cell adherens junctions." Curr. Opin. Cell Biol. 1992, 4: 834-839). Nectin is a $Ca^{2+}$-independent immunoglobulin-like cell-cell adhesion molecule (see K. Takahashi et al., "Nectin/PRR: an immunoglobulin-like cell adhesion molecule recruited to cadherin-based adherens junctions through interaction with Afadin, a PDZ domain-containing protein." J. Cell Biol. 1999, 145: 539-549; J. Aoki et al., "Mouse homolog of poliovirus receptor-related gene 2 product, mPRR2, mediates homophilic cell aggregation." Exp. Cell Res. 1997, 235: 374-384; M. Lopez et al., "The human poliovirus receptor related 2 protein is a new hematopoietic/endothelial homophilic adhesion molecule." Blood 1998, 92: 4602-4611; M. Miyahara et al., "Interaction of nectin with afadin is necessary for its clustering at cell-cell contact sites but not for its cis dimerization or trans interaction." J. Biol. Chem. 2000, 275: 613-618; K. Satoh-Horikawa et al., "Nectin-3, a new member of immunoglobulin-like cell adhesion molecules that shows homophilic and heterophilic cell-cell adhesion activities." J. Biol. Chem. 2000, 275: 10291-10299; N. Reymond et al., "Nectin4/PRR4: A new afadin-associated member of the nectin family that trans-interacts with nectin1/PRR1 through V domain interaction." J. Biol. Chem. 2001, 276: 43205-43215). At present, nectin comprises a family consisting of four membranes, i.e., nectin-1, -2, -3 and -4. All nectins, with the exception of nectin-4, have two or three splice variants, i.e., nectin-1α, -1β, -2α, -2δ, -3α, -3β and -3γ isoforms (see K. Takahashi et al., "Nectin/PRR: an immunoglobulin-like cell adhesion molecule recruited to cadherin-based adherens junctions through interaction with Afadin, a PDZ domain-containing protein." J. Cell Biol. 1999, 145: 539-549; K. Satoh-Horikawa et al., "Nectin-3, a new member of immunoglobulin-like cell adhesion molecules that shows homophilic and heterophilic cell-cell adhesion activities." J. Biol. Chem. 2000, 275: 10291-10299; N. Reymond et al., "Nectin4/PRR4: A new afadin-associated member of the nectin family that trans-interacts with nectin1/PRR1 through V domain interaction." J. Biol. Chem. 2001, 276: 43205-43215; M. E. Morrison and V. R. Racaniello, "Molecular cloning and expression of a murine homolog of the human poliovirus receptor gene." J. Virol. 1992, 66: 2807-2813; J. Aoki et al., "Amino acid residues on human poliovirus receptor involved in interaction with poliovirus." J. Biol. Chem. 1994, 269: 8431-8438; F. Eberle et al., "The human PRR2 gene, related to the human poliovirus receptor gene (PVR), is the true homolog of the murine MPH gene." Gene 1995, 159: 267-272; M. Lopez et al. "Complementary DNA characterization and chromosomal localization of a human gene related to the poliovirus receptor-encoding gene." Gene 1995, 155: 261-265; F. Cocchi et al., "The V domain of herpesvirus Ig-like receptor (HIgR) contains a major functional region in herpes simplex virus-1 entry into cells and interacts physically with the viral glycoprotein D." Proc. Natl. Acad. Sci. USA. 1998, 95: 15700-15705). Nectin-1 was originally identified as one of the poliovirus receptor-related proteins (PRR1) (see M. Lopez et al., "Complementary DNA characterization and chromosomal localization of a human gene related to the poliovirus receptor-encoding gene." Gene 1995, 155: 261-265). Nectin-2 was originally identified as a murine homolog of human poliovirus receptor protein (see M. E. Morrison and V. R. Racaniello, "Molecular cloning and expression of a murine homolog of the human poliovirus receptor gene." J. Virol. 1992, 66: 2807-2813), but turned out to be another poliovirus receptor-related protein (PRR2) (see F. Eberle et al., "The human PRR2 gene, related to the human poliovirus receptor gene (PVR), is the true homolog of the murine MPH gene." Gene 1995, 159: 267-272; M. Lopez et al., "Complementary DNA characterization and chromosomal localization of a human gene related to the poliovirus receptor-encoding gene." Gene 1995, 155: 261-265). PRR1 and PRR2 were later shown to serve as receptors for α-herpesvirus, facilitating their invasion and intercellular spreading, and thus were renamed HveC and HveB, respectively (see F. Cocchi et al., "The V domain of herpesvirus Ig-like receptor (HIgR) contains a major functional region in herpes simplex virus-1 entry into cells and interacts physically with the viral glycoprotein D." Proc. Natl. Acad. Sci. USA. 1998, 95: 15700-15705; F. Cocchi et al., "Cell-to-cell spread of wild-type herpes simplex virus type 1, but not of syncytial strains, is mediated by the immunoglobulin-like receptors that mediate virion entry, nectin1 (PRR1/HveC/HIgR) and nectin2 (PRR2/HveB)." J. Virol. 2000, 74: 3909-3917; R. J. Geraghty et al., "Entry of alphaherpesviruses mediated by poliovirus receptor-related protein 1 and poliovirus receptor." Science 1998, 280: 1618-1620; M. S. Warner et al., "A cell surface protein with herpesvirus entry activity (HveB) confers susceptibility to infection by mutants of herpes simplex virus type 1, herpes simplex virus type 2, and pseudorabies virus." Virology 1998, 246: 179-189; M. Lopez et al., "Nectin2α (PRR2α or HveB) and nectin2α are low-efficiency mediators for entry of herpes simplex virus mutants carrying the Leu25Pro substitution in glycoprotein D." J. Virol. 2000, 74: 1267-1274; T. Sakisaka et al., "Requirement of interaction of nectin-1 alpha/HveC with afadin for efficient cell-cell spread of herpes simplex virus type 1." J. Virol. 2001, 75: 4734-4743). All members of nectin have an extracellular domain with three immunoglobulin-like loops, a single transmembrane region and a cytoplasmic region. Furthermore, all of them, with the exception of nectin-1β, nectin-3γ and nectin-4, have a conserved motif of 4 amino acid residues (Glu/Ala-X-Tyr-Val) at their carboxy terminus, and this motif binds to the PDZ domain of afadin (see K. Mandai et al., "Afadin: A novel actin filament-binding protein with one PDZ domain localized at cadherin-based cell-to-cell adherens junction." J. Cell Biol. 1997, 139: 517-528; K. Takahashi et al., "Nectin/PRR: an immunoglobulin-like cell adhesion molecule recruited to cadherin-based adherens junctions through interaction with Afadin, a PDZ domain-containing protein." J. Cell Biol. 1999, 145: 539-549; K. Satoh-Horikawa et al., "Nectin-3, a new member of immunoglobulin-like cell adhesion molecules that shows homophilic and heterophilic cell-cell adhesion activities." J. Biol. Chem. 2000, 275: 10291-10299; N. Reymond et al., "Nectin4/PRR4: A new afadin-associated member of the nectin family that trans-interacts with nectin1/PRR1 through V domain interaction." J. Biol. Chem. 2001, 276: 43205-43215).

Afadin has at least two splice variants, namely, l- and s-afadins (see K. Mandai et al., "Afadin: A novel actin filament-binding protein with one PDZ domain localized at cadherin-based cell-to-cell adherens junction." J. Cell Biol. 1997, 139: 517-528). l-Afadin, the larger splice variant, binds to nectin and, through its F-actin binding domain, to F-actin. l-Afadin binds to the side of F-actin but does not crosslink with it to form bundles. l-Afadin has two Ras-associated domains (RA), a forkhead-associated domain (FHA), a dilute (DIL) domain, a PDZ domain, two proline rich domains (PR) and an F-actin-binding PR domain (see FIG. 1A). The DIL domain is found in afadin, dilute (DIL) and V-type myocin, comprising Myo2 and Myo4. However, the function of this domain is still unknown (see C. P. Ponting, "AF-6/cno: neither a kinesin nor a myosin, but a bit of both." Trends Biochem. Sci. 1995, 20: 265-266). Recent findings that the Myo4 region containing the DIL domain binds to an adaptor protein, She3 (see F. Bohl et al., "She2p, a novel RNA-binding protein tethers ASH1 mRNA to the Myo4p myosin motor via She3p." EMBO J. 2000, 19: 5514-5524; R. M. Long et al., "She2p is a novel RNA-binding protein that recruits the Myo4p-She3p complex to ASH1 mRNA." EMBO J. 2000, 19: 6592-6601) indicates that the DIL domain is involved in protein-protein interactions.

s-Afadin, the smaller splice variant, has two RA, FHA, DIL, PDZ and two PR domains, but lacks the F-actin-binding PR domain. Human s-afadin is identical to the gene product of AF-6, a gene that has been identified as an ALL-1 fusion partner involved in acute myeloid leukemias (see R. Prasad et al., "Cloning of the ALL-1 fusion partner, the AF-6 gene, involved in acute myeloid leukemias with the t(6;11) chromosome translocation." Cancer Res. 1993, 53: 5624-5628). Unless otherwise specified, "afadin" refers to l-afadin in the present specification.

Nectin supplies E-cadherin-β-catenin complex to the nectin-based cell-cell adhesion sites through afadin and α-catenin in fibroblast and epithelial cells (see K. Tachibana et al., "Two cell adhesion molecules, nectin and cadherin, interact through their cytoplasmic domain-associated proteins." J. Cell Biol. 2000, 150: 1161-1176; A. Fukuhara et al., "Involvement of Nectin in the Localization of Junctional Adhesion Molecule at Tight Junctions." Oncogene 2002, 21: 7642-7655). Furthermore, nectin supplies TJ components, including ZO-1, claudin, occludin and junction adhesion molecule (JAM), to the nectin-based cell-cell adhesion sites through afadin in fibroblasts and epithelial cells (see A. Fukuhara et al., "Involvement of Nectin in the Localization of Junctional Adhesion Molecule at Tight Junctions." Oncogene 2002, 21: 7624-7655; S. Yokoyama et al., "alpha-Catenin-independent Recruitment of ZO-1 to Nectin-based Cell-Cell Adhesion Sites through Afadin." Mol. Biol. Cell 2001, 12: 1595-1609; A. Fukuhara et al., "Role of Nectin in Organization of Tight Junctions in Epithelial Cells. Genes Cells." Genes Cells 2002, 7: 1059-1072). Claudin is an important cell-cell adhesion molecule that forms TJ strands (see M. Furuse et al., "A single gene product, claudin-1 or -2, reconstitutes tight junction strands and recruits occludin in fibroblasts." J. Cell Biol. 1998, 143: 391-401; M. Furuse et al., "Claudin-1 and -2: novel integral membrane proteins localizing at tight junctions with no sequence similarity to occludin." J. Cell Biol. 1998, 141: 1539-1550; S. Tsukita and M. Furuse, "Occludin and claudins in tight-junction strands: leading or supporting players?" Trends Cell Biol. 1999, 9: 268-273; S. Tsukita et al., "Structural and signalling molecules come together at tight junctions." Curr. Opin. Cell Biol. 1999, 11: 628-633), and occludin and JAM are other transmembrane proteins at TJs (see S. Tsukita and M. Furuse, "Occludin and claudins in tight-junction strands: leading or supporting players?" Trends Cell Biol. 1999, 9: 268-273; S. Tsukita et al., "Structural and signalling molecules come together at tight junctions." Curr. Opin. Cell Biol. 1999, 11: 628-633; I. Martin-Padura et al., "Junctional adhesion molecule, a novel member of the immunoglobulin superfamily that distributes at intercellular junctions and modulates monocyte transmigration." J. Cell Biol. 1998, 142: 117-127) Claudin, occludin and JAM interact with an F-actin-binding scaffold molecule, ZO-1 (see B. R. Stevenson et al., "Identification of ZO-1: a high molecular weight polypeptide associated with the tight junction (zonula occludens) in a variety of epithelia." J. Cell Biol. 1986, 103: 755-766; M. Itoh et al., "The 220-kD protein colocalizing with cadherins in non-epithelial cells is identical to ZO-1, a tight junction-associated protein in epithelial cells: cDNA cloning and immunoelectron microscopy." J. Cell Biol. 1993, 121: 491-502; M. Itoh et al., "Involvement of ZO-1 in cadherin-based cell adhesion through its direct binding to alpha catenin and actin filaments." J. Cell Biol. 1997, 138: 181-192; M. Itoh et al., "Characterization of ZO-2 as a MAGUK family member associated with tight as well as adherens junctions with a binding affinity to occludin and alpha catenin." J. Biol. Chem. 1999, 274: 5981-5986; M. Itoh et al., "Direct binding of three tight junction-associated MAGUKs, ZO-1, ZO-2, and ZO-3, with the COOH termini of claudins." J. Cell Biol. 1999, 147: 1351-1363; E. Willott et al., "The tight junction protein ZO-1 is homologous to the *Drosophila* discs—large tumor suppressor protein of septate junctions." Proc. Natl. Acad. Sci. USA. 1993, 90: 7834-7838; M. Furuse et al., "Direct association of occludin with ZO-1 and its possible involvement in the localization of occludin at tight junctions." J. Cell Biol. 1994, 127: 1617-1626; J. Haskins et al., "ZO-3, a novel member of the MAGUK protein family found at the tight junction, interacts with ZO-1 and occludin." J. Cell Biol. 1998, 141: 199-208; G. Bazzoni et al., "Interaction of Functional adhesion molecule with the tight junction components ZO-1, cingulin, and occludin." J. Biol. Chem. 2000, 275: 20520-20526; K. Ebnet et al., "Junctional adhesion molecule interacts with the PDZ domain-containing proteins AF-6 and ZO-1." J. Biol. Chem. 2000, 275: 27979-27988; E. S. Wittchen et al., "Exogenous expression of the amino-terminal half of the tight junction protein ZO-3 perturbs junctional complex assembly." J. Cell Biol. 2000, 151: 825-836; M. Itoh et al., "Junctional adhesion molecule (JAM) binds to PAR-3: a possible mechanism for the recruitment of PAR-3 to tight junctions." J. Cell Biol. 2001, 154: 491-497). In epithelial cells of afadin (−/−) mice and (−/−) embryoid bodies, the proper organization of AJs and TJs is impaired (see W. Ikeda et al., "Afadin: A key molecule essential for structural organization of cell-cell junctions of polarized epithelia during embryogenesis." J. Cell Biol. 1999, 146: 1117-1132). By positional cloning, nectin-1 has recently been related to cleft lip/palate-ectodermal dysplasia, which is characterized by cleft lip/palate, syndactyly, mental retardation and ectodermal dysplasia (see K. Suzuki et al., "Mutations of PVRL1, encoding a cell-cell adhesion molecule/herpesvirus receptor, in cleft lip/palate-ectodermal dysplasia." Nat. Genet. 2000, 25: 427-430).

In addition, the present inventors have recently identified that the nectin-afadin system is involved in the formation of synapses of neurons in cooperation with N-cadherin (see A. Mizoguchi et al., "Nectin: an adhesion molecule involved in formation of synapses." J. Cell Biol. 2002, 156: 555-565) and that the nectin-afadin system constitutes an important adhesion system in the organization of. Sertoli cell-spermatid junction of the testis (see K. Ozaki-Kuroda et al., "Nectin couples cell-cell adhesion and the actin scaffold at heterotypic testicular junctions." Curr. Biol. 2002, 12: 1145-1150). Therefore, nectin and afadin are important for the formation of a wide variety of intercellular junctions either together with or independently of known cell adhesion molecules. However, the molecular mechanism how the nectin-afadin system organizes these intercellular junctions is not yet fully understood.

SUMMARY OF THE INVENTION

This need in the art led to the present invention, and the objective of the present invention is to provide a novel afadin DIL domain-binding protein (ADIP) gene. Another objective of the present invention is to provide uses for this identified novel ADIP.

The present inventors vigorously investigated to achieve these objectives. First, the present inventors identified afadin-binding proteins by yeast two-hybrid screening to analyze how the nectin-afadin system organizes AJs and TJs. As a result, the present inventors succeeded in identifying a novel afadin-binding protein, ADIP (afadin DIL domain-interacting protein), that binds to the DIL domain of afadin which was used as a bait.

ADIP was further revealed to bind to α-actinin, which is an F-actin-bundling protein known to indirectly associate with E-cadherin through its direct binding to α-catenin (K. A. Knudsen, A. P. Soler, K. R. Johnson and M. J. Wheelock, "Interaction of alpha-actinin with the cadherin/catenin cell-cell adhesion complex via alpha-catenin." J. Cell Biol. 1995, 130: 67-77). These results suggested that ADIP may be associated with the nectin-afadin and E-cadherin-catenin systems through α-actinin, and that ADIP may be involved in the organization of the actin cytoskeleton at AJs through afadin and α-actinin. Therefore, ADIP is expected to be useful for the evaluation of agents involved in controlling the actin cytoskeleton.

Moreover, ADIP may be useful as a functional marker of the intercalate disc for heart diseases, such as myocardial infarction and myocarditis, due to its extremely high expression at the intercalate disc of cardiac muscle cells.

Specifically, the present invention relates to a novel ADIP gene and use thereof. More specifically, the present invention provides:

[1] a polynucleotide selected from the group consisting of:
  (a) a polynucleotide encoding a protein comprising the amino acid sequence of SEQ ID NO: 2 or 4;
  (b) a polynucleotide comprising a coding region of the nucleotide sequence of SEQ ID NO: 1 or 3;
  (c) a polynucleotide comprising a nucleotide sequence encoding a protein having binding activity to afadin or actinin and comprising the amino acid sequence of SEQ ID NO: 2 or 4, in which the amino acids are substituted, deleted, inserted and/or added; and
  (d) a polynucleotide which hybridizes under stringent conditions with a DNA comprising the nucleotide sequence of SEQ ID NO: 1 or 3 and which encodes a protein having binding activity to afadin or actinin;

[2] a polypeptide encoded by the polynucleotide of [1];

[3] a vector into which the polynucleotide of [1] is inserted;

[4] a host cell carrying the polynucleotide of [1];

[5] a method for producing the polypeptide encoded by the polynucleotide of [1], comprising the steps of culturing a host cell expressively carrying either said polynucleotide or a vector into which said polynucleotide is inserted, and recovering the produced polypeptide from said host cell or culture supernatant thereof;

[6] a polynucleotide which specifically hybridizes under highly stringent conditions to the polynucleotide of [1] and which comprises at least 15 nucleotides;

[7] an antisense polynucleotide to the polynucleotide of [1], wherein said antisense polynucleotide suppresses the expression of the polynucleotide of [1];

[8] an antibody which binds to the polypeptide of [2];

[9] a method of screening for a candidate compound of an actin cytoskeleton-controlling agent, comprising the steps of:
  (a) contacting afadin or actinin with the polypeptide of [2] and a test compound;
  (b) measuring the binding activity of afadin or actinin to the polypeptide of [2]; and
  (c) selecting the test compound which alters the binding activity, compared with that which occurs in the absence of the test compound;

[10] a method for assaying a heart disease which comprises the step of detecting the expression level of a gene encoding the polypeptide of [2] in a test subject, wherein an elevated level of gene expression as compared to control expression is indicative of heart disease;

[11] the method for assaying a heart disease of [10], comprising the steps of:
  (a) extracting an RNA sample from cardiac muscle cells of a test subject;
  (b) measuring the amount of RNA encoding the polypeptide of [2] contained in said RNA sample; and
  (c) comparing the amount of the measured RNA with a control, wherein an elevated level of RNA is indicative of heart disease;

[12] the method for assaying a heart disease of [10], comprising the steps of:
  (a) extracting a protein sample from cardiac muscle cells of a subject;
  (b) measuring the amount of the polypeptide of [2] contained in said protein sample; and
  (c) comparing the amount of the measured polypeptide with control, wherein an elevated level of polypeptide is indicative of heart disease;

[13] the method for diagnosing a heart disease of any one of [10] to [12], wherein the heart disease is myocardial infarction or myocarditis;

[14] the polynucleotide of [1], wherein said polynucleotide is the polynucleotide of (a);

[15] the polynucleotide of [1], wherein said polynucleotide is the polynucleotide of (b);

[16] the polynucleotide of [1], wherein the polynucleotide of (c) comprises the amino acid sequence of SEQ ID NO: 2 or 4, in which up to 10% of the amino acids are substituted, deleted, inserted, and/or added;

[17] the polynucleotide of [1], wherein the polynucleotide (c) comprises a nucleotide sequence encoding a protein having at least 70% indentity to SEQ ID NO: 2 or 4;

[18] the polynucleotide of [1], wherein the polynucleotide (d) has at least 70% identity to SEQ ID NO: 1 or 3;

[19] the polypeptide of [2], wherein the polypeptide has at least 70% indentity to SEQ ID NO: 2 or 4; and

[20] the polypeptide of [2], wherein the polypeptide comprises the amino acid sequence of SEQ ID NO: 2 or 4.

BRIEF DESCRIPTION OF THE DRAWINGS

FIG. 1(A) shows a schematic illustration of the structure of afadin, including the following domains: RA, Ras-associated domain; FHA, Forkhead-associated domain; DIL, Dilute domain; PDZ, PDZ domain; and PR, proline-rich domain.

FIG. 1(B) shows the results of yeast two-hybrid assay, indicating the specific binding of ADIP to the DIL domain of afadin.

FIG. 2 depicts the amino acid sequences of ADIP.

FIG. 2(A) shows the deduced amino acid sequences of rat ADIP, mouse ADIP and human KIAA0923. Identical sequences are highlighted in gray. Putative coiled-coil domains are underlined.

FIG. 2(B) shows the result of comparison of molecular weight of native and recombinant ADIP proteins. pCMV HA mADIP was transfected into HEK293 cells and the cell extract was subjected to SDS-PAGE (10% polyacrylamide gel), followed by Western blotting with the anti-ADIP pAb (M57) The extracts derived from control HEK293 and MDCK cells were similarly subjected to SDS-PAGE, followed by Western blotting. Lane 1, control HEK293 cells (1 μg protein); lane 2, pCMV HA mADIP-transfected HEK293 cells (1 μg protein); and lane 3, MDCK cells (1 μg of protein).

FIG. 3(A) shows a schematic illustration of the structure of mouse ADIP and the results of yeast two-hybrid analysis of the afadin- or α-actinin-binding regions of ADIP. CC, coiled-coil domain. ADIP, afadin (DIL domain) and α-actinin were constructed into pGBDU or pGAD and co-transfected into reporter yeast strains. As shown by the expression of the HIS3 and ADE2 reporter genes, the binding of ADIP to afadin or α-actinin was determined by evaluating growth of the yeast strains on synthetic complete media lacking histidine and adenine, respectively. +, with interaction; −, no interaction; NT, not tested.

FIG. 3(B) shows the result of co-immunoprecipitation of the T7-tagged DIL domain of afadin with the FLAG-tagged mADIP-C. Expression vectors were transfected into HEK293 cells as indicated. The T7-tagged DIL domain of afadin specifically co-immunoprecipitated with the FLAG-tagged mADIP-C, as shown by Western blotting with the anti-T7 and anti-FLAG mAbs.

FIG. 3(C) shows the in vitro binding of afadin to MBP-mADIP. The extract of MDCK cells was incubated with either MBP or MBP-mADIP (full-length) immobilized on amylose resin beads. The beads were then subjected to SDS-PAGE (10% polyacrylamide gel), followed by Western blotting with anti-afadin mAb.

FIG. 3(D) shows the result of co-immunoprecipitation of endogenous afadin with endogenous ADIP from MDCK cells. The extracts of MDCK cells were immunoprecipitated with the anti-ADIP pAb (M05) and analyzed by Western blotting with anti-ADIP pAb (M05) and anti-α-afadin mAb. The results represent three independent experiments.

FIG. 4(A) shows the result of Northern blotting analysis. Mouse RNA blotted membranes (Clontech) were hybridized with the $^{32}$P-labeled fragment (bp 552-3194) of the ADIP cDNA, followed by autoradiography. Lane 1, heart; Lane 2, brain; Lane 3, spleen; Lane 4, lung; Lane 5, liver; Lane 6, skeletal muscle; Lane 7, kidney; and Lane 8, testis (short exposure).

FIG. 4(B) shows the result of Western blotting analysis. The homogenates of various mouse tissues (30 μg protein each) were subjected to SDS-PAGE (10% polyacrylamide gel), followed by Western blotting with anti-ADIP pAb (M57). Lane 1, heart; Lane 2, brain; Lane 3, spleen; Lane 4, lung; Lane 5, liver; Lane 6, skeletal muscle; Lane 7, kidney; Lane 8, testis; and Lane 9, MDCK cells.

FIG. 4(C) shows the subcellular distribution of ADIP in rat liver. Subcellular fractionation of rat liver was performed, and each fraction (30 μg protein each) was subjected to SDS-PAGE (10% polyacrylamide gel), followed by Western blotting with anti-ADIP pAb (M57) or the anti-afadin mAb. Lane 1, homogenate fraction; Lane 2, soluble fraction; Lane 3, pellet fraction; Lane 4, fraction rich in bile ducts; Lane 5, fraction rich in AJs and TJs. The results represent three independent experiments.

FIG. 5(A) shows the result of staining with ADIP and afadin.

FIG. 5(B) shows the result of staining with ADIP and vinculin. Bars, 10 μm. The results represent three independent experiments.

FIG. 6(A) shows supplementation of ADIP to the nectin-2α-based cell-cell adhesion sites. Nectin-2a-L cells transiently expressing HA-tagged ADIP (rADIP-C; aa 159-613) were double-stained with anti-HA and anti-afadin mAb. Arrows show nectin-2α-based cell-cell adhesion sites.

FIG. 6(B) shows the lack of supplementation of ADIP to the nectin-2α-ΔC-based cell-cell adhesion sites. Nectin-2α-ΔC-L cells transiently expressing HA-tagged ADIP (rADIP-C; aa 159-613) were double-stained with anti-HA and anti-afadin mAb. Arrows show nectin-2α-ΔC-based cell-cell adhesion sites. Bars, 10 μm. The results represent three independent experiments.

FIGS. 7(A) and (B) show localization of ADIP, afadin and ZO-1. In FIG. 7 (A), the frozen sections were triple-stained with anti-ADIP pAb (M01), anti-afadin and anti-ZO-1 mAb. In FIG. 7(B), the frozen sections were double-stained with anti-ADIP pAb (M01) and anti-afadin mAb (Left panels) or with anti-ADIP pAb (M01) and anti-ZO-1 mAb (right panels). Arrowheads, ADIP signals co-localized with the afadin signal; arrows, ADIP signals localized at a slightly more basal side than the ZO-1 signal; and bars, 10 μm.

FIG. 7(C) shows ultrastructural localization of ADIP in mouse small intestine absorptive epithelial cells. The mouse small intestine absorptive epithelial cells were labeled with anti-ADIP pAb (M01) using the ultra-thin frozen section technique. AJ, adherens junctions; DS, desmosome; TJ, tight junctions; and bars, 0.1 μm.

FIG. 7(D) shows the absence of ADIP at cell-matrix junctions in mouse cardiac cells. The frozen sections were double-stained with anti-ADIP pAb (M01) and anti-vinculin mAb. Arrowheads, intercalated disc; arrows, costamere; and bars, 50 μm. The results represent three independent experiments.

FIG. 8(A) shows the localization of ADIP, afadin and E-cadherin in cells cultured at 2 mM $Ca^{2+}$ (normal $Ca^{2+}$).

FIG. 8(B) shows the disappearance of immunofluorescence signal of ADIP in the plasma membrane due to the change of $Ca^{2+}$ concentration from normal to low in the media. MDCK cells were incubated at 2 μM $Ca^{2+}$ for 120 min (low $Ca^{2+}$).

FIG. 8(C) shows the supplementation of ADIP into the cell-cell adhesion sites due to the change of $Ca^{2+}$ concentration from low to normal in the media. MDCK cells were cultured at 2 μM $Ca^{2+}$ for 120 min and then incubated at 2 mM $Ca^{2+}$ for 60 min (low $Ca^{2+}$+normal $Ca^{2+}$).

FIG. 8(D) shows the lack of supplementation of ADIP at TPA-induced TJ-like structure. MDCK cells were cultured at 2 μM $Ca^{2+}$ for 120 min and then incubated at 100 nM TPA for 60 min (low $Ca^{2+}$+TPA). Bars, 10 μm. The results represent three independent experiments.

FIG. 9(A) shows a schematic illustration of the structure of α-actinin-1 and the results of yeast two-hybrid analysis of the ADIP-binding regions of α-actinin-1. CH, carponin homologous domain; SPEC, spectrin-like repeat; and EF, EF hand. As indicated by the expression of the HIS3 and ADE2 reporter genes, the binding of α-actinin to ADIP was determined by evaluating the growth of the yeast strain on synthetic complete medium lacking histidine and adenine, respectively. +, interacted; +/−, weakly interacted; and −, not interacted.

FIG. 9(B) shows the result of co-immunoprecipitation of the HA-tagged α-actinin-1-C with the FLAG-tagged MADIP-M. Expression vectors were transfected into HEK293 cells as indicated. The HA-tagged α-actinin-1-C specifically co-immunoprecipitated with the FLAG-tagged mADIP-M, as shown by Western blotting with anti-HA and anti-FLAG mAbs.

FIG. 9(C) shows the result of co-immunoprecipitation of endogenous α-actinin with the FLAG-tagged mADIP-M. Expression vectors were transfected into HEK293 cells as indicated. Endogenous α-actinin-1 specifically co-immunoprecipitated with FLAG-tagged mADIP-M, as shown by Western blotting with anti-α-actinin pAb and anti-FLAG mAb.

FIG. 9(D) shows the result of co-immunoprecipitation of endogenous α-actinin and endogenous afadin with endogenous ADIP from MDCK cells. The extracts of MDCK cells were immunoprecipitated with anti-ADIP antibody (M05) and analyzed by Western blotting with anti-ADIP (M05), anti-α-actinin and anti-afadin Abs. The results represent three independent experiments.

FIG. 10(A) shows the localization of ADIP and α-actinin in MDCK cells. Cells were double-stained with anti-ADIP pAb (M05) and anti-α-actinin mAb.

FIG. 10(B) shows the localization of ADIP and α-actinin in mouse small intestine absorptive epithelial cells. The frozen sections were double-stained with anti-ADIP pAb (M01) and anti-α-actinin mAb. Bars, 10 μm. The results represent three independent experiments.

DETAILED DESCRIPTION OF THE INVENTION

Figure 1:
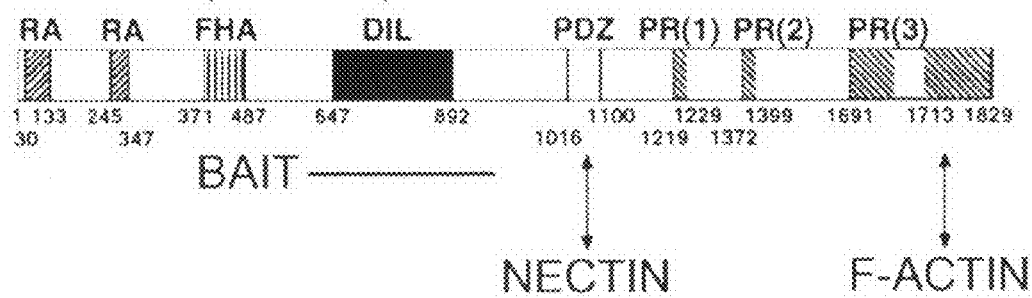
FIG. 1 depicts the binding of ADIP to the DIL domain of afadin.
Figure 1:
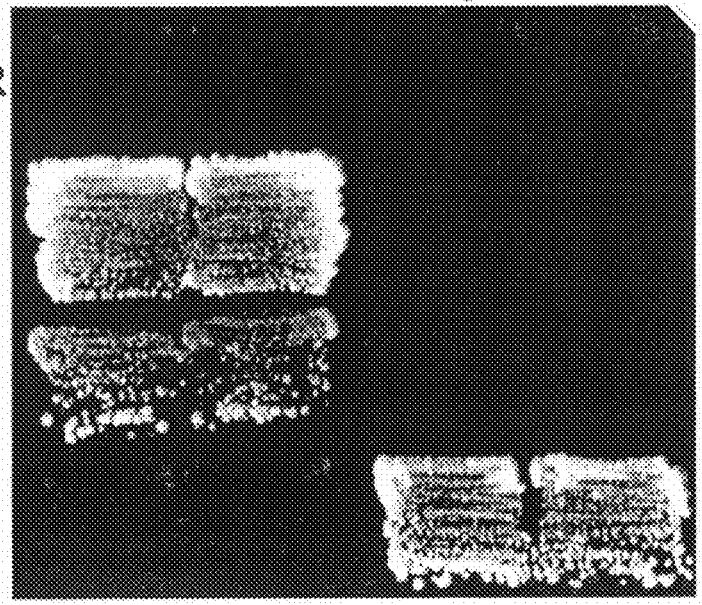

The present invention provides polynucleotides encoding novel protein, ADIP, which binds to the afadin DIL domain. The polynucleotide sequence encoding mouse ADIP and the amino acid sequence of polypeptide encoded by the polynucleotide, identified by the present inventors and encompassed by the present invention, are shown in SEQ ID NOs: 1 and 2, respectively. Moreover, the polynucleotide sequence encoding rat ADIP and the amino acid sequence of polypeptide encoded by the polynucleotide, also identified by the present inventors and encompassed by the present invention, are shown in SEQ ID NOs: 3 and 4, respectively.

The present invention also relates to polypeptides functionally equivalent to the polypeptides identified by the present inventors and polynucleotides encoding such functionally equivalent polypeptides. Herein, the phrase "functionally equivalent" means that the subject polypeptide has equivalent biological characteristics to a polypeptide identified by the present inventors. An example of a biological characteristic of ADIP includes the binding activity to afadin and/or actinin. Therefore, the present invention includes polynucleotides comprising the nucleotide sequence encoding a protein that consists of the amino acid sequence of SEQ ID NO: 2 or 4, in which one or more amino acids are substituted, deleted, inserted and/or added, so long as the resulting proteins retain the binding activity to afadin or actinin. Moreover, the present invention also includes polynucleotides that hybridize under stringent conditions with a DNA consisting of the nucleotide sequences of SEQ ID NO: 1 or 3, so long as the resulting polynucleotides encode proteins having the binding activity to afadin or actinin. The determination of the above-mentioned "binding activity" can be conducted by methods well known to those skilled in the art, such as the yeast two-hybrid system. The term "actinin" herein generally indicates "α-actinin".

The polynucleotides of the present invention can be isolated by methods well known to those skilled in the art. Examples of such methods include hybridization technique (E. M. Southern, J. Mol. Biol. 1975, 98: 503-517) and polymerase chain reaction (PCR) technique (R. K. Saiki et al., Science 1985, 230: 1350-1354; R. K. Saiki et al., Science 1988, 239: 487-491). More specifically, those skilled in the art can generally isolate polynucleotides highly homologous to the polynucleotides consisting of the nucleotide sequence of SEQ ID NO: 1 or 3 from other animals (such as human), using the polynucleotide of SEQ ID NO: 1 or 3 or parts thereof as probes or using the oligonucleotide which specifically hybridizes with the polynucleotide consisting of the nucleotide sequence of SEQ ID NO: 1 or 3 as primers. Furthermore, polynucleotides that can be isolated by hybridization techniques or PCR techniques and that hybridize with polynucleotides consisting of the nucleotide sequence of SEQ ID NO: 1 or 3 are also included in the polynucleotides of the present invention. Examples of such polynucleotides include polynucleotides encoding the human homolog of ADIP.

Hybridization reactions to isolate polynucleotides as described above are preferably conducted under stringent conditions. Examples of stringent hybridization conditions includes conditions comprising: 6 M urea, 0.4% SDS and 0.5×SSC, and those having a stringency equivalent to the conditions. Polynucleotides with higher homology are expected to be isolated when hybridization is performed under conditions with higher stringency, for example, 6 M urea, 0.4% SDS and 0.1×SSC. The polynucleotides isolated under higher stringency conditions, such as described above, are expected to encode a polypeptide having a higher homology at the amino acid level to the amino acid sequence of SEQ ID NO: 2 or 4. Herein, "high homology" means an identity of at least 70% or more, more preferably 80% or more, further more preferably 90% or more, and most preferably 95% or more, in the whole amino acid sequence.

The degree of identity at the amino acid sequence level or nucleotide sequence level can be determined using the BLAST algorithm by Karlin and Altschul (S. Karlin and S. F. Altschul, Proc. Natl. Acad. Sci. USA. 1990, 87: 2264-2268; S. Karlin and S. F. Altschul, Proc. Natl. Acad. Sci. USA. 1993, 90: 5873-5877). The BLAST algorithm-based programs, called BLASTN and BLASTX, have been developed (S. F. Altschul et al., J. Mol. Biol. 1990, 215: 403). When a nucleotide sequence is analyzed according to BLASTN, parameters are set, for example, at score=100 and word length=12. On the other hand, parameters used for the analysis of amino acid sequences by BLASTX are set, for example, at score=50 and word length=3. Default parameters of each program are used when BLAST and Gapped BLAST programs are used. Specific procedures for such analysis are known (http://www.ncbi.nlm.nih.gov).

Polynucleotides of the present invention include genomic DNAs, cDNAs, mRNAs, and chemically synthesized DNAs and RNAs. There is no restriction on the length of the polynucleotide of the present invention, but it preferably comprises at least 15, 20, 30, 40, 50, 100, 150, 200, 300, 400, 500, 1000, 1500, 2000, 2500, or 3000 nucleotides. A genomic DNA or cDNA can be prepared according to conventional methods known to those skilled in the art. For example, genomic DNA can be prepared as follows: (i) extracting genomic DNA from organisms comprising the polynucleotide encoding ADIP; (ii) constructing a genomic library (using, for example, a plasmid, phage, cosmid, BAC or PAC, as a vector); (iii) spreading the library; and then (iv) conducting colony hybridization or plaque hybridization using probes prepared based on the polynucleotide (e.g., SEQ ID NO: 1 or 3) encoding an ADIP of the present invention. Alternatively, the genomic DNA can be prepared by PCR, using primers specific to a polynucleotide (e.g., SEQ ID NO: 1 or 3) encoding the ADIP of the present invention. On the other hand, the cDNA can be prepared, for example, as follows: (i) synthesizing cDNAs based on mRNA extracted from organisms comprising the polynucleotide encoding an ADIP; (ii) constructing a cDNA library by inserting the synthesized cDNA into vectors, such as λZAP; (iii) spreading the cDNA library; and (iv) conducting colony hybridization or plaque hybridization as described above. Alternatively, the cDNA can also be prepared by PCR.

The present invention also provides polynucleotides encoding proteins structurally similar and functionally equivalent to the protein consisting of amino acid sequence of SEQ ID NO: 2 or 4. Mutated or modified proteins, proteins having amino acid sequences modified by deleting, adding and/or replacing one or more amino acid residues of a certain amino acid sequence, have been known to retain the original biological activity (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413). There is no limitation on the number and sites of the amino acid mutation in proteins as described above so long as the mutated polypeptide retains the functions of the original polypeptide. The number of mutations may be typically less than 10%, preferably less than 5%, and more preferably less than 1% of the total amino acid residues.

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a protein to which one or more amino acids residues are added is a fusion protein containing the an ADIP protein. Fusion proteins are fusions of a reference protein and other peptides or proteins, and are included in the present invention. Fusion proteins can be made by techniques well known to a person skilled in the art, such as by linking the DNA encoding an ADIP protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp, T. P. et al., Biotechnology (1988) 6, 1204-1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, a-tubulin fragment, B-tag, Protein C fragment, and such. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the protein of the present invention and expressing the fused DNA prepared.

Exemplary methods well known to those skilled in the art for preparing a polynucleotide as described above include site-directed mutagenesis (W. Kramer and H-J. Fritz, Methods Enzymol. 1987, 154: 350) for introducing mutations in the polynucleotide, in addition to the hybridization and PCR techniques described above. The amino acid sequence of a protein may also be mutated in nature due to a mutation of the nucleotide sequence encoding the protein. Additionally, degeneracy mutant polynucleotides, in which nucleotide sequence mutations do not give rise to any amino acid sequence mutations in the protein (degeneracy mutants), are also included in the present invention. Furthermore, the present invention includes the polypeptides which are encoded by the polynucleotides of the present invention as described above.

The present invention provides vectors containing polynucleotides of the present invention, host cells retaining polynucleotides or the vector of the present invention, and methods for producing polypeptides of the present invention utilizing the host cells.

The vector of the present invention is not limited so long as the DNA inserted in the vector is stably retained. For example, pBluescript vector (Stratagene) is preferable as a cloning vector when using *E. coli* as the host. When using a vector for producing a polypeptide of the present invention, an expression vector is particularly useful. The expression vector is not specifically limited, so long as it expresses polypeptides in vitro, in *E. coli*, in cultured cells and in vivo. Preferable examples of the expression vectors include the pBEST vector (ProMega) for in vitro expression, the pET vector (Invitrogen) for the expression in *E. coli*, the pME18S-FL3 vector (GenBank Accession No. AB009864) for the expression in cultured cells and the pME18S vector (Mol. Cell Biol. 1988, 8: 466-472) for in vitro expression. The insertion of a DNA of the present invention into a vector can be carried out by conventional methods, for example, the ligase reaction using restriction enzyme sites (Current Protocols in Molecular Biology, edit. Ausubel et al., Publish. John Wiley & Sons, 1987, Section 11.4-11.11).

The host cell to which the vector of the present invention is introduced is not specifically limited, and various host cells can be used according to the objects of the present invention. Examples cells for expressing the polypeptides include, but are not limited to, bacterial cells (e.g., *Streptococcus, Staphylococcus, E. coli, Streptomyces, Bacillus subtilis*), fungal cells (e.g., yeast, *Aspergillus*), insect cells (e.g., *Drosophila* S2, *Spodoptera* SF9), animal cells (e.g., CHO, COS, HeLa, C127, 3T3, BHK, HEK293, Bowes melanoma cell) and plant cells. The transfection of a vector to a host cell can be carried out by conventional methods, such as the calcium phosphate precipitation method, the electroporation method (Current protocols in Molecular Biology, edit. Ausubel et al., Publish. John Wiley & Sons, 1987, Section 9.1-9.9), the Lipofectamine method (GIBCO-BRL), the microinjection method, and such.

Appropriate secretion signals can be incorporated into the polypeptide of interest in order to secrete polypeptides into the lumen of endoplasmic reticulum, into cavity around the cell or into the extracellular environment by expressing them in a host cell. These signals may be endogenous signals or signals from a different species to the objective polypeptide.

When a polypeptide of the present invention is secreted into the culture media, the culture media is collected to collect the polypeptide of the present invention. When a polypeptide of the present invention is produced intracellularly, the cells are first lysed, and then, the polypeptides are collected.

In order to collect and purify a polypeptide of the present invention from a recombinant cell culture, methods known in the art, including, but not limited to, ammonium sulfate or ethanol precipitation, extraction by acid, anionic or cationic exchange chromatography, phosphocellulose chromatography, hydrophobic interaction chromatography, affinity chromatography, hydroxylapatite chromatography and lectin chromatography, can be used.

The present invention provides nucleotides, having a chain length of at least 15 nucleotides, which are complementary to a polynucleotide isolated by the present inventors (a polynucleotide or a complementary strand thereof consisting of the nucleotide sequence of SEQ ID NO: 1 or 3). Herein, the phrase "complementary strand" is defined as one strand of a double strand nucleic acid composed of A:T (A:U in case of RNA) and G:C base pairs to the other strand. Furthermore, the term "complementary" is not only used for nucleotides that completely match within a continuous region of at least 15 sequential nucleotides, but also those having a homology of at least 70%, preferably at least 80%, more preferably 90% and most preferably 95% or higher within that region. The homology may be determined using an algorithm described herein or an equivalent method. Such nucleotides may be used as probe and primers for detection, isolation or amplification of the polynucleotides of the present invention. Typical polynucleotides used as primers generally have a chain length of 15 to 100 nucleotides and preferably 15 to 35 nucleotides. Alternatively, polynucleotides used as probes may have a chain length of at least 15 nucleotides, preferably at least 30 nucleotides, containing at least a portion or the whole sequence of a DNA of the present invention. Such polynucleotides preferably hybridize specifically to a polynucleotide encoding a polypeptide of the present invention. The phrase "hybridize specifically" as used herein means that a nucleotide hybridizes under a normal hybridization condition, preferably a stringent condition with a polynucleotide (SEQ ID NO: 1 or 3) identified by the present inventors, but not with DNAs encoding other polypeptides.

Furthermore, the polynucleotides include those that suppress the expression of genes encoding the polypeptides of the present invention. Such polynucleotides include antisense polynucleotides (antisense DNA/RNA; antisense RNAs, which are complementary to transcriptional products of the genes encoding the polypeptides of the present invention, and DNAs encoding the RNAs) and ribozymes (DNAs encoding RNAs having ribozyme activities to specifically cleave transcriptional products of the genes encoding the polypeptides of the present invention).

A plurality of factors, such as those described below, arise as a result of actions suppressing the expression of a target gene by an antisense polynucleotide: inhibition of transcription initiation by the formation of a triple strand; suppression of transcription through hybridization with a local open loop conformation site formed by an RNA polymerase; inhibition of transcription by hybridization with RNA, which is in course of synthesis; suppression of splicing through hybridization at a junction of intron and exon; suppression of splicing through hybridization with a spliceosome forming site; suppression of transfer from the nuclei to cytoplasm through hybridization with mRNAs; suppression of splicing through hybridization with capping sites or poly(A) addition sites; suppression of translation initiation through hybridization with a translation initiation factor binding site; suppression of translation through hybridization with the ribosome binding site near the initiation codon; inhibition of elongation of peptide chain through hybridization with the translation regions and polysome binding sites of mRNAs; and suppression of expression of genes by hybridization with the interaction sites between nucleic acids and proteins. These actions inhibit the processes of transcription, splicing and/or translation to suppress the expression of a target gene (Hirajima and Inoue, "New Biochemistry Experimental Course No. 2, Nucleic Acid IV, Duplication and Expression of Genes", Japan Biochemical Society ed., Tokyo Kagaku Doujin, 1993, 319-347).

The antisense polynucleotides of the present invention may suppress the expression of the target gene through any of the above-mentioned actions. According to one embodiment, an antisense sequence designed to be complementary to a non-translated region near the 5' terminus of mRNA of a gene may effectively inhibit the translation of the gene. Additionally, sequences which are complementary to the coding region or the 3' non-translated region can be also used. As described above, polynucleotides containing antisense sequences not only to the translation region of a gene, but also those to sequences of non-translated regions are included in the antisense polynucleotides of the present invention. The antisense polynucleotides to be used in the present invention are preferably linked downstream of an appropriate promoter and a sequence including a transcriptional termination signal is preferably linked to the 3'-side thereof. The sequence of the antisense polynucleotide is preferably complementary to the target gene or a part thereof; however, so long as the expression of the gene can be effectively inhibited, it does not have to be a DNA completely complementary to the target sequence. The transcribed RNA (antisense polynucleotide) is preferably 90% or more, more preferably 95% or more, complementary to the transcribed product of the target gene. In order to effectively inhibit the expression of the target gene using an antisense sequence, the antisense polynucleotide has at least a chain length of 15 nucleotides or more, preferably 100 nucleotides, more preferably 500 nucleotides, and usually has a chain length less than 3000 nucleotides, preferably less than 2000 nucleotides to cause an antisense effect.

The antisense polynucleotide can be prepared, for example, by the phosphorothionate method (Stein, "Physicochemical properties of phosphorothioate oligodeoxynucleotides." Nucleic Acids Res. 1988, 16: 3209-3221) based on the sequence information of a polynucleotide (for example, the sequence of SEQ ID NO: 1 or 3) encoding a polypeptide of the present invention.

Furthermore, suppression of the expression of endogenous genes can be also achieved utilizing polynucleotides encoding ribozymes. Ribozymes are RNA molecules having catalytic activity. There exist ribozymes with various activities, and research on ribozymes as an enzyme for truncating RNA allowed for the design of ribozymes that cleave RNAs in a site-specific manner. There are ribozymes which are larger than 400 nucleotides, such as Group I intron type ribozymes and M1RNA, a member of RNaseP, as well as those which have an active domain of about 40 nucleotides, called hammer-head type or hairpin type ribozyme (Makoto Koizumi and Eiko Ohtsuka, Protein Nucleic Acid and Enzyme (PNE) 1990, 35: 2191).

For example, the hammer-head type ribozyme cleaves the 3'-side of C15 of G13U14C15 within its own sequence. A base pair formation of the U14 with the A at position 9 is important for the activity and the clevage is demonstrated to proceed even if the C at position 15 is A or U (M. Koizumi et al., FEBS Lett. 1988, 228: 225). Restriction enzymatic RNA-truncating ribozymes recognizing sequences of UC, UU or UA in a target RNA may be generated by designing the substrate binding site of the ribozyme complementary with the RNA sequence near the target site (M. Koizumi et al., FEBS Lett. 1988, 239: 285; Makoto Koizumi and Eiko Ohtsuka, Protein Nucleic Acid and Enzyme (PNE) 1990, 35: 2191); M. Koizumi et al., Nucleic Acids Res. 1989, 17: 7059).

Furthermore, the hairpin type ribozymes are also useful in the context of the present invention. The hairpin type ribozymes are found on, for example, the minus chain of a satellite RNA of tobacco ringspot virus (J. M. Buzayan, Nature 1986, 323: 349). It is also demonstrated that this ribozyme can be designed to cause a target specific RNA truncation (Y. Kikuchi and N. Sasaki, Nucleic Acids Res. 1992, 19: 6751; Y. Kikuchi, Chemistry and Organism 1992, 30: 112).

When a polynucleotide suppressing the expression of a gene encoding a polypeptide of the present invention is used in gene therapy, for example, it may be administered to a patient by the ex vivo method, in vivo method and such, using, for example, viral vectors including, but not limited to, retroviral vector, adenoviral vector and adeno-associated viral vectors; and non-viral vectors such as liposome.

The present invention provides antibodies that bind to a polypeptide of the present invention. Herein, the term "antibodies" encompasses polyclonal antibodies, monoclonal antibodies, chimeric antibodies, single-stranded antibodies, humanized antibodies and Fab fragments including Fab or other products of the immunoglobulin expression library.

A polypeptide of the present invention or fragment or analog thereof, or a cell that expresses one of these can be used as an immunogen for producing antibodies binding to a polypeptide of the present invention. The antibodies are preferably immunospecific to a polypeptide of the present invention. The term "immunospecific" means that the antibody has substantially higher affinity to a polypeptide of the present invention than to other polypeptides.

The antibodies binding to a polypeptide of the present invention can be prepared by conventional methods. For example, a polyclonal antibody can be obtained as follows: A polypeptide of the present invention or a fusion protein thereof with GST is immunized to small animals such as rabbit to obtain serum. The polyclonal antibody may be prepared by purifying the serum through ammonium sulfate precipitation, protein A or protein G column, DEAE ion exchange chromatography, or affinity column, wherein the polypeptide of the present invention is coupled and such. On the other hand, a monoclonal antibody can be prepared as follows: A polypeptide of the present invention is administered to a small animal such as a mouse and the spleen is subsequently excised from the mouse and ground to separate cells. Then, the cells are fused with mouse myeloma cells using reagents such as polyethylene glycol or such, and clones that produce antibodies binding to the polypeptide of the present invention are selected from these fused cells (hybridoma). The obtained hybridoma is then transplanted into the peritoneal cavity of a mouse and ascites is collected from the mouse. The monoclonal antibodies can be prepared by purifying the ascite using, for example, ammonium sulfate precipitation; protein A or protein G column; DEAE ion exchange chromatography; affinity column wherein the polypeptides of the present invention are coupled; and such.

The antibodies of the present invention can be used for the isolation, identification and purification of the polypeptides of the present invention and cells expressing them.

The polypeptides of the present invention can be used to screen for candidate compounds for actin cytoskeleton-controlling agents. Actin cytoskeleton-controlling agents may be used as therapeutic agents for diseases associated with abnormal expression of a polypeptide of the present invention. Molecules to be identified may be naturally-occurring molecules as well as artificially synthesized structural or functional imitated molecules. The polypeptides of the present invention are believed to be related to various biological functions, including many pathologies. Thus, the detection of compounds that activate the polypeptides of the present invention and compounds that inhibit the activation of the polypeptides of the present invention is desired in the art.

The present invention provides methods of screening for candidate compounds for actin cytoskeleton-controlling agents.

According to the present invention, first, afadin or actinin is contacted with a candidate compound and a polypeptide of the present invention, and then, the binding activity of afadin or actinin to the polypeptide of the present invention is measured. Next, the compound that modifies (i.e., increases or suppresses) the above-mentioned binding activity, as compared with the binding activity without the test compound, is selected.

Compounds modifying the binding activity of a polypeptide of the present invention to afadin or actinin that are isolated by the above-mentioned screening method are expected to serve as therapeutic agents, for example, for heart diseases such as myocardiac infarction and myocarditis. Moreover, the compounds can be further subjected to the above-mentioned screening method of the present invention as test compounds.

The binding activity as described above can be appropriately measured by methods well known in the art, such as the yeast two-hybrid system. There is no limitation on the test compounds; various known compounds and peptides (for example, those registered in the Chemical File); and random peptide groups that can be produced by utilizing the phage-display method (J. Mol. Biol. 1991, 222: 301-310) may be utilized. Furthermore, culture supernatants of microorganisms, natural components derived from plants and marine organisms and such can be used as the test compound of the screening method of the present invention. Moreover, extracts from biotic tissues, extracted solutions from cells, expression products of gene libraries and such can be also mentioned as samples to be tested, though the invention is not limited thereto.

The present invention also relates to methods for assessing and/or diagnosing diseases related to abnormal expression of the genes encoding the polypeptides of the present invention. The polypeptides of the present invention are considered to have important functions in vivo, and thus, abnormal expression thereof may cause various diseases.

Therefore, assay of diseases may be accomplished using expression of the polypeptides of the present invention as an index.

The phrase "assay of diseases" includes not only tests to draft therapeutic strategy for a subject who exhibits the symptom of a disease, but also tests for preventing diseases by determining whether the subject is susceptible to the disease or tests for determining whether the subject is already affected to the disease or not.

Considering the fact that ADIPs strongly express at the intercalated disc of cardiac muscle cells, abnormal expression of ADIP may cause heart diseases. Therefore, a disease of the present invention typically includes heart diseases including, more specifically, but not limited to, myocardiac infarction and myocaroditis.

One embodiment of the test methods of the present invention is a method comprising the step of detecting, in a subject, mutation of a gene encoding a polypeptide of the present invention or in the expression control regions thereof.

More specifically, the test method of the present invention can be accomplished by directly determining the nucleotide sequence of a gene encoding a polypeptide of the present invention or its expression control region in a subject. According to this method, first, a DNA sample is prepared from a subject. The DNA sample can be prepared from chromosomal DNA or RNA extracted from cells of the subject, for example, cardiac muscle cells. In order to prepare a DNA sample for the present method from a chromosomal DNA, a genomic library may be produced by, for example, digesting the chromosomal DNA with appropriate restriction enzymes, and then cloning the digested DNA into a vector. On the other hand, for example, a cDNA library may be prepared from RNA using reverse transcriptase to prepare a DNA sample for the present method. Next, DNA containing a gene encoding a polypeptide of the present invention or the expression control region thereof is isolated according to the present method. The isolation of a DNA can be carried out by screening the genomic library or cDNA library, using probes hybridizing with the DNA containing the gene encoding the polypeptide of the present invention or its expression control region. The isolation of a DNA can be also carried out by PCR using the genomic DNA library, cDNA library or RNA as the template, and primers hybridizing to a DNA containing a gene encoding a polypeptide of the present invention or its expression control region. Then, the nucleotide sequence of the isolated DNA is determined according to the present method. The determination of the nucleotide sequence of selected DNAs can be carried out by methods known to those skilled in the art. According to the present method, the determined nucleotide sequence of the DNA is then compared with a control. The "control" as used herein refers to a nucleotide sequence of DNAs containing a gene encoding a normal (wild type) polypeptide of the present invention or its expression control region. When the nucleotide sequence of the DNA of a subject differs from those of the control as a result of the comparison above, the subject is judged to be affected with disease or is in danger of developing the disease. Alternatively, the "control" may be the nucleotide sequences of genes encoding a polypeptide of the present invention derived from a patient of a heart disease, such as myocardiac infarction and myocaroditis. In this case, when the nucleotide sequence of the DNA of a subject is determined to be the same as those of the control, the subject is judged to be affected with the disease or is in danger of developing the disease. Furthermore, the "control" does not have to be one nucleotide sequence of a subject, but may be an assembly of multiple nucleotide sequences.

According to the test method of the present invention, various methods can be used other than the method of directly determining the nucleotide sequence of a DNA derived from a subject as described above.

In one embodiment of the present method, first, a DNA sample is prepared from a subject and digested with restriction enzymes. Then, the DNA fragments are separated in accordance with their size, followed by comparison of the detected sizes of the DNA fragments with those of a control. Alternatively, in another embodiment, a DNA sample is first prepared from a subject. Then, DNA containing a gene encoding a polypeptide of the present invention or its expression control region is amplified from the sample, and the amplified DNAs are digested with restriction enzymes. After separating the DNA fragments according to their size, the detected sizes of the DNA fragments are compared with those of a control.

Such methods include a method utilizing the Restriction Fragment Length Polymorphism/RFLP and the PCR-RFLP method. Specifically, when variations exist for the recognition sites of a restriction enzyme, or when insertion(s) or deletion(s) of base(s) exists in a DNA fragment generated by a restriction enzyme treatment, the sizes of fragments that are generated after the restriction enzyme treatment vary in comparison with those of a control. The portion containing the mutation is amplified by PCR, and then, is treated with respective restriction enzymes to detect these mutations as a difference in the mobility of bands after electrophoresis. Alternatively, the presence or absence of mutations can be detected by carrying out Southern blotting with a probe DNA of the present invention after treating the chromosomal DNA with respective restriction enzymes followed by electrophoresis. The restriction enzymes to be used can be appropriately selected in accordance with respective mutations. The Southern blotting can be conducted not only on the genomic DNA but also on cDNAs directly digested with restriction enzymes, wherein the cDNAs are converted by the use of a reverse transcriptase from RNAs prepared from subjects. Alternatively, after amplifying DNAs containing a gene encoding a polypeptide of the present invention or its expression control region by PCR using the cDNA as a template, the cDNAs are digested with restriction enzymes and the difference of mobility on an electrophoresis gel of DNA fragments generated by the digestion are examined.

In another embodiment of the present method, a DNA sample is first prepared from a subject. Then, a DNA containing a gene encoding a polypeptide of the present invention or its expression control region is amplified. Thereafter, the amplified DNA is dissociated into single strand DNAS, and the single strand DNAs are separated on a non-denaturing gel. The mobility of the separated single strand DNAs on the gel is compared with those of a control.

Such methods include, for example, the PCR-SSCP (single-strand conformation polymorphism) method ("Cloning and polymerase chain reaction-single-strand conformation polymorphism analysis of anonymous Alu repeats on chromosome 11." Genomics 1992, Jan. 1, 12(1): 139-146; "Detection of p53 gene mutations in human brain tumors by single-strand conformation polymorphism analysis of polymerase chain reaction products." Oncogene 1991, Aug. 1, 6(8): 1313-1318). This method is particularly preferable for screening many DNA samples, since it has advantages such as: comparative simplicity of operation; and small amount of a test sample required. The principle of the method is as follows. A single strand DNA dissociated from a double-strand DNA fragment forms a unique higher conformation depending on respective nucleotide sequence. Complementary single-stranded DNAs having the same chain length of the dissociated DNA strand shift to different positions in accordance with the difference of the respective higher conformations after electrophoresis on a polyacrylamide gel without a denaturant. The higher conformation of a single-stranded DNA changes even by a substitution of one base, which change results in a different mobility by polyacrylamide gel electrophoresis. Accordingly, the presence of a mutation in a DNA fragment due to point mutation, deletion, insertion and such can be detected by detecting the change in mobility.

More specifically, DNA containing a gene encoding a polypeptide of the present invention (or its expression control region) is first amplified by PCR and such. Preferably, a DNA of a length of about 200 bp to 400 bp is amplified. Those skilled in the art can appropriately select the condition and such for the PCR. DNA products amplified by PCR can be labeled using primers labeled with isotopes such as $^{32}P$, fluorescent dyes and biotin. Alternatively, the amplified DNA products can be also labeled by conducting PCR in a reaction solution containing substrate bases labeled with isotopes such as $^{32}P$, fluorescent dyes and biotin. Furthermore, the labeling can be also carried out by adding substrate bases labeled with an isotope such as $^{32}P$, fluorescent dyes and biotin, to the amplified DNA fragment using Klenow enzyme and such, after the PCR reaction. Then, the obtained labeled DNA fragments are denatured by heating and such, and electrophoresis is carried out on a polyacrylamide gel without denaturant such as urea. The condition for the separation of the DNA fragments by this electrophoresis can be improved by adding appropriate amounts (about 5% to 10%) of glycerol to the polyacrylamide gel. Furthermore, although the condition for electrophoresis varies depending on the property of respective DNA fragments, it is usually carried out at room temperature (20° C. to 25° C.). When a preferable separation can not be achieved at this temperature, a temperature at which optimum mobility can be achieved is searched from temperatures between 4° C. to 30° C. The mobility of the DNA fragments is detected by autoradiography with X-ray films, scanner for detecting fluorescence and such, after the electrophoresis to analyze the result. When a band with different mobility is detected, the presence of a mutation can be confirmed by directly excising the band from the gel, amplifying it again by PCR, and directly sequencing the amplified fragment. The bands can be also detected by staining the gel after electrophoresis with ethidium bromide, silver and such, without using labeled DNAs.

In still another method, a DNA sample is first prepared from a subject. DNA containing a gene encoding a polypeptide of the present invention or its expression control region is amplified, and then, the amplified DNAs are separated on a gel with gradient concentration of a DNA denaturant. The mobilities of the separated DNAs on the gel are compared with those of a control.

The denaturant gradient gel electrophoresis method (DGGE method) can be exemplified as such methods. The DGGE method comprises the steps of: (1) electrophoresing the mixture of DNA fragments on a polyacrylamide gel with gradient concentration of denaturant; and (2) separating the DNA fragments in accordance with the difference of instabilities of respective fragments. When DNA fragments containing mismatches shift to a part with a certain concentration of the denaturant on the gel, the DNA fragments partly dissociate to single-strand near the mismatches due to the instability of the DNA sequence. The mobility of the partly-dissociated DNA fragment becomes remarkably slow giving a difference in mobility compared to that of perfectly double-stranded DNAs without dissociated parts, which allows separation of these DNAs. Specifically, DNA containing a gene encoding a polypeptide of the present invention or its expression control region is (1) amplified by PCR and such with a primer of the present invention and such; (2) electrophoresed on a polyacrylamide gel with gradient concentration of denaturant such as urea; and (3) the result is compared with a control. The presence or absence of a mutation can be detected by detecting the difference of mobility of the DNA fragment due to the extreme slowed down mobility speed of the fragment by separation into single-stranded DNAs of a DNA fragment with mutations at parts of the gel where the concentration of the denaturant is lower.

In addition to the above-mentioned methods, the Allele Specific Oligonucleotide (ASO) hybridization method can be used to detect mutations only at specific sites. When an oligonucleotide with a nucleotide sequence expected to contain a mutation is prepared and is subjected to hybridization with a DNA sample, the efficiency of hybridization is reduced by the existence of the mutation. The decrease can be detected by the Southern blotting method; methods which utilize a specific fluorescent reagent that have a characteristic to quench by intercalation into the gap of the hybrid; and such. Furthermore, the detection may be also conducted by the ribonuclease A mismatch truncation method. Specifically, DNA containing a gene encoding a polypeptide of the present invention is amplified by PCR and such, and the amplified DNAs are hybridized with labeled RNAs, which were prepared from a control cDNA and such to incorporate them into a plasmid vector and such. The presence of a mutation can be detected with autoradiography and such, after cleaving those sites that form a single-stranded conformation due to the existence of a mutation with ribonuclease A.

Another embodiment of the test method of the present invention includes a method comprising the step of detecting the expression level of a gene encoding a polypeptide of the present invention. Herein, transcription and translation are included in the meaning of the phrase "expression of a gene". Accordingly, mRNAs and proteins are included in the phrase "expression product".

In a preferred embodiment, the present invention provides methods for assaying a cardiac disease which comprises the step of detecting the expression level of the gene encoding the polypeptide of the present invention in the test subject.

The method as described above may comprise the steps of: (i) preparing an RNA sample from cells (for example, cardiac muscle cells) of a subject; (ii) measuring the amount of RNA encoding the polypeptide of the present invention in the sample; and (iii) comparing the measured amount of the RNA with a control.

A Northern blotting method using a probe which hybridizes with the polynucleotide encoding a polypeptide of the present invention; an RT-PCR method using a primer which hybridizes with a polynucleotide encoding the polypeptide of the present invention; and such can be exemplified as such methods.

Furthermore, a DNA array (Masami Muramatsu and Masashi Yamamoto, New Genetic Engineering Handbook, YODOSHA Co., LTD., 280-284) can also be utilized in the testing for the transcription level of the gene encoding the polypeptide of the present invention. Specifically, first, a cDNA sample prepared from a subject and a basal plate on which polynucleotide probes hybridizing with the polynucleotides encoding the polypeptides of the present invention are fixed are provided. Plural kinds of polynucleotide probes can be fixed on the basal plate in order to detect plural kinds of polynucleotides encoding the polypeptides of the present invention. Preparation of a cDNA sample from a subject can be carried out by methods well known to those skilled in the art. In a preferable embodiment for the preparation of the cDNA sample, first, total RNAs are extracted from a cell of a subject. Examples of cells include the cardiac muscle cells. The extraction of total RNAs can be carried out, for example, as follows. So long as total RNAs with high purity can be prepared, known methods, kits and such can be used. Then, the cDNA sample is prepared by synthesizing cDNAs with reverse transcriptase using extracted total RNAs as a template. The synthesis of cDNA from total RNAs can be carried out by conventional methods known in the art. The prepared cDNA sample is labeled for detection according to needs. The labeling substance is not specifically limited so long as it can be detected, and include, for example, fluorescent substances and radioactive elements. The labeling can be carried out by conventional methods (L. Luo et al., "Gene expression profiles of laser-captured adjacent neuronal subtypes", Nat. Med. 1999, 117-122).

In the method wherein the expression level of the gene encoding the polypeptide of the present invention in the test subject is detected, the term "control" usually refers to the amount of RNA, encoding polypeptides of the present invention, in the RNA sample obtained from cardiac muscle cells of a healthy individual.

When a significantly altered expression level of RNA encoding the polypeptide of the present invention compared with control is detected by the method, the test subject is judged as being affected with a heart disease associated with abnormal expression of the gene, or is at risk of developing the disease. Moreover, for a test subject who is already known to be affected with a heart disease, the disease is judged as being caused by a change in the expression level of RNA encoding the polypeptide.

Moreover, the test method of the present invention can be conducted as follows by measuring the protein expression level in cells (for example, cardiac muscle cells) of the test subject. First, protein samples are obtained from cells of a test subject. Second, the amount of a polypeptide of the present invention present in the protein samples is measured. Third, the amount of the polypeptide is compared with control.

Such methods include SDS polyacrylamide electrophoresis method, and methods using antibodies that bind to a protein of the present invention such as Western blotting method, Dot blotting method, Immunoprecipitation method, Enzyme-linked immunosorbent assay (ELISA) and Immunofluorescence method.

When significantly altered expression level of a protein encoded by a polynucleotide of the present invention is detected compared with the control, a test subject is judged as being at a risk of developing heart disease (high risk) or already affected with heart disease. Moreover, for a test subject who is already known to be affected with a heart disease, the disease is judged as being caused by the change in the expression level of the polynucleotide as described above.

The present inventors provided a novel afadin DIL domain-binding protein (ADIP) and gene encoding the protein. The protein of the present invention is expected to be useful for evaluating agents which can control actin cytoskeletons.

The protein of the present invention is very highly expressed at the intercalate disc of cardiac muscle cells. Therefore, the protein of the present invention is contemplated as being useful as a functional marker of the intercalate disc for heart diseases, such as myocardial infarction and myocarditis. Heart diseases may be diagnosed by considering the expression level of the gene of the present invention as an indicator. Moreover, the protein of the present invention is useful for screening candidate compounds for agents to treat heart diseases.

EXAMPLES

Herein below, the present invention will be specifically described using Examples, however, it is not to be construed as being limited thereto.

Example 1

Construction of Expression Vectors

Mammalian expression vectors, pCMV-FLAG, pCMV-T7 and pCMV-HA, were designed to express N-terminal FLAG-, T7- and HA-tagged proteins, respectively (G. Takaesu, S. Kishida, A. Hiyama, K. Yamaguchi, H. Shibuya, K. Irie, J. Ninomiya-Tsuji and K. Matsumoto, "TAB2, a novel adaptor protein, mediates activation of TAK1 MAP-KKK by linking TAK1 to TRAF6 in the IL-1 signal transduction pathway." Mol. Cell 2000, 5: 649-658).

The mammalian expression vector expressing the DIL domain (amino acids (aa) 606-983) of afadin was constructed using pCMV-T7.

The mammalian expression vectors pCMV-HA-mADIP (aa 1-615), pCMV-HA-rADIP-C (aa 159-613), pCMV-HA-mADIP-C (aa 339-615), pCMV-FLAG-mADIP-C (aa 339-615) and pCMV-FLAG-mADIP-M (aa 152-436), expressing mouse ADIP (mADIP) and rat ADIP (rADIP), were constructed using pCMV-FLAG or pCMV-HA.

The mammalian expression vector, pCMV-HA-α-actinin-1-C (aa 406-892), expressing α-actinin-1 (human, BC015766; GenBank) was constructed using pCMV-HA.

Glutathione S-transferase (GST) fusion or maltose-binding protein (MBP) fusion vectors of mADIP and rADIP, MBP-MADIP (aa 1-615), MBP-rADIP-C (aa 159-613), MBP-mADIP-C (aa 339-615), GST-rADIP-C (aa 159-613), GST-mADIP-N (aa 1-226) and GST-mADIP-C (aa 339-615), were constructed using pGEX-KG (K. L. Guan and J. E. Dixon, "Eukaryotic protein expressed in *Escherichia coli*: an improved thrombin cleavage and purification procedure of fusion proteins with glutathione S-transferase." Anal. Biochem. 1991, 192: 262-267) or pMal-C2 (New England Biolabs).

Example 2

Preparation of Antibody

GST fusion proteins of fragments of rADIP C-terminus (aa 159-613; rADIP), mADIP N-terminus (aa 1-226; mADIP-N) and mADIP C-terminus (aa 339-615; mADIP-C) were produced in *Escherichia coli*, purified and then each of the proteins were used as an antigen to raise rabbit pAb.

Two pAbs against rADIP-C and mADIP-C, M05 and M01, were used after affinity purification with MBP-rA- DIP-C (aa 159-613) and MBP-mADIP-C (aa 339-615), respectively. Another pAb against mADIP-N, M57, was used after affinity purification with GST-MADIP-N (aa 1-226).

GST- and MBP-fusion proteins were purified with glutathione-sepharose beads (Amersham-Pharmacia Biotech) and amylose resin beads (New England Biolabs), respectively.

A mouse anti-afadin mAb was prepared according to the literature (T. Sakisaka, H. Nakanishi, K. Takahashi, K. Mandai, M. Miyahara, A. Satoh, K. Takaishi, and Y. Takai, "Different behavior of l-afadin and neurabin-II during the formation and destruction of cell-cell adherens junction." Oncogene 1999, 18: 1609-1617).

Rat anti-E-cadherin mAb (ECCD2) was described by A. Nagafuchi et al. (A. Nagafuchi, Y. Shirayoshi, K. Okazaki, K. Yasuda, and M. Takeichi, "Transformation of cell adhesion properties by exogenously introduced E-cadherin cDNA.", Nature, 1987, 329(6137): 341-3) and Y. Shirayoshi et al. (Y. Shirayoshi, T. S. Okada, and M. Takeichi, "The calcium-dependent cell-cell adhesion system regulates inner cell mass formation and cell surface polarization in early mouse development.", Cell, 1983, 35(3 Pt 2): 631-8.). Mouse anti-ZO-1 mAb was purchased from Chemicon. Mouse anti-α-actinin, anti-vinculin and anti-FLAG-M2 mAbs were purchased from Sigma Chemicals. Rabbit anti-α-actinin pAb was purchased from Santa Cruz. Mouse anti-T7 mAb was purchased from Novagen.

Example 3

Cell Culture and Protein Concentration

HEK293, MDCK, nectin-2α-L and nectin-2α-AC-L cells were cultured in Dulbecco's modified Eagle medium (DMEM) containing 10% fetal calf serum.

Protein concentration was determined using bovine serum albumin as the protein standard (M. M. Bradford, "A rapid and sensitive method for the quantitation of microgram quantities of protein utilizing the principle of protein-dye binding." Anal. Biochem. 1976, 72: 248-254).

Example 4

Identification of Afadin-binding Protein

The present inventors performed yeast two-hybrid screening to identify an afadin-binding protein using a region of afadin containing the DIL domain (aa 606-983) as a bait. A schematic structure of afadin is shown in FIG. 1A.

The bait vector, pGBDU-afadin (aa 511-981), was constructed by subcloning an insert encoding the amino acid residues of afadin into pGBDU-C1 (P. James, J. Hallady and E. A. Craig, "Genomic Libraries and a host strain designed for highly efficient two-hybrid selection in yeast." Genetics 1996, 144: 1425-1436).

Yeast two-hybrid libraries constructed from cDNAs derived from 11-days old mouse embryo, rat brain, rat lung and human testis were purchased from Clontech.

Two-hybrid screening using the yeast strain PJ69-4A (MATa trp1-901 leu2-3, 112 ura3-52 his3-200 gal4Δ gal80Δ GAL2-ADE2 LYS2::GAL1-HIS3 met2::GAL7-lacZ) was performed as described in the literature (P. James, J. Hallady and E. A. Craig, "Genomic Libraries and a host strain designed for highly efficient two-hybrid selection in yeast." Genetics 1996, 144: 1425-1436). Standard procedures for yeast manipulation were performed as described in the literature (C. A. Kaiser, A. Adams and D. E. Gottschling, Methods in Yeast Genetics, Cold Spring Harbor Laboratory Press, N.Y., 1994).

As a result, the present inventors screened $2 \times 10^5$ clones of a mouse embryo library and $2 \times 10^5$ clones of a rat brain library and obtained 31 and 25 positive clones, respectively. Four mouse clones and one rat clone encoded proteins similar to the carboxy-terminal portion of human KIAA0923 (AB023140; GenBank/EMBL/DDBJ). The two-hybrid analysis revealed that ADIP specifically binds to the DIL domain of afadin but not to the DIL domain of yeast Myo4 (FIG. 1B). Moreover, yeast transformants with the indicated plasmids were streaked on synthetic complete medium lacking histidine and then incubated for 3 days at 30° C. to score HIS3 reporter activity.

Figure 2:
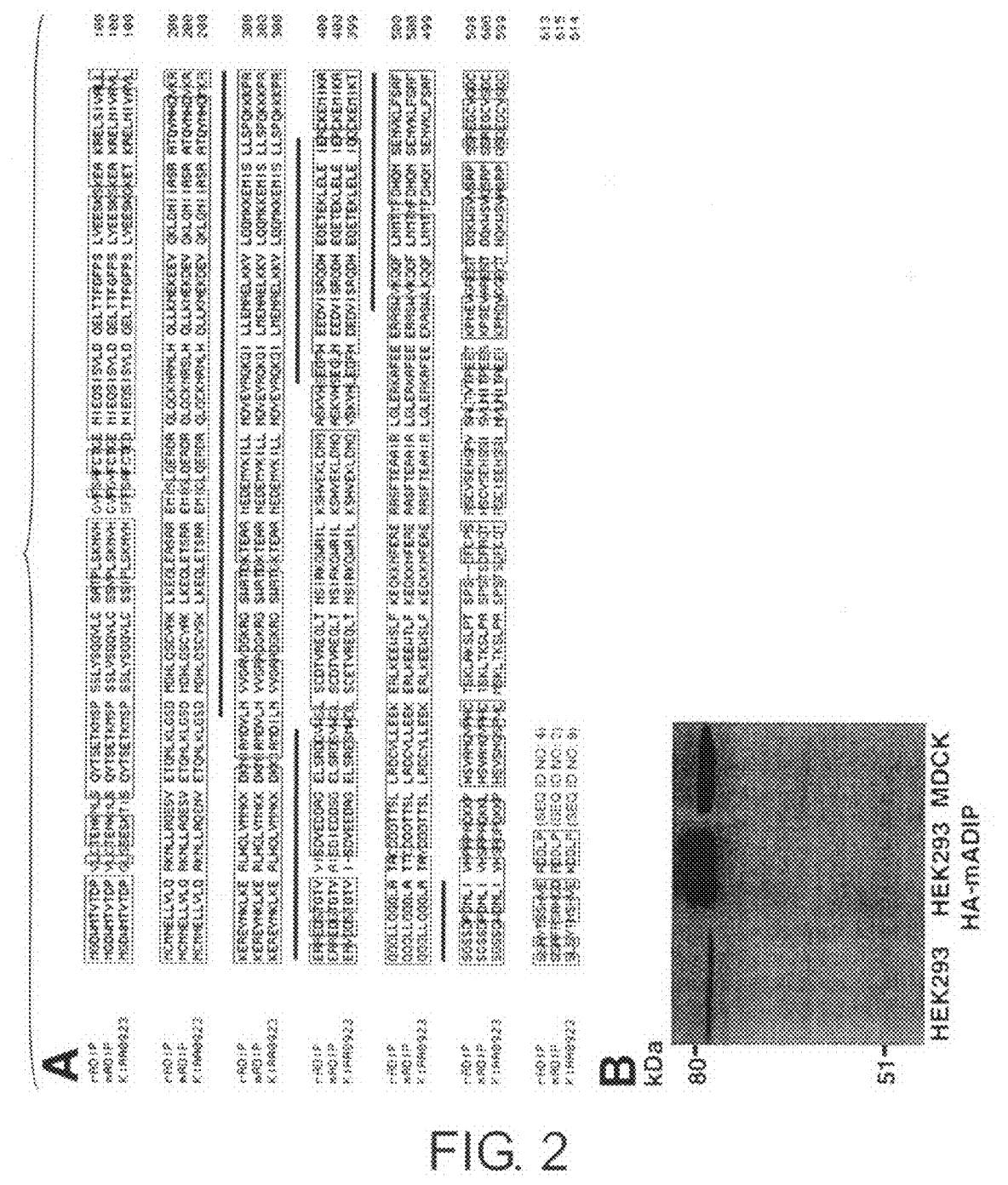
Figure 3:
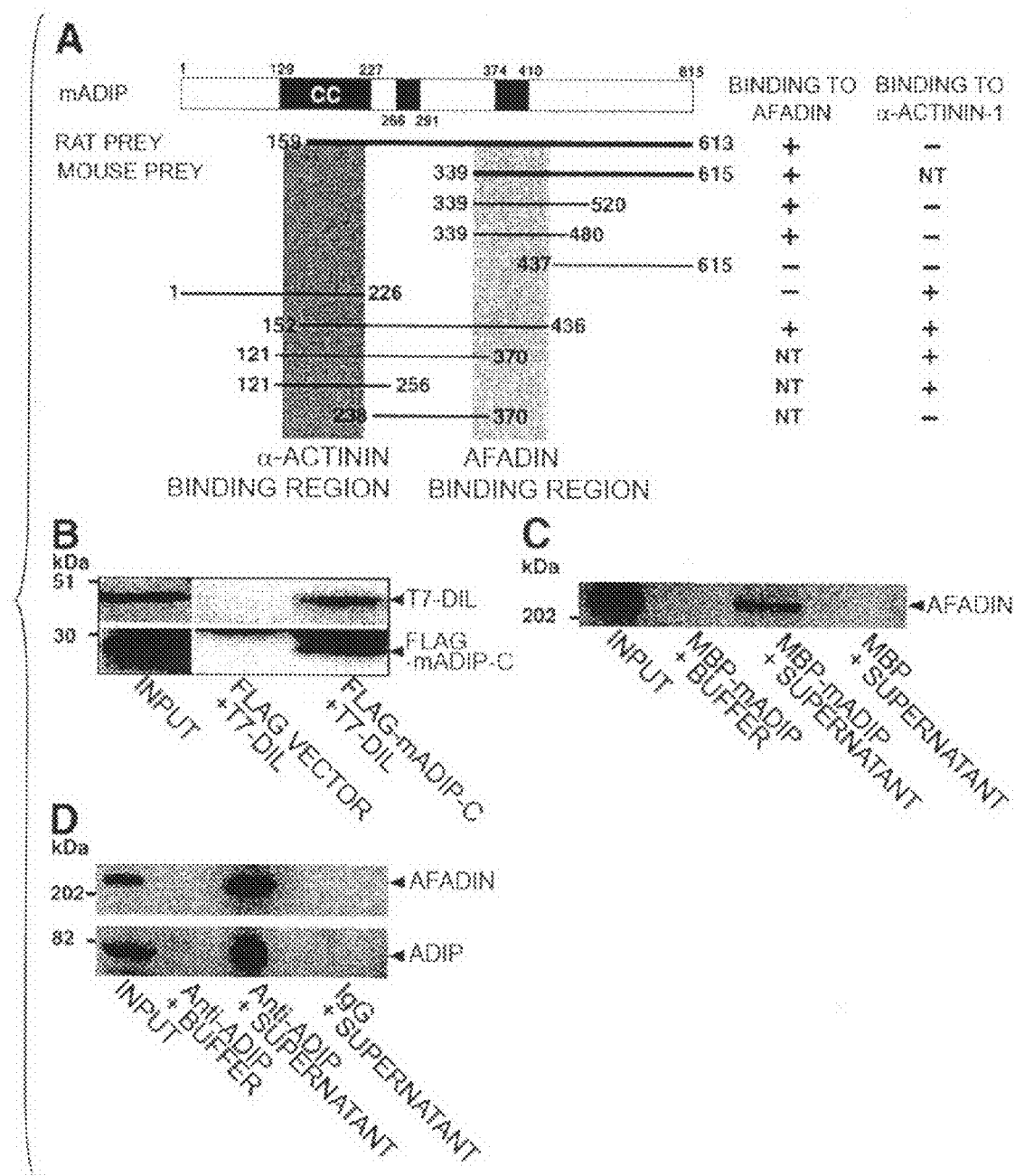
FIG. 3 depicts the in vitro and in vivo binding of ADIP to afadin.

The present inventors dubbed this protein afadin DIL domain-interacting protein (ADIP). ADIP has three coiled-coil domains and the region containing the third coiled-coil domain (aa 339-480) of ADIP was essential for the binding with the DIL domain of afadin (FIGS. 2A and 3A).

Example 5

Full-length cDNAs of Mouse ADIP and Rat ADIP

For full-length cDNAs of mouse and rat ADIPs, BLAST searches were conducted against GenBank and EMBL databases. A selection of hits obtained by BLAST searches against the human subset of GenBank and EMBL sequences was used to assemble the cDNA sequence of the human homologue of KIAA0923 (AB023140; GenBank/EMBL/DDBJ). A cDNA of KIAA0923 was described by T. Nagase et al. (T. Nagase, K. Ishikawa, M. Suyama, R. Kikuno, M. Hirosawa, N. Miyajima, A. Tanaka, H. Kotani, N. Nomura, and O. Ohara, "Prediction of the coding sequences of unidentified human genes. XIII. The complete sequences of 100 new cDNA clones from brain which code for large proteins in vitro.", DNA Res., 6 (1), 63-70 (1999).

Full-length cDNAs of mADIP (accession number: AF532969) and rADIP (accession number: AF532970) were prepared from mouse and rat brain cDNAs (Clontech), respectively, by reverse-transcriptase-PCR using the following primer sets: for MADIP cDNA, 5'-CGTAGGAGAGT-GACAGGAGCTG-3' (SEQ ID NO: 5) and 5'-GGTTATC-GAGTTTTTCTACATGAC-3 (SEQ ID NO: 6); and for rADIP cDNA, 5'-CGTAGGAGAGTGACAGGAGCTG-3' (SEQ ID NO: 7) and 5'-TTCCTGTTTTTGCACTG-TAGCTG-3' (SEQ ID NO: 8).

The PCR products were subcloned into pCR4B (Invitrogen) to perform nucleotide sequence analysis according to the dideoxynucleotide termination method using a DNA sequencer (model 3100; Applied Biosystems, Inc.).

The full-length clones of these mouse and rat cDNAs encoded proteins composed of 615 aa with a calculated molecular weight of 70,954 Da, and 613 aa with a calculated molecular weight of 70,684 Da, respectively (FIG. 2A).

The aa sequences of mouse ADIP (mADIP) and rat ADIP (rADIP) were 92% identical to each other and 88% and 87% identical to that of human KIAA0923, respectively (FIG. 2A).

Example 6

Transfection

To confirm whether the isolated cDNAs encode a full-length ADIP, HEK293 cells were transfected with pCMV- HA-mADIP, expressing hemoagglutinin (HA)-tagged full-length mADIP. The transfection was conducted using CalPhos mammalian transfection kit (Clontech). Cell extracts from MDCK and HEK293 were subjected to SDS-polyacrylamide gel electrophoresis (PAGE). SDS-PAGE was performed as described by Laemmli (U. K. Laemmli, "Cleavage of structural proteins during the assembly of the head of bacteriophage T4." Nature 1970, 227: 680-685). Western blotting with three anti-ADIP pAb (M57, M01 and M05; anti-ADIP polyclonal antibodies (pAbs)) was then performed.

As a result, a protein with a molecular weight of approximately 78 kDa was detected in the extracts of HEK293 cells expressing HA-mADIP (FIG. 2B).

Therefore, the present inventors concluded that the isolated cDNA encodes the full-length ADIP.

Example 7

Identification of ADIP Function: Binding to α-actinin

To gain insight into the function of ADIP, the present inventors attempted to identify ADIP-binding protein(s). As described above, the ADIP has three coiled-coil domains and the region containing the third coiled-coil domain (aa 339-480) of the ADIP is required for the binding to the DIL domain of afadin.

The present inventors performed yeast two-hybrid screening using a region of the ADIP containing all three coiled-coil domains (aa 152-436) as baits. One bait vector, pGBD-mADIP-B (aa 152-436), was constructed by subcloning an insert encoding the aa residues of mADIP into pGBD-C1 (P. James, J. Hallady and E. A. Craig., "Genomic libraries and a host strain designed for highly efficient two-hybrid selection in yeast." Genetics 1996, 144: 1425-1436).

The present inventors screened $7 \times 10^5$ clones derived from a rat lung library and obtained 18 positive clones. Nine clones encoded the C terminus of α-actinin-1 (human, BC015766; GenBank). α-Actinin is a well-characterized protein that shows F-actin-crosslinking activity (K. Burridge and J. R. Feramisco, "Non-muscle alpha actinins are calcium-sensitive actin-binding proteins." Nature 1981, 294: 565-567). Four isoforms of human α-actinin have been identified: non-muscle actinin-1 and -4, and muscle actinin-2 and -3 (D. B. Millake, A. D. Blanchard, B. Patel and D. R. Critchley, "The cDNA sequence of a human placental alpha-actinin." Nucleic Acids Res. 1989, 17: 6725; H. Youssoufian, M. McAfee and D. J. Kwiatowski, "Cloning and chromosomal localization of the human cytoskeletal alpha-actinin gene reveals linkage to the beta-spectrin gene." Am. J. Hum. Genet. 1990, 47: 62-71; A. H. Beggs, T. J. Byers, J. H. Knoll, F. M. Boyce, G. A. Bruns and L. M. Kunkel, "Cloning and characterization of two human skeletal muscle alpha-actinin genes located on chromosomes 1 and 11." J. Biol. Chem. 1992, 267: 9281-9288; K. Honda, T. Yamada, R. Endo, Y. Ino, M. Gotoh, H. Tsuda, Y. Yamada, H. Ciba and S. Hirohashi, "Actinin-4, a novel actin-bundling protein associated with cell motility and cancer invasion." J. Cell Biol. 1998, 140: 1383-1393).

Figure 9:
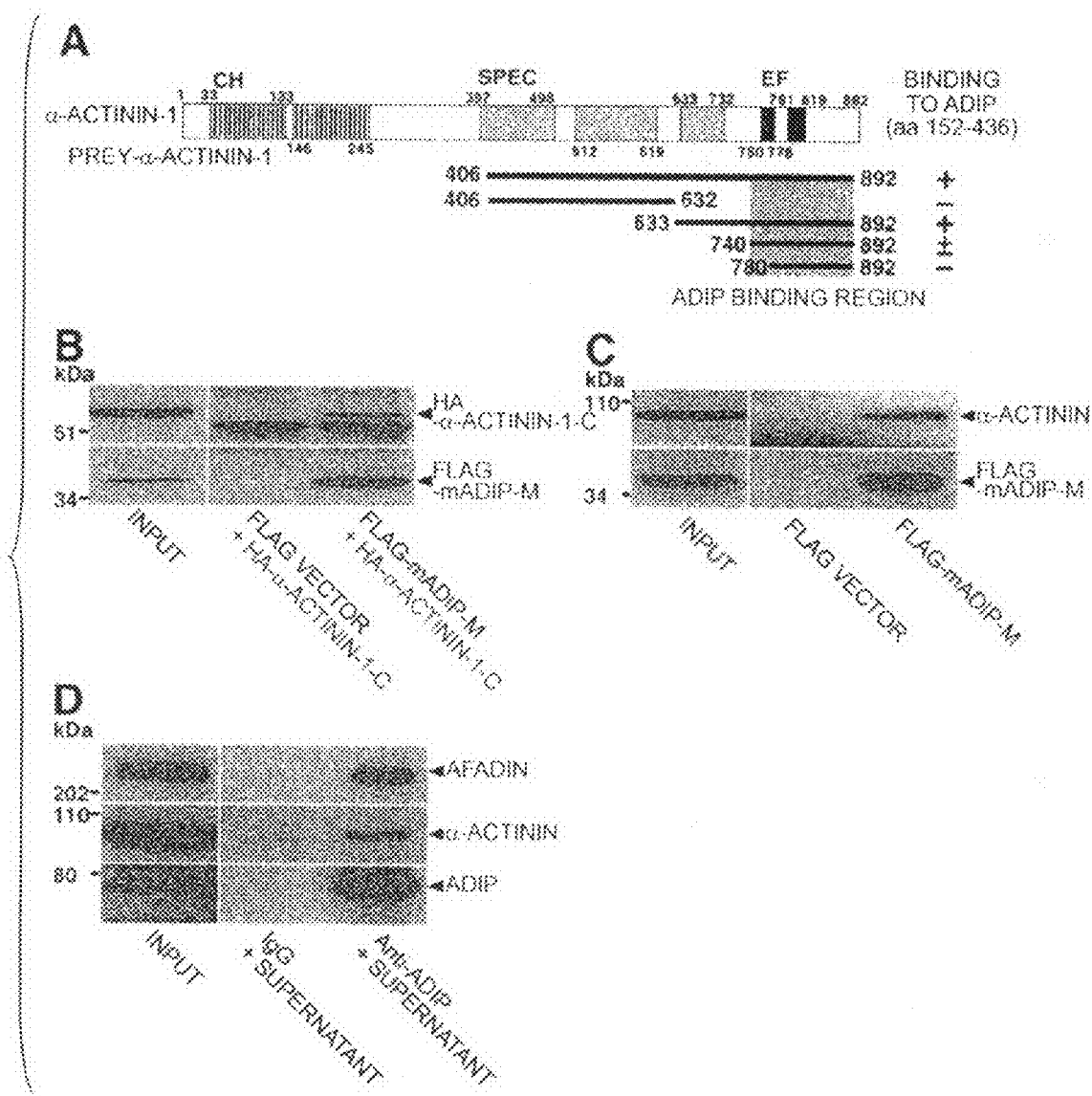
FIG. 9 depicts the in vivo binding of ADIP to α-actinin.

The present analysis suggested that ADIP binds to α-actinin-2 in addition to α-actinin-1 (data not shown), indicating that the binding of ADIP to α-actinin is not specific for α-actinin-1. The analysis also revealed that the region containing only the first coiled-coil domain (aa 1-226) of ADIP bound to α-actinin-1 (FIG. 3A) and that the two C-terminal EF-hand motifs of α-actinin-1 are necessary for its binding to ADIP (FIG. 9A).

These results indicate that the first coiled-coil domain of ADIP binds to the EF-hand motifs of α-actinin-1.

EXAMPLE 8

Immunoprecipitation and Affinity Chromatography

To further confirm the binding of ADIP to afadin in vivo and in vitro, the present inventors performed immunoprecipitation and affinity chromatography analyses.

Co-immunoprecipitation experiments using HEK293 cells were performed as follows: HEK293 cells were transfected with the expression plasmids in various combinations. The cells were suspended in 1 ml Buffer A (20 mM Tris-HCl, pH 7.5, 150 mM NaCl, 1% Triton X-100, 1 mM EDTA, 10 µM α-phenylmethanesulfonyl fluoride hydrochloride and 10 µg/ml aprotinin), sonicated for 10 s for three times at 10 s intervals and then incubated on ice for 30 min. A cell extract (1.2 mg protein) was obtained by centrifugation of the incubated cells at 100,000×g for 15 min, and the cell extract was pre-rinsed by incubation with protein G-Sepharose 4 Fast Flow beads (Amersham-Pharmacia Biotechnology). The cell extract was incubated with anti-FLAG M2 mAb (20 µl)-coated protein G-Sepharose 4 Fast Flow beads at 4° C. for 18 h. The beads were washed with Buffer A, followed by elution of the bound proteins by boiling the beads in SDS sample buffer (60 mM Tris-HCl, pH 6.7, 3% SDS, 2% 2-mercaptoethanol and 5% glycerol) for 10 min. The obtained sample was then subjected to SDS-PAGE, followed by Western blotting.

Co-immunoprecipitation experiments using MDCK cells were performed as follows: MDCK cells on two 10-cm dishes were sonicated in 2 ml Buffer A, followed by ultracentrifugation at 100,000×g for 15 min. The cell extract was pre-rinsed by incubation with protein A-Sepharose CL-4B beads (Amersham-Pharmacia Biotechnology) and then incubated with anti-ADIP pAb (M05) (20 µl)-coated protein A-Sepharose CL-4B beads at 4° C. for 18 h. After washing the beads in Buffer A, the bound proteins were eluted by boiling the beads in the SDS sample buffer for 10 min. The samples were then subjected to SDS-PAGE, followed by Western blotting.

Affinity chromatography using MDCK cells were carried out as follows: MDCK cells on two 10-cm dishes were sonicated in 2 ml Buffer A, followed by ultracentrifugation at 100,000×g for 15 min. The supernatant was incubated at 4° C. for 18 h with MBP or MBP-MADIP (200 pmol each) immobilized on 20 µl (wet volume) of amylose resin beads (New England Biolabs). After extensively washing the beads in Buffer A, the bound proteins were eluted with Buffer A containing 20 mM maltose. The eluents were boiled in SDS sample buffer. The samples were then subjected to SDS-PAGE, followed by Western blotting with anti-afadin mAb.

Co-immunoprecipitation of FLAG-tagged mADIP-C with the T7-tagged DIL domain of afadin was conducted. Expression vectors were transfected into HEK293 cells as indicated in FIG. 3B. The T7-tagged DIL domain of afadin specifically co-immunoprecipitated with the FLAG-tagged mADIP-C, as shown by Western blotting with anti-T7 and anti-FLAG mAbs.

Next, the extract of MDCK cells expressing endogenous afadin was incubated with MBP-fusion protein of the full-length mADIP (aa 1-615) immobilized on amylose-resin beads. After the beads were washed with lysis buffer, the bound proteins were eluted and the eluent was subjected to SDS-PAGE followed by Western blotting with anti-afadin mAb. Afadin indeed bound to MBP-mADIP, but not to singular MBP (FIG. 3C).

Finally, to confirm in vivo binding of ADIP to afadin, the present inventors examined the extract of MDCK cells whether endogenous afadin co-immunoprecipitates with endogenous ADIP. Endogenous afadin co-immunoprecipitated through the immunoprecipitation of endogenous ADIP in the extract of MDCK cells with anti-ADIP pAb (FIG. 3D). Afadin did not co-immunoprecipitate with control IgG. Two-hybrid analysis and these results as described above indicate that ADIP binds to afadin both in vivo and in vitro.

Example 10

Tissue and Subcellular Distribution of ADIP

Northern blotting was performed according to the literature (J. Sambrook, E. F. Fritsch and T. Maniatis, "Molecular Cloning: A Laboratory Manual, 2nd Edition." Cold Spring Harbor Laboratory Press, Cold Spring Harbor, N.Y., 1989, 7.1-7.87). mADIP cDNA fragment (bp 552-3194) was radiolabeled with [$\alpha$-$^{32}$P] by a standard random priming method and was used as a probe in mouse multiple tissue Northern blotting (Clontech).

Figure 4:
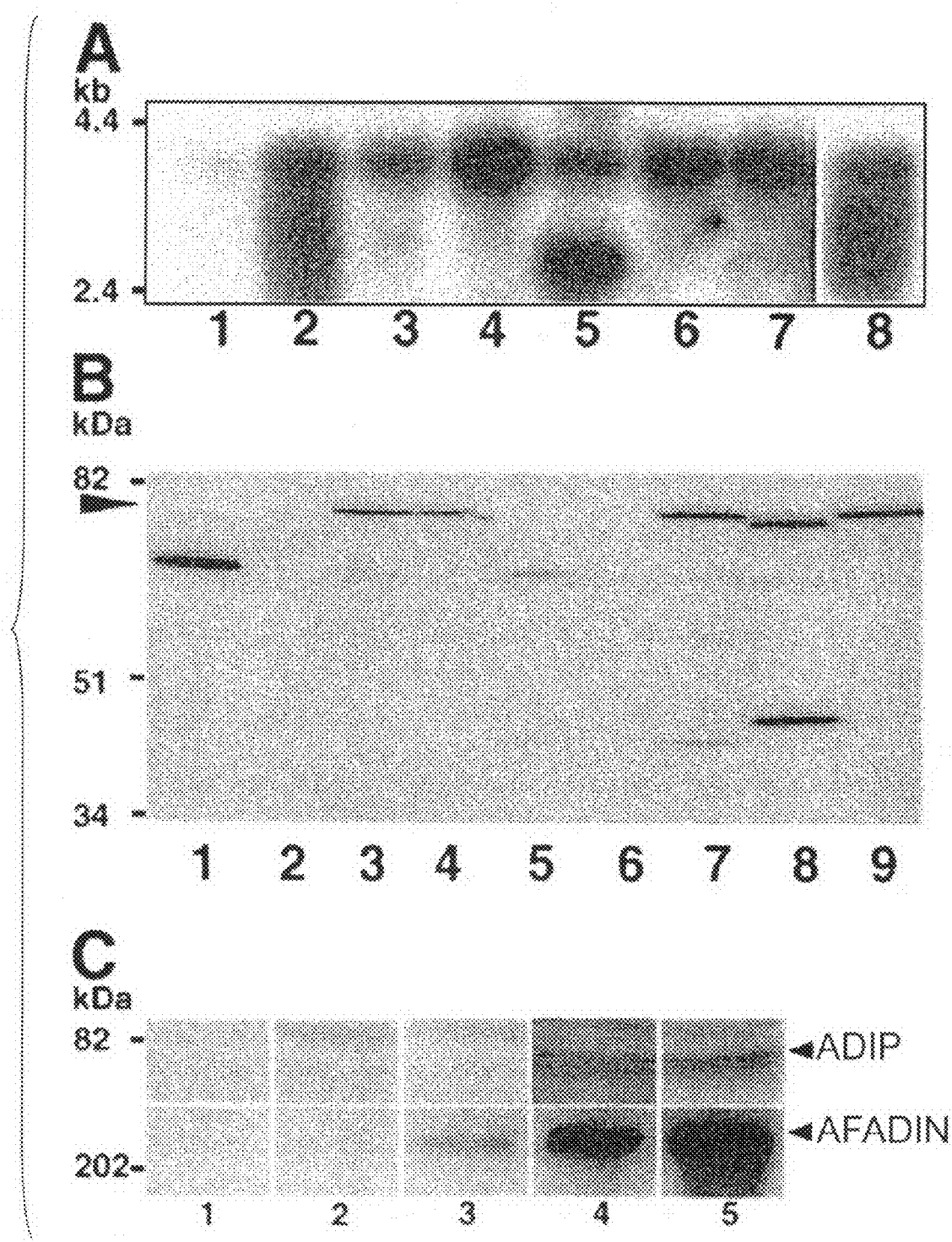
FIG. 4 depicts photographs showing tissue and subcellular distribution of ADIP.

The result detected ~4.3-kb mRNA in all the examined test mouse tissues, including heart, brain, spleen, lung, liver, skeletal muscle, kidney and testis (FIG. 4A). A smaller band (~3.0 kb) was also detected in the liver and the testis (FIG. 4A, lanes 5 and 8).

Homogenates of various mouse tissues (30 μg protein each) were subjected to SDS-PAGE (10% polyacrylamide gel), followed by Western blotting analysis with anti-ADIP pAb (M57). The result detected a ~78-kDa protein having the same size as ADIP detected in HEK293 and MDCK cells and in mouse spleen, lung and kidney (FIG. 4B, lanes 3, 4, 7 and 9). Smaller bands (~60 kDa in heart, ~76 and ~40 kDa in testis) were also detected, suggesting expression of smaller splice variants of ADIP (FIG. 4B, lanes 1 and 8).

Subcellular fractionation analysis of rat liver was performed as described in the literature (H. Kawabe, H. Nakanishi, M. Asada, A. Fukuhara, K. Morimoto, M. Takeuchi and Y. Takai, "Pilt, a novel peripheral membrane protein at tight junctions in endothelial cells." J. Biol. Chem. 2001, 276: 48350-48355). Each fraction (30 μg protein each) was subjected to SDS-PAGE (10% polyacrylamide gel), followed by Western blotting with anti-ADIP pAb (M57) or anti-afadin mAb. The results showed ADIP to be rich in the fractions of AJs and TJs which fraction was also abundant in afadin (FIG. 4C, lanes 4 and 5). The lack of detection of the ~78-kDa protein in the liver by the Western blotting analysis of tissue distribution of ADIP (FIG. 4B, lane 5) may be due to its low expression level.

These results indicate that ADIP is widely expressed, although its expression level varying depending on the tissue type.

Example 11

Co-localization of ADIP with Afadin at AJs in Epithelial Cells

Afadin has been shown to strictly localize at AJs undercoated with F-actin bundles (Mandai et al., J. Cell Biol. 1997, 139: 517-528). The present inventors examined the co-localization of ADIP with afadin at AJs in MDCK cells by immunofluorescence microscopy.

The immunofluorescence microscopy of mouse tissue culture and frozen sections thereof were performed as described in the literatures (K. Mandai, H. Nakanishi, A. Satoh, H. Obaishi, M. Wada, H. Nishioka, M. Itoh, A. Mizoguchi, T. Aoki, T. Fujimoto, Y. Matsuda, S. Tsukita and Y. Takai, "Afadin: A novel actin filament-binding protein with one PDZ domain localized at cadherin-based cell-to-cell adherens junction." J. Cell Biol. 1997, 139: 517-528; K. Takahashi, H. Nakanishi, M. Miyahara, K. Mandai, K. Satoh, A. Satoh, H. Nishioka, J. Aoki, A. Nomoto, A. Mizoguchi and Y. Takai, "Nectin/PRR: an immunoglobulin-like cell adhesion molecule recruited to cadherin-based adherens junctions through interaction with Afadin, a PDZ domain-containing protein." j. Cell Biol. 1999, 145: 539-549). Specifically, MDCK cells were double-stained with various combinations of anti-ADIP (M05), anti-afadin and anti-vinculin Abs.

Figure 5:
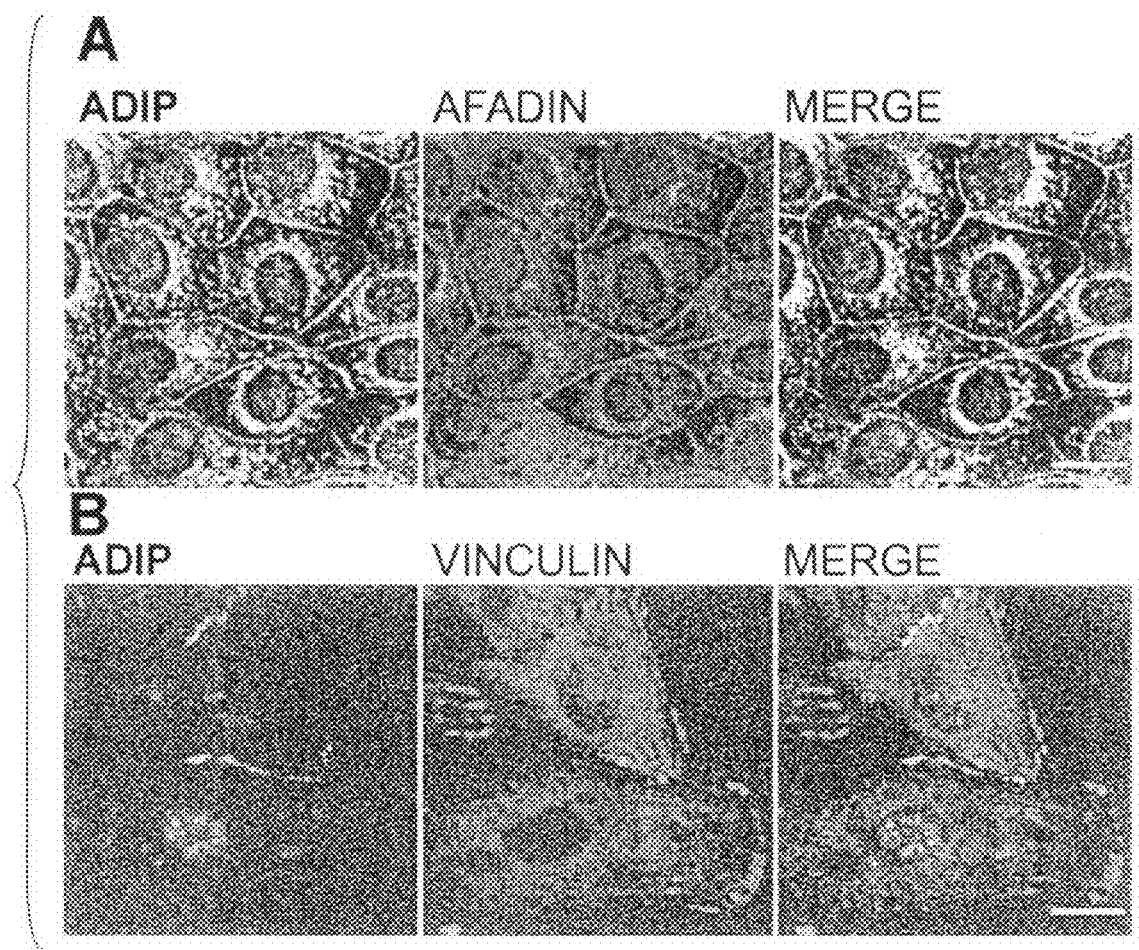
FIG. 5 depicts photographs showing localization of ADIP at AJs in MDCK cells. MDCK cells were double-stained with various combinations of anti-ADIP (M05), anti-afadin and anti-vinculin.

The results showed co-localization of ADIP and afadin at the cell-cell junctions (FIG. 5A). Substantially the same results were obtained with three anti-ADIP pAbs, M57, M01 and M05.

Moreover, ADIP was co-stained with Golgi 58 kDa protein, a marker for the Golgi complex. As a result, ADIP in the perinuclear region was stained at the Golgi complex (FIG. 5A).

Example 12

Comparison of ADIP and Endogenous Afadin Localizations

The present inventors established nectin-2α-L and nectin-2α-αC-L cell lines stably expressing HA-tagged ADIP (rADIP-C; aa 159-613) using LIPOFECTAMINE 2000 (Invitrogen) to confirm co-localization of ADIP and afadin.

Full-length nectin-2α (derived from nectin-2α-L cells) or nectin-2α lacking 4 amino acids at the C terminus (derived from nectin-2α-ΔC-L cells) were transiently expressed in cadherin defective L-cells that stably express afadin to compare the localization of expressed proteins with the localization of endogenous afadin. The full-length nectin-2α was able to bind to afadin, but the nectin-2α-ΔC failed to bind to afadin (K. Takahashi, H. Nakanishi, M. Miyahara, K. Mandai, K. Satoh, A. Satoh, H. Nishioka, J. Aoki, A. Nomoto, A. Mizoguchi and Y. Takai, "Nectin/PRR: an immunoglobulin-like cell adhesion molecule recruited to cadherin-based adherens junctions through interaction with Afadin, a PDZ domain-containing protein." J. Cell Biol. 1999, 145: 539-549).

The result revealed afadin to concentrate at the nectin-2α-based cell-cell adhesion sites in nectin-2α-L cells, consistent with the results shown in literatures (M. Miyahara, H. Nakanishi, K. Takahashi, K. Satoh-Horikawa, K. Tachibana and Y. Takai, "Interaction of nectin with afadin is necessary for its clustering at cell-cell contact sites but not for its cis dimerization or trans interaction." J. Biol. Chem. 2000, 275: 613-618; K. Tachibana, H. Nakanishi, K. Mandai, K. Ozaki, W. Ikeda, Y. Yamamoto, A. Nagafuchi, S. Tsukita and Y. Takai, "Two cell adhesion molecules, nectin and cadherin, interact through their cytoplasmic domain-associated proteins." J. Cell Biol. 2000, 150: 1161-1176). Moreover, the endogenously expressed HA-ADIP concentrated at nectin-2α-based cell-cell adhesion sites and co-localized with afadin in nectin-2α-L cells (FIG. 6A).

Figure 6:
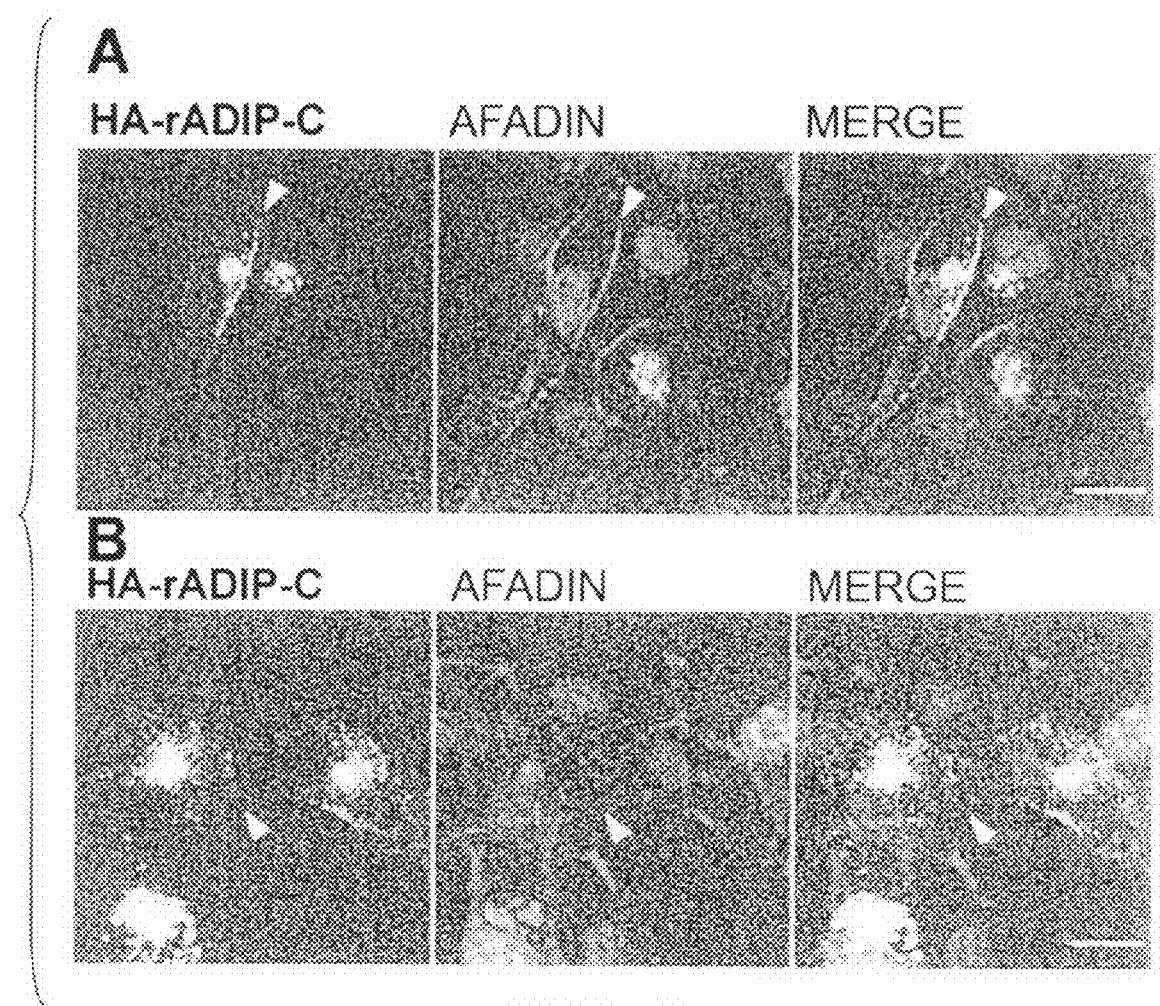
FIG. 6 depicts photographs showing co-localization of ADIP with afadin in nectin-2α-L cells.

However, the endogenously expressed HA-ADIP did not concentrated at the cell-cell adhesion site in nectin-2α-ΔC-L cells (FIG. 6B).

Example 13

Precise Localization of ADIP in the Junctional Complex Regions

To identify the precise localization of ADIP in the junctional complex regions, a frozen cross-section of mouse small intestine was triple-stained with anti-ADIP pAb, anti-afadin mAb and anti ZO-1 mAb. The frozen cross-section of small intestine was used due to the sharp separation of TJs and AJs in this cell type (M. Itoh, A. Nagafuchi, S. Yonemura, T. Kitani-Yasuda, S. Tsukita and S. Tsukita, "The 220-kD protein colocalizing with cadherins in non-epithelial cells is identical to ZO-1, a tight junction-associated protein in epithelial cells: cDNA cloning and immunoelectron microscopy." J Cell Biol. 1993, 121: 491-502). Furthermore, ZO-1 is known to be a marker for TJs (B. R. Stevenson, J. D. Siliciano, M. S. Mooseker and D. A. Goodenough, "Identification of ZO-1: a high molecular weight polypeptide associated with the tight junction (zonula occludens) in a variety of epithelia." J. Cell Biol. 1986, 103: 755-766; M. Itoh, A. Nagafuchi, S. Yonemura, T. Kitani-Yasuda, S. Tsukita and S. Tsukita, "The 220-kD protein colocalizing with cadherins in non-epithelial cells is identical to ZO-1, a tight junction-associated protein in epithelial cells: cDNA cloning and immunoelectron microscopy." J. Cell Biol. 1993, 121: 491-502).

Immunoelectron microscopy of mouse small intestine absorptive epithelia cell using ultra-thin frozen section technique was performed according to the literature (K. Mandai, H. Nakanishi, A. Satoh, H. Obaishi, M. Wada, H. Nishioka, M. Itoh, A. Mizoguchi, T. Aoki, T. Fujimoto, Y. Matsuda, S. Tsukita and Y. Takai, "Afadin: A novel actin filament-binding protein with one PDZ domain localized at cadherin-based cell-to-cell adherens junction." J. Cell Biol. 1997, 139:517-528).

Figure 7:
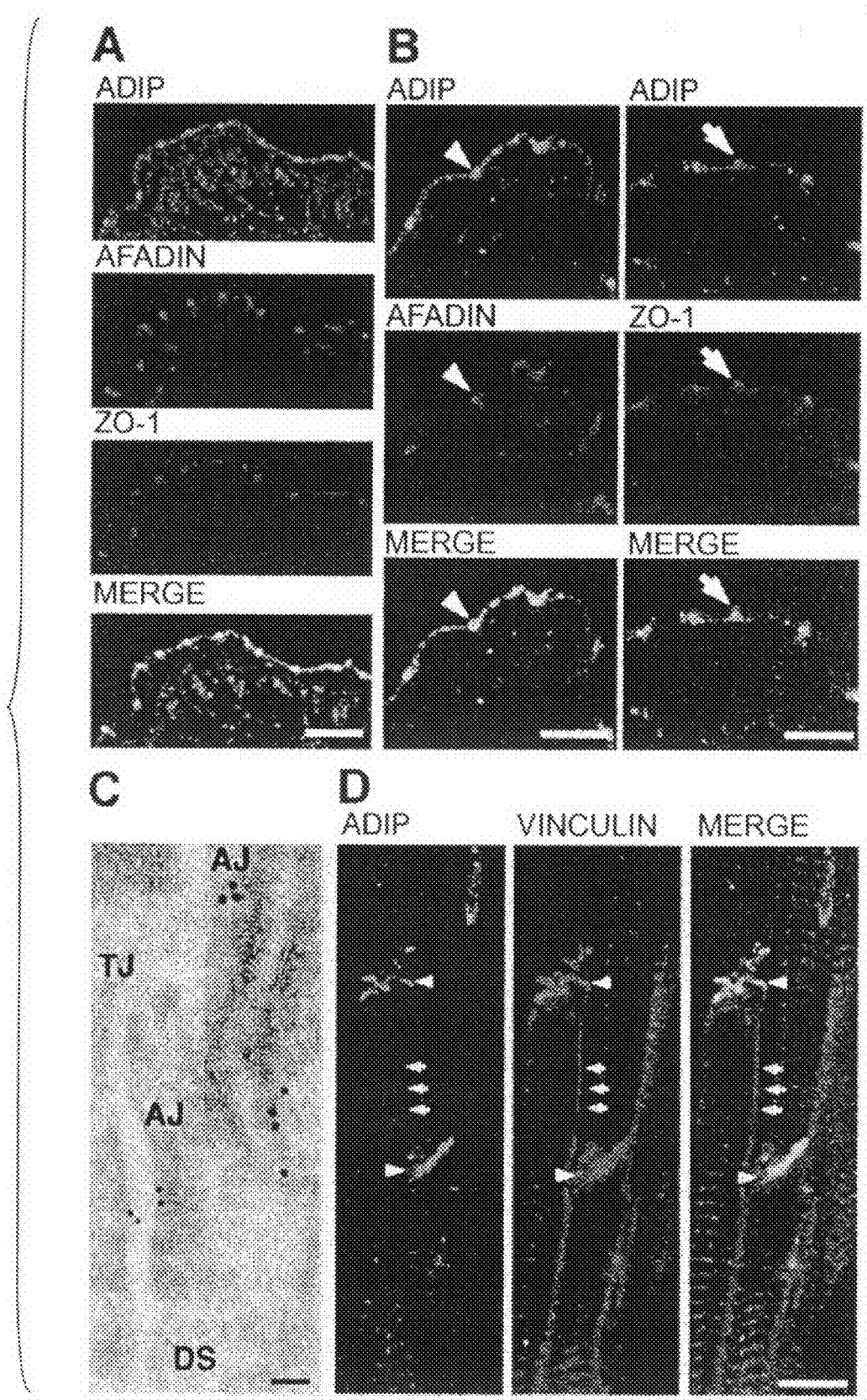
FIG. 7 depicts photographs showing co-localization of ADIP and afadin at AJs in mouse small intestine absorptive epithelial cells.

The results showed that ADIP co-localized with afadin, but localized at a slightly more basal side than the ZO-1 in the absorptive epithelia (FIGS. 7A and 7B).

Moreover, it was revealed that ADIP exclusively localized at AJs undercoated with F-actin bundles and did not localize at TJs and desmosomes (FIG. 7C). This localization pattern of ADIP was identical to that of afadin and nectin but was different from that of E-cadherin, which is concentrated at AJs but is more widely distributed from the apical to basal sides of the lateral plasma membranes (K. Mandai, H. Nakanishi, A. Satoh, H. Obaishi, M. Wada, H. Nishioka, M. Itoh, A. Mizoguchi, T. Aoki, T. Fujimoto, Y. Matsuda, S. Tsukita and Y. Takai, "Afadin: A novel actin filament-binding protein with one PDZ domain localized at cadherin-based cell-to-cell adherens junction." J. Cell Biol. 1997, 139:517-528; K. Takahashi, H. Nakanishi, M. Miyahara, K. Mandai, K. Satoh, A. Satoh, H. Nishioka, J. Aoki, A. Nomoto, A. Mizoguchi and Y. Takai, "Nectin/PRR: an immunoglobulin-like cell adhesion molecule recruited to cadherin-based adherens junctions through interaction with Afadin, a PDZ domain-containing protein." J. Cell Biol. 1999, 145: 539-549).

These results indicated that ADIP co-localize with afadin and nectin at cell-cell AJs undercoated with F-actin bundles.

Example 14

ADIP Signal

The ADIP signal was not detected at focal adhesion sites where the vinculin signal was detected in MDCK cells (FIG. 5B).

In the heart, a focal adhesion site, named costamere, is well developed and periodically located along the lateral borders of cardiac muscle cells (L. Terracio, D. G. Simpson, L. Hilenski, W. Carver, R. S. Decker, N. Vinson and T. K. Borg, "Distribution of vinculin in the Z-disk of striated muscle: analysis by laser scanning confocal microscopy." J. Cell Physiol. 1990, 145: 78-87). Vinculin, but not nectin and afadin, is known to be localized at costameres (K. Mandai, H. Nakanishi, A. Satoh, H. Obaishi, M. Wada, H. Nishioka, M. Itoh, A. Mizoguchi, T. Aoki, T. Fujimoto, Y. Matsuda, S. Tsukita and Y. Takai, "Afadin: A novel actin filament-binding protein with one PDZ domain localized at cadherin-based cell-to-cell adherens junction." J. Cell Biol. 1997, 139: 517-528; K. Takahashi, H. Nakanishi, M. Miyahara, K. Mandai, K. Satoh, A. Satoh, H. Nishioka, J. Aoki, A. Nomoto, A. Mizoguchi and Y. Takai, "Nectin/PRR: an immunoglobulin-like cell adhesion molecule recruited to cadherin-based adherens junctions through interaction with Afadin, a PDZ domain-containing protein." J. Cell Biol. 1999, 145: 539-549).

The ADIP signal was not detected at costameres where the vinculin signal was detected (FIG. 7D, arrows).

Both the ADIP and vinculin signals were detected at the intercalated disc, corresponding to the cell-cell AJs (FIG. 7D, arrowheads).

These results indicate that ADIP does not localize at the cell-matrix junctions.

Example 15

$Ca^{2+}$ Switching Assay

Next, the present inventors investigated the localization of ADIP in comparison with the localization of afadin during destruction and formation of AJs in MDCK cells.

A $Ca^{2+}$ switching assay using MDCK cells was performed as described in the literature (J. Kartenbeck, M. Schmelz, W. W. Franke and B. Geiger, "Endocytosis of junctional cadherins in bovine kidney epithelial (MDBK) cells cultured in low $Ca^{2+}$ ion medium." J. Cell Biol. 1991, 113: 881-892). Specifically, MDCK cells ($1 \times 10^5$) were seeded on an 18-mm glass coverslip in a 12-well culture dish. After 48 hrs, the cells were washed with phosphate buffered saline (PBS) and cultured at 2 mM $Ca^{2+}$ in serum-free DMEM for 60 min. Then, cells were cultured at 2 μM $Ca^{2+}$ (in DMEM containing 5 mM EGTA) for 120 min. After the incubation, cells were washed with PBS and cultured again at 2 mM $Ca^{2+}$ in serum-free DMEM for 60 min. When cells were treated with phorbolester, i.e., 12-o-tetradecanoylphorbol-13-acetate (TPA), the cells were washed with PBS and cultured at 2 mM $Ca^{2+}$ in serum-free DMEM for 60 min. The cells were then cultured at 2 μM $Ca^{2+}$ with 5 mM EGTA for 120 min. After the incubation, 100 nM TPA was added to the medium and then the cells were cultured for another 60 min.

Figure 8:
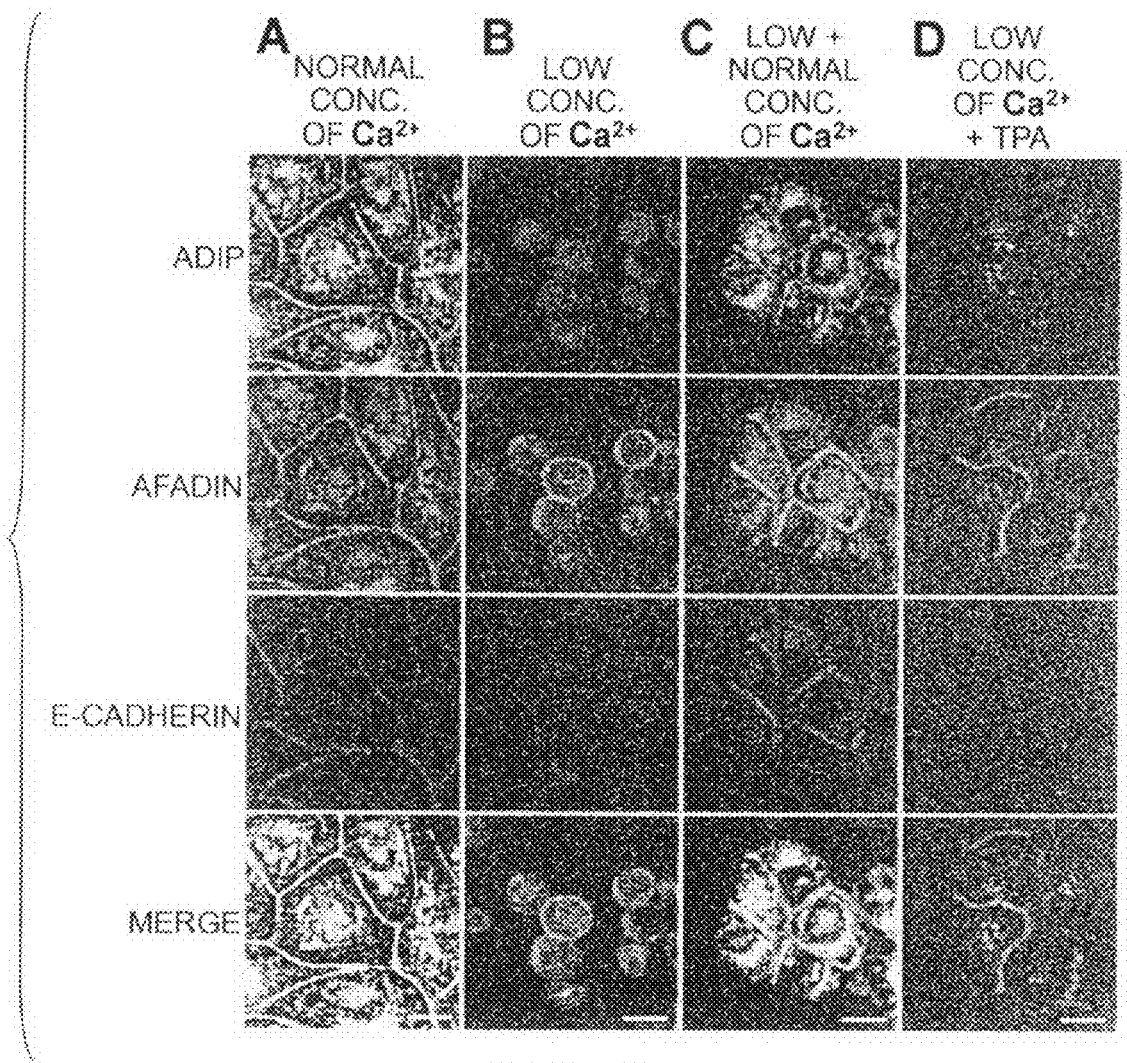
FIG. 8 depicts photographs showing the behavior of ADIP during destruction and formation of junctional complex consisting of AJs and TJs in MDCK cells. MDCK cells were triple-stained with anti-ADIP (M05), anti-afadin and anti-E-cadherin Ab.

As a result, due to the switching of the $Ca^{2+}$ concentration in the culture media from 2 mM to 2 μM, MDCK cells gradually dissociate from each other as described in the literature (J. Kartenbeck, M. Schmelz, W. W. Franke and B. Geiger, "Endocytosis of junctional cadherins in bovine kidney epithelial (MDBK) cells cultured in low $Ca^{2+}$ ion medium." J. Cell Biol. 1991, 113:881-892). Afadin, E-cadherin and ADIP signals were highly concentrated at the cell-cell adhesion sites in cells cultured at 2 mM $Ca^{2+}$ (FIG. 8A). The E-cadherin signal disappeared and partly emerged on intracellular vesicles upon cultivation of these cells at 2 μM $Ca^{2+}$ for 120 min (E-cadherin shown in FIG. 8B). Most of the afadin signal remained at the free surface of the cytoplasmic membrane and formed a cyclic structure (afadin in FIG. 8B) as described in the literatures (T. Sakisaka, H. Nakanishi, K. Takahashi, K. Mandai, M. Miyahara, A. Satoh, K. Takahashi and Y. Takai, "Different behavior of l-afadin and neurabin-II during the formation and destruction of cell-cell adherens junction." Oncogene 1999, 18: 1609-1617; A. Fukuhara, K. Irie, H. Nakanishi, K. Takekuni, T. Kawakatsu, W. Ikeda, A. Yamada, T. Katata, T. Honda, T. Sato, K. Shimizu, H. Ozaki, H. Horiuchi, T. Kita and Y. Takai, "Involvement of Nectin in the Localization of Junctional Adhesion Molecule at Tight Junctions." Oncogene 2002, 21: 7642-7655). The majority of the ADIP signal disappeared from the free surface of the cytoplasmic membrane under the conditions described above (ADIP in FIG. 8B).

Next, MDCK cells pre-cultured at 2 μM $Ca^{2+}$ for 120 min were cultured at 2 mM $Ca^{2+}$ for 60 min to examine the accumulation of ADIP at the cell-cell adhesion sites in comparison with E-cadherin accumulation. After the incubation at 2 mM $Ca^{2+}$, the E-cadherin signal concentrated again at the cell-cell adhesion sites (E-cadherin in FIG. 8C). The ADIP signal also concentrated again at the cell-cell adhesion sites (ADIP in FIG. 8C).

Furthermore, the present inventors revealed that a TJ-like structure is formed and afadin and ZO-1, but not E-cadherin, accumulate at this structure, upon the cultivation of MDCK cells at 2 μM $Ca^{2+}$ for 120 min prior to the incubation at 2 mM Ca with TPA for 60 min (M. S. Balda, L. Gonzalez-Mariscal, K. Matter, M. Cereijido and J. M. Anderson, "Assembly of the tight junction: the role of diacylglycerol." J. Cell Biol. 1993, 123: 293-302; T. Asakura, H. Nakanishi, T. Sakisaka, K. Takahashi, K. Mandai, M. Nishimura, T. Sasaki and Y. Takai, "Similar and differential behaviour between the nectin-afadin-ponsin and cadherin-catenin systems during the formation and disruption of the polarized junctional alignment in epithelial cells." Genes Cells 1999, 4: 573-581; A. Fukuhara, K. Irie, H. Nakanishi, K. Takekuni, T. Kawakatsu, W. Ikeda, A. Yamada, T. Katata, T. Honda, T. Sato, K. Shimizu, H. Ozaki, H. Horiuchi, T. Kita and Y. Takai, "Involvement of Nectin in the Localization of Junctional Adhesion Molecule at Tight Junctions." Oncogene 2002, 21: 7642-7655; A. Fukuhara, K. Irie, A. Yamada, T. Katata, T. Honda, K. Shimizu, H. Nakanishi and Y. Takai, "Role of Nectin in Organization of Tight Junctions in Epithelial Cells." Genes Cells 2002, 7: 1059-1072). Moreover, afadin signal localized at the TPA induced TJ-like structure. However, ADIP and E-cadherin signals did not localize at the structure (FIG. 8D).

These results indicate that ADIP shows a different localization from that of afadin during the destruction and formation of the junctional complex.

Example 16

In Vivo and in Vitro Binding of ADIP to α-actinin-1

The present inventors performed immunoprecipitation analysis to confirm the in vivo and in vitro binding of ADIP to α-actinin-1.

H293 cells were co-transfected with expression vectors carrying the HA-tagged C terminus of α-actinin-1 (HA-α-actinin-1-C; aa 406-892) and FLAG-tagged ADIP (FLAG-mADIP-M; aa 152-436).

When FLAG-tagged ADIP was immunoprecipitated with anti-FLAG mAb from the cell extract, co-immunoprecipitation of HA-α-actinin-1-C was revealed by Western blotting analysis with HA mAb (FIG. 9B).

Endogenous α-actinin co-immunoprecipitated (FIG. 9C) when FLAG-mADIP-M was immunoprecipitated with anti-FLAG Ab from the extract of HEK293 cell transiently expressing FLAG-tagged mADIP (FLAG-mADIP-M; aa 152-436) alone.

Finally, endogenous α-actinin co-immunoprecipitated (FIG. 9D) when endogenous ADIP was immunoprecipitated with anti-ADIP pAb from MDCK cell extracts. α-Actinin did not co-immunoprecipitate with control IgG.

These results indicated that ADIP binds to α-actinin both in vivo and in vitro.

Example 17

Co-localization of ADIP with α-actinin at AJs in MDCK Cells

α-actinin has been demonstrated to interact with α-catenin and localize at AJs (K. A. Knudsen, A. P. Soler, K. R. Johnson and M. J. Wheelock, "Interaction of alpha-actinin with the cadherin/catenin cell-cell adhesion complex via alpha-catenin." J. Cell Biol. 1995, 130: 67-77). Therefore, the present inventors examined whether ADIP co-localizes with α-actinin at AJs in MDCK cells by immunofluorescence microscopy.

Figure 10:
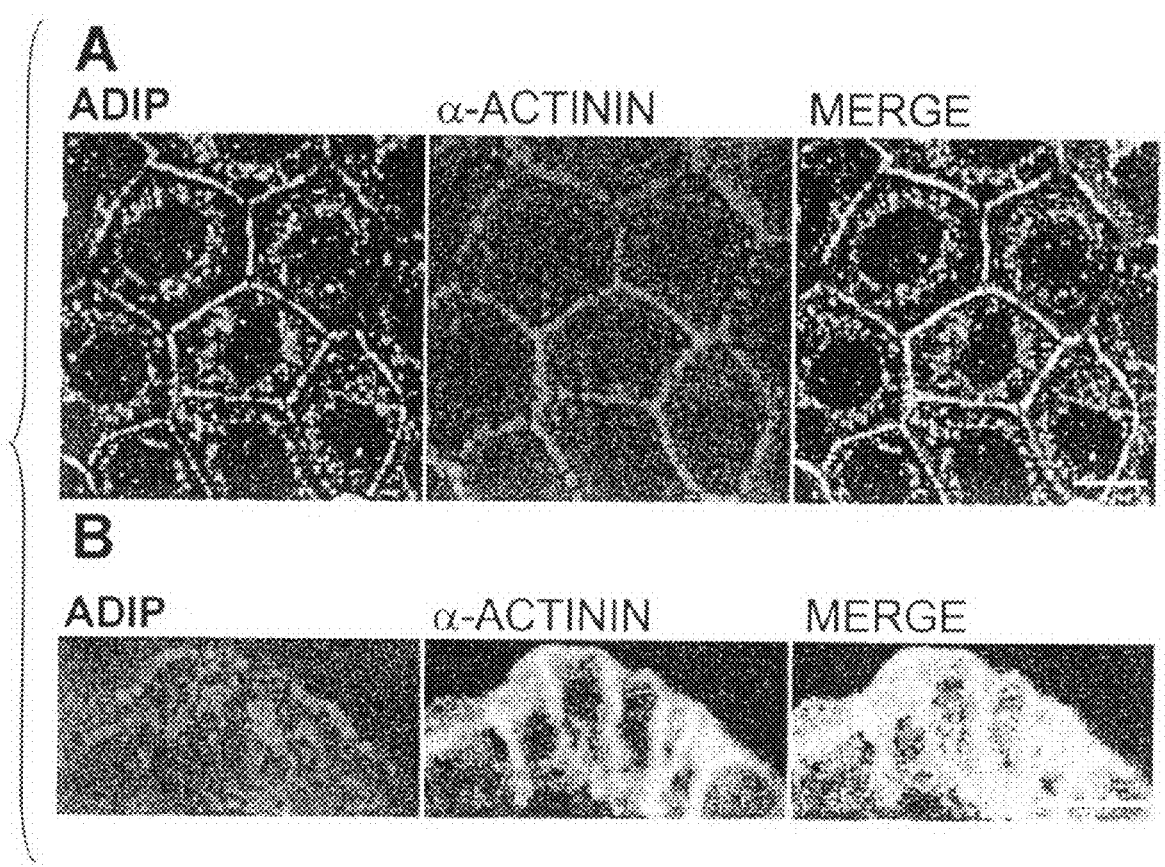
FIG. 10 depicts photographs showing the localization of α-actinin and ADIP at AJs in MDCK cells and mouse small intestine absorptive epithelial cells.

The result showed co-localization of ADIP and α-actinin at the cell-cell junctions (FIG. 10A). Moreover, α-actinin but not ADIP localized at limited adherens sites (data not shown).

The frozen sections of mouse small intestine were double-stained with anti-ADIP pAb and anti-α-actinin mAb in order to confirm co-localization of ADIP and α-actinin at the junctional complex regions.

The result showed that ADIP co-localizes with α-actinin at the absorptive epithelia (FIG. 10B). The localization of ADIP was strictly restricted to the AJs as described above. However, α-actinin was widely distributed from the apical to basal sides of the lateral plasma membranes (FIG. 10B).

These results indicate that ADIP forms a complex with afadin and α-actinin at the cell-cell AJs undercoated with F-actin bundles.

Any patents, published patent applications and publications cited herein are incorporated by reference.

SEQUENCE LISTING

<160> NUMBER OF SEQ ID NOS: 8

<210> SEQ ID NO 1
<211> LENGTH: 2692
<212> TYPE: DNA
<213> ORGANISM: Mus musculus
<220> FEATURE:
<221> NAME/KEY: CDS
<222> LOCATION: (80)..(1927)
<223> OTHER INFORMATION: afadin-and alpha-actinin-binding protein

<400> SEQUENCE: 1

```
cgtaggagag tgacaggagc tgttgtaagc gtcgcagcac tgagccgcct cctcaggtat          60
cctggctctg gaacttgct atg gga gat tgg atg act gtg aca gat cca gtt         112
                    Met Gly Asp Trp Met Thr Val Thr Asp Pro Val
                     1               5                  10 ctg tgt aca gaa aac aaa aat ctc tct caa tat acc tca gaa aca aag         160
Leu Cys Thr Glu Asn Lys Asn Leu Ser Gln Tyr Thr Ser Glu Thr Lys
             15                  20                  25 atg tct ccg tcc agt ttg tac tcc cag caa gtt ctg tgc tct tca gta         208
Met Ser Pro Ser Ser Leu Tyr Ser Gln Gln Val Leu Cys Ser Ser Val
         30                  35                  40 cct tta tcc aaa aac gtg cat ggt gtt ttc ggt gtc ttc tgc aca gga         256
Pro Leu Ser Lys Asn Val His Gly Val Phe Gly Val Phe Cys Thr Gly
     45                  50                  55 gag aac att gaa caa agt att tcc tat ctt gat cag gag ctg acc acc         304
Glu Asn Ile Glu Gln Ser Ile Ser Tyr Leu Asp Gln Glu Leu Thr Thr
 60                  65                  70                  75 ttc ggg ttt cct tcc ttg tat gaa gaa tcc aaa agt aaa gag gca aag         352
Phe Gly Phe Pro Ser Leu Tyr Glu Glu Ser Lys Ser Lys Glu Ala Lys
                 80                  85                  90 aga gaa tta aat ata gtc gct gtt ctg aac tgt atg aac gag ctg ctc         400
Arg Glu Leu Asn Ile Val Ala Val Leu Asn Cys Met Asn Glu Leu Leu
             95                 100                 105 gtg ctt cag cgg aag aac ctg ctg gcc cag gag agc gtg gag aca cag         448
Val Leu Gln Arg Lys Asn Leu Leu Ala Gln Glu Ser Val Glu Thr Gln
        110                 115                 120 aac ttg aag ctg ggc agt gac atg gac cac ctg cag agc tgc tac gcc         496
Asn Leu Lys Leu Gly Ser Asp Met Asp His Leu Gln Ser Cys Tyr Ala
    125                 130                 135 aaa ctt aag gag cag ttg gaa acg tcc agg cgg gag atg atc ggg ctt         544
Lys Leu Lys Glu Gln Leu Glu Thr Ser Arg Arg Glu Met Ile Gly Leu
140                 145                 150                 155 caa gag aga gac agg cag ctg cag tgc aag aac agg agt ttg cat cag         592
Gln Glu Arg Asp Arg Gln Leu Gln Cys Lys Asn Arg Ser Leu His Gln
                160                 165                 170 ctc ctg aag aat gag aaa gat gag gta caa aaa tta caa aat atc ata         640
Leu Leu Lys Asn Glu Lys Asp Glu Val Gln Lys Leu Gln Asn Ile Ile
            175                 180                 185 gcc agc cgg gct act cag tat aat cat gat gtg aag agg aag gag cgt         688
Ala Ser Arg Ala Thr Gln Tyr Asn His Asp Val Lys Arg Lys Glu Arg
        190                 195                 200 gaa tat aat aag cta aag gag cgc ctg cat cag ctc gtt atg aac aag         736
Glu Tyr Asn Lys Leu Lys Glu Arg Leu His Gln Leu Val Met Asn Lys
    205                 210                 215 aag gat aaa aac ata gcc atg gat gtt tta aat tat gtg ggt cga gct         784
Lys Asp Lys Asn Ile Ala Met Asp Val Leu Asn Tyr Val Gly Arg Ala
220                 225                 230                 235
```

```
                                                            -continued gat ggc aaa cga ggc tca tgg agg act gac aaa aca gaa gcc agg aat     832
Asp Gly Lys Arg Gly Ser Trp Arg Thr Asp Lys Thr Glu Ala Arg Asn
            240                 245                 250 gaa gat gag atg tac aaa att ctg ttg aat gat tat gag tac cgc cag     880
Glu Asp Glu Met Tyr Lys Ile Leu Leu Asn Asp Tyr Glu Tyr Arg Gln
                255                 260                 265 aag cag atc ctg atg gag aac gcg gag ctg aag aag gtc ctc cag cag     928
Lys Gln Ile Leu Met Glu Asn Ala Glu Leu Lys Lys Val Leu Gln Gln
        270                 275                 280 atg aag aag gag atg atc tct ctc ctg tct cct cag aag aag aag ccc     976
Met Lys Lys Glu Met Ile Ser Leu Leu Ser Pro Gln Lys Lys Lys Pro
    285                 290                 295 agg gaa aga gca gag gac ggc aca ggc act gtt gct atc tcc gat ata    1024
Arg Glu Arg Ala Glu Asp Gly Thr Gly Thr Val Ala Ile Ser Asp Ile
300                 305                 310                 315 gaa gat gac tct ggg gaa ctg agc aga gac agc gtg tgg ggc ctt tcc    1072
Glu Asp Asp Ser Gly Glu Leu Ser Arg Asp Ser Val Trp Gly Leu Ser
                320                 325                 330 tgt gac act gtg aga gag cag ctg aca aac agc atc agg aaa cag tgg    1120
Cys Asp Thr Val Arg Glu Gln Leu Thr Asn Ser Ile Arg Lys Gln Trp
                335                 340                 345 aga att ttg aaa agt cat gta gaa aaa ctc gat aac caa gct tcg aag    1168
Arg Ile Leu Lys Ser His Val Glu Lys Leu Asp Asn Gln Ala Ser Lys
        350                 355                 360 gta cac tca gag ggc ctt aat gag gag gac gtc atc tca cga caa gac    1216
Val His Ser Glu Gly Leu Asn Glu Glu Asp Val Ile Ser Arg Gln Asp
    365                 370                 375 cat gag caa gag act gag aaa ctg gag ctg gag att gag cgg tgt aaa    1264
His Glu Gln Glu Thr Glu Lys Leu Glu Leu Glu Ile Glu Arg Cys Lys
380                 385                 390                 395 gag atg atc aag gct cag cag cag ctc tta cag cag cag ctg gcc acc    1312
Glu Met Ile Lys Ala Gln Gln Gln Leu Leu Gln Gln Gln Leu Ala Thr
                400                 405                 410 acg tgt gat gat gac acc acc tca ctg ttg cga gac tgt tac ttg ctg    1360
Thr Cys Asp Asp Asp Thr Thr Ser Leu Leu Arg Asp Cys Tyr Leu Leu
            415                 420                 425 gaa gaa aag gaa cgc ctt aaa gaa gag tgg acc ctt ttt aaa gag caa    1408
Glu Glu Lys Glu Arg Leu Lys Glu Glu Trp Thr Leu Phe Lys Glu Gln
        430                 435                 440 aaa aag aat ttt gag aga gaa agg cga agc ttt aca gaa gct gcc att    1456
Lys Lys Asn Phe Glu Arg Glu Arg Arg Ser Phe Thr Glu Ala Ala Ile
    445                 450                 455 cga ttg ggg ttg gag aga aag gcg ttt gaa gaa gag cga gcc agc tgg    1504
Arg Leu Gly Leu Glu Arg Lys Ala Phe Glu Glu Glu Arg Ala Ser Trp
460                 465                 470                 475 gta aag cag cag ttt tta aac atg acg aac ttt gac cac cag aac tca    1552
Val Lys Gln Gln Phe Leu Asn Met Thr Asn Phe Asp His Gln Asn Ser
                480                 485                 490 gaa aat gtg aaa ctt ttc agt gcc ttc tca gga agt tct gat cca gac    1600
Glu Asn Val Lys Leu Phe Ser Ala Phe Ser Gly Ser Ser Asp Pro Asp
            495                 500                 505 aat ctt ata gtc cac tca cgg cca cgg caa aag aag cta cac agt gtg    1648
Asn Leu Ile Val His Ser Arg Pro Arg Gln Lys Lys Leu His Ser Val
        510                 515                 520 gct aat ggg gtg cca gct tgc aca tca aaa ctg act aaa tct ctt cct    1696
Ala Asn Gly Val Pro Ala Cys Thr Ser Lys Leu Thr Lys Ser Leu Pro
    525                 530                 535 gcc tca cct tct act tca gac ttt cgc cag aca cat tca tgt gtg tct    1744
Ala Ser Pro Ser Thr Ser Asp Phe Arg Gln Thr His Ser Cys Val Ser
540                 545                 550                 555
```

-continued

```
gaa cac agt tcc atc agt gtg ctg aat ata act cct gaa gaa agt aaa    1792
Glu His Ser Ser Ile Ser Val Leu Asn Ile Thr Pro Glu Glu Ser Lys
            560                 565                 570 cca agt gag gtt gca aga gaa agc acg gat cag aag tgg agc gtg cag    1840
Pro Ser Glu Val Ala Arg Glu Ser Thr Asp Gln Lys Trp Ser Val Gln
        575                 580                 585 tcg agg ccc agc tcg cgg gag ggg tgc tac agc gga tgc tcc tcg gcc    1888
Ser Arg Pro Ser Ser Arg Glu Gly Cys Tyr Ser Gly Cys Ser Ser Ala
    590                 595                 600 ttc agg agc gct cac ggg gac cga gat gac tta cct taa atgtgcgggc     1937
Phe Arg Ser Ala His Gly Asp Arg Asp Asp Leu Pro
    605                 610                 615 tgcagtgctg ttcccagatg tgcgctagag gagttgacac agggtgtagc ataaagtcag  1997
tcgtctaact taagatgctc agagttgttt gtttggactt cgctgtcttc ccccaaagag  2057
ctgaaatgct aagctactta aaaggatgca aagctttggt tgtgtgttag taacagaagc  2117
ccctggctct gtgactgcag gaatgcatgg cgtttggatg gaaacagaag cgctggaatg  2177
attgcctcgc caggtaccga gaagagcact tttagggact ggttcctgta aacattaaat  2237
attcgtccca agtgtggttg gcattggaag tgtagccttt acttgaatgt atactgtaga  2297
tttttaacaa agcaggttct atatttatta tgtttagtgt gattttggga ttacctcttt  2357
catatgtttt gtgtctgtac ataaatatac atgactatgt taagaggctt taaggtttaa  2417
aaacttcaca ccatgcttga gtatagcatt tcatgccaat taaaatgttt tcagtggcat  2477
ggtgtttaca gaggttagga ccactgccac atgacagtta agactttatt tttaagccat  2537
ctgggcaata aaaattcaaa gccccttcat aagctgagtt cagataacta gaactactaa  2597
cgttacattt ttgagatttt taagcattg tattttattt tatatatgtg aatgttataa   2657
tttctaagag gaatattgat tatggagtaa tgggg                             2692
```

<210> SEQ ID NO 2
<211> LENGTH: 615
<212> TYPE: PRT
<213> ORGANISM: Mus musculus

<400> SEQUENCE: 2

```
Met Gly Asp Trp Met Thr Val Thr Asp Pro Val Leu Cys Thr Glu Asn
1               5                   10                  15

Lys Asn Leu Ser Gln Tyr Thr Ser Glu Thr Lys Met Ser Pro Ser Ser
            20                  25                  30

Leu Tyr Ser Gln Gln Val Leu Cys Ser Ser Val Pro Leu Ser Lys Asn
        35                  40                  45

Val His Gly Val Phe Gly Val Phe Cys Thr Gly Glu Asn Ile Glu Gln
    50                  55                  60

Ser Ile Ser Tyr Leu Asp Gln Glu Leu Thr Thr Phe Gly Phe Pro Ser
65                  70                  75                  80

Leu Tyr Glu Glu Ser Lys Ser Lys Glu Ala Lys Arg Glu Leu Asn Ile
            85                  90                  95

Val Ala Val Leu Asn Cys Met Asn Glu Leu Leu Val Leu Gln Arg Lys
        100                 105                 110

Asn Leu Leu Ala Gln Glu Ser Val Glu Thr Gln Asn Leu Lys Leu Gly
    115                 120                 125

Ser Asp Met Asp His Leu Gln Ser Cys Tyr Ala Lys Leu Lys Glu Gln
130                 135                 140
```

-continued

```
Leu Glu Thr Ser Arg Arg Glu Met Ile Gly Leu Gln Glu Arg Asp Arg
145                 150                 155                 160

Gln Leu Gln Cys Lys Asn Arg Ser Leu His Gln Leu Leu Lys Asn Glu
            165                 170                 175

Lys Asp Glu Val Gln Lys Leu Gln Asn Ile Ile Ala Ser Arg Ala Thr
                180                 185                 190

Gln Tyr Asn His Asp Val Lys Arg Lys Glu Arg Glu Tyr Asn Lys Leu
            195                 200                 205

Lys Glu Arg Leu His Gln Leu Val Met Asn Lys Lys Asp Lys Asn Ile
        210                 215                 220

Ala Met Asp Val Leu Asn Tyr Val Gly Arg Ala Asp Gly Lys Arg Gly
225                 230                 235                 240

Ser Trp Arg Thr Asp Lys Thr Glu Ala Arg Asn Glu Asp Glu Met Tyr
                245                 250                 255

Lys Ile Leu Leu Asn Asp Tyr Glu Tyr Arg Gln Lys Gln Ile Leu Met
                260                 265                 270

Glu Asn Ala Glu Leu Lys Lys Val Leu Gln Gln Met Lys Lys Glu Met
            275                 280                 285

Ile Ser Leu Leu Ser Pro Gln Lys Lys Pro Arg Glu Arg Ala Glu
        290                 295                 300

Asp Gly Thr Gly Thr Val Ala Ile Ser Asp Ile Glu Asp Asp Ser Gly
305                 310                 315                 320

Glu Leu Ser Arg Asp Ser Val Trp Gly Leu Ser Cys Asp Thr Val Arg
                325                 330                 335

Glu Gln Leu Thr Asn Ser Ile Arg Lys Gln Trp Arg Ile Leu Lys Ser
            340                 345                 350

His Val Glu Lys Leu Asp Asn Gln Ala Ser Lys Val His Ser Glu Gly
        355                 360                 365

Leu Asn Glu Glu Asp Val Ile Ser Arg Gln Asp His Glu Gln Glu Thr
370                 375                 380

Glu Lys Leu Glu Leu Glu Ile Glu Arg Cys Lys Glu Met Ile Lys Ala
385                 390                 395                 400

Gln Gln Gln Leu Leu Gln Gln Leu Ala Thr Thr Cys Asp Asp Asp
            405                 410                 415

Thr Thr Ser Leu Leu Arg Asp Cys Tyr Leu Leu Glu Gly Lys Glu Arg
                420                 425                 430

Leu Lys Glu Glu Trp Thr Leu Phe Lys Glu Gln Lys Lys Asn Phe Glu
            435                 440                 445

Arg Glu Arg Arg Ser Phe Thr Glu Ala Ala Ile Arg Leu Gly Leu Glu
        450                 455                 460

Arg Lys Ala Phe Glu Glu Arg Ala Ser Trp Val Lys Gln Gln Phe
465                 470                 475                 480

Leu Asn Met Thr Asn Phe Asp His Gln Asn Ser Glu Asn Val Lys Leu
                485                 490                 495

Phe Ser Ala Phe Ser Gly Ser Ser Asp Pro Asp Asn Leu Ile Val His
            500                 505                 510

Ser Arg Pro Arg Gln Lys Lys Leu His Ser Val Ala Asn Gly Val Pro
        515                 520                 525

Ala Cys Thr Ser Lys Leu Thr Lys Ser Leu Pro Ala Ser Pro Ser Thr
530                 535                 540

Ser Asp Phe Arg Gln Thr His Ser Cys Val Ser Glu His Ser Ser Ile
545                 550                 555                 560
```

```
Ser Val Leu Asn Ile Thr Pro Glu Glu Ser Lys Pro Ser Glu Val Ala
            565                 570                 575

Arg Glu Ser Thr Asp Gln Lys Trp Ser Val Gln Ser Arg Pro Ser Ser
        580                 585                 590

Arg Glu Gly Cys Tyr Ser Gly Cys Ser Ser Ala Phe Arg Ser Ala His
    595                 600                 605

Gly Asp Arg Asp Leu Pro
610             615

<210> SEQ ID NO 3
<211> LENGTH: 3195
<212> TYPE: DNA
<213> ORGANISM: Rattus norvegicus
<220> FEATURE:
<221> NAME/KEY: CDS
<222> LOCATION: (79)..(1920)
<223> OTHER INFORMATION:
<220> FEATURE:
<221> NAME/KEY: misc_feature
<222> LOCATION: (2422)..(2422)
<223> OTHER INFORMATION: "n"=any one base of a, t, c, or g

<400> SEQUENCE: 3
```

| | | |
|---|---|---|
| gtaggagagt gacaggagct gttgtgcatg ccccagcact gaactgcctt ctcagggacc | | 60 |
| ctggctctgg gactggct atg gga gat tgg atg act gtt aca gat cca gtt<br>                     Met Gly Asp Trp Met Thr Val Thr Asp Pro Val<br>                      1                5                    10 | | 111 |
| ctg tgt aca gaa aac aaa aat ctc tct caa tat acc tca gaa aca aag<br>Leu Cys Thr Glu Asn Lys Asn Leu Ser Gln Tyr Thr Ser Glu Thr Lys<br>               15                   20                   25 | | 159 |
| atg tct ccg tca agt tta tac tcg cag caa gta ctg tgc tct gca aca<br>Met Ser Pro Ser Ser Leu Tyr Ser Gln Gln Val Leu Cys Ser Ala Thr<br> 30                    35                   40 | | 207 |
| cct tta tcc aag aat gtg cat ggt gtt ttc agt gcc ttc tgc aca gga<br>Pro Leu Ser Lys Asn Val His Gly Val Phe Ser Ala Phe Cys Thr Gly<br>     45                   50                   55 | | 255 |
| gag aac atc gaa cag agt att tcg tat ctt gat cag gaa ctg act acc<br>Glu Asn Ile Glu Gln Ser Ile Ser Tyr Leu Asp Gln Glu Leu Thr Thr<br>60                 65                   70                   75 | | 303 |
| ttc ggt ttc cct tcc ttg tat gaa gaa tcc aaa agt aag gag gcg aag<br>Phe Gly Phe Pro Ser Leu Tyr Glu Glu Ser Lys Ser Lys Glu Ala Lys<br>               80                   85                   90 | | 351 |
| cga gag tta agt ata gtt gct ctt ctg aac tgc atg aat gag ctg ctt<br>Arg Glu Leu Ser Ile Val Ala Leu Leu Asn Cys Met Asn Glu Leu Leu<br>                   95                 100               105 | | 399 |
| gtg ctt cag cgg aag aac ctc ctg gcc cag gaa agc gtg gag aca cag<br>Val Leu Gln Arg Lys Asn Leu Leu Ala Gln Glu Ser Val Glu Thr Gln<br>110                 115                 120 | | 447 |
| aat ctg aag ctg ggc agt gac atg gac cac ctg cag agc tgc tac gcc<br>Asn Leu Lys Leu Gly Ser Asp Met Asp His Leu Gln Ser Cys Tyr Ala<br>     125                   130                 135 | | 495 |
| aaa ctt aag gaa cag ttg gag gcc tcc agg cga gag atg atc agc ctt<br>Lys Leu Lys Glu Gln Leu Glu Ala Ser Arg Arg Glu Met Ile Ser Leu<br>140                 145                 150               155 | | 543 |
| cag gag aga gac aga cag cta cag tgc aaa aac agg aat ttg cat cag<br>Gln Glu Arg Asp Arg Gln Leu Gln Cys Lys Asn Arg Asn Leu His Gln<br>               160                 165               170 | | 591 |
| ctc ctg aaa aac gag aaa gaa gag gta caa aaa tta caa aat atc ata<br>Leu Leu Lys Asn Glu Lys Glu Glu Val Gln Lys Leu Gln Asn Ile Ile<br>175                 180                 185 | | 639 |

```
gcc agt cgg gct act cag tat aat cat gat gtg aag aga aag gag cgg      687
Ala Ser Arg Ala Thr Gln Tyr Asn His Asp Val Lys Arg Lys Glu Arg
        190                 195                 200 gag tac aat aaa ctg aag gag cgt ctg cat cag ctt gtt atg aac aag      735
Glu Tyr Asn Lys Leu Lys Glu Arg Leu His Gln Leu Val Met Asn Lys
    205                 210                 215 aag gat aaa aat ata gcc atg gac gtt tta aat tac gtg ggc cga gtg      783
Lys Asp Lys Asn Ile Ala Met Asp Val Leu Asn Tyr Val Gly Arg Val
220                 225                 230                 235 gat gga aag cga ggc tcc tgg agg act gat aaa aca gaa gcc agg aat      831
Asp Gly Lys Arg Gly Ser Trp Arg Thr Asp Lys Thr Glu Ala Arg Asn
                240                 245                 250 gaa gat gaa atg tac aaa att ctg ctg aat gat tat gag tac cgc cag      879
Glu Asp Glu Met Tyr Lys Ile Leu Leu Asn Asp Tyr Glu Tyr Arg Gln
            255                 260                 265 aag cag atc ctg ctg gag aat gcg gag ctg aag aag gtc ctc cag cag      927
Lys Gln Ile Leu Leu Glu Asn Ala Glu Leu Lys Lys Val Leu Gln Gln
        270                 275                 280 atg aag aaa gag atg atc tct ctc ctt tct cct caa aag aag aaa ccc      975
Met Lys Lys Glu Met Ile Ser Leu Leu Ser Pro Gln Lys Lys Lys Pro
    285                 290                 295 aga gaa aga gca gag gac agc aca ggc act gtt gtc atc tcc gat gta     1023
Arg Glu Arg Ala Glu Asp Ser Thr Gly Thr Val Val Ile Ser Asp Val
300                 305                 310                 315 gaa gac gac gct ggg gag ctg agc aga gat ggt gtg tgg agc ctt tcc     1071
Glu Asp Asp Ala Gly Glu Leu Ser Arg Asp Gly Val Trp Ser Leu Ser
                320                 325                 330 tgt gac act gtc agg gag cag ctt aca aac agc atc agg aag cag tgg     1119
Cys Asp Thr Val Arg Glu Gln Leu Thr Asn Ser Ile Arg Lys Gln Trp
            335                 340                 345 aga att ctg aaa agc cat gtg gaa aaa ctt gat aac caa gct tca aag     1167
Arg Ile Leu Lys Ser His Val Glu Lys Leu Asp Asn Gln Ala Ser Lys
        350                 355                 360 gta cac tca gag ggc ttt cat gaa gag gac gtc atc tca cga caa gac     1215
Val His Ser Glu Gly Phe His Glu Glu Asp Val Ile Ser Arg Gln Asp
    365                 370                 375 cat gag caa gag act gag aaa ctg gag ctg gag att gag cgg tgt aaa     1263
His Glu Gln Glu Thr Glu Lys Leu Glu Leu Glu Ile Glu Arg Cys Lys
380                 385                 390                 395 gag atg atc aag gct cag cag cag ctc tta cag caa cag ctg gcc act     1311
Glu Met Ile Lys Ala Gln Gln Gln Leu Leu Gln Gln Gln Leu Ala Thr
                400                 405                 410 gcg tgt gat gac gac acc acc tca ctg ttg cga gac tgt tac ttg ctt     1359
Ala Cys Asp Asp Asp Thr Thr Ser Leu Leu Arg Asp Cys Tyr Leu Leu
            415                 420                 425 gaa gaa aag gaa cgc ctt aaa gaa gag tgg tcc ctt ttt aaa gag caa     1407
Glu Glu Lys Glu Arg Leu Lys Glu Glu Trp Ser Leu Phe Lys Glu Gln
        430                 435                 440 aaa aag aat ttt gag aga gaa aga cga agc ttt aca gaa gct gct att     1455
Lys Lys Asn Phe Glu Arg Glu Arg Arg Ser Phe Thr Glu Ala Ala Ile
    445                 450                 455 cgc ttg ggg ttg gag aga aag gcg ttt gag gaa gag cga gcc agc tgg     1503
Arg Leu Gly Leu Glu Arg Lys Ala Phe Glu Glu Glu Arg Ala Ser Trp
460                 465                 470                 475 gtg aag cag cag ttt tta aac atg acg acc ttt gat cac cag aac tca     1551
Val Lys Gln Gln Phe Leu Asn Met Thr Thr Phe Asp His Gln Asn Ser
                480                 485                 490 gaa aat gtg aaa ctt ttc agt gcc ttt tca gga agt tct gat cca gac     1599
Glu Asn Val Lys Leu Phe Ser Ala Phe Ser Gly Ser Ser Asp Pro Asp
            495                 500                 505
```

-continued

| | | |
|---|---|---|
| aat ctt ata gtc cac cca cgg cca cgg caa aag aag cca cac agt gtc<br>Asn Leu Ile Val His Pro Arg Pro Arg Gln Lys Lys Pro His Ser Val<br>    510                    515                  520 | | 1647 |
| gct aat ggg gtg cca gct tgc aca tcc aaa ctg gct aag tct ctt ccg<br>Ala Asn Gly Val Pro Ala Cys Thr Ser Lys Leu Ala Lys Ser Leu Pro<br>525                    530                  535 | | 1695 |
| acc tca cct tca gac ttc tgc ccg tct cgc tca tgt gtg tct gag cac<br>Thr Ser Pro Ser Asp Phe Cys Pro Ser Arg Ser Cys Val Ser Glu His<br>540                    545                  550                555 | | 1743 |
| agt ccc gtc agt gcg ctg act gtg act cct gaa gaa acc aaa ccg aat<br>Ser Pro Val Ser Ala Leu Thr Val Thr Pro Glu Glu Thr Lys Pro Asn<br>                560                  565                  570 | | 1791 |
| gag gtt gga aga gaa agt acg gac cag aag tgg agc gtg gtg tcc aga<br>Glu Val Gly Arg Glu Ser Thr Asp Gln Lys Trp Ser Val Val Ser Arg<br>                575                  580                  585 | | 1839 |
| ccc agc tcc cgg gag ggt tgc tac ggt gga tgc tcc tcg gcc tac aca<br>Pro Ser Ser Arg Glu Gly Cys Tyr Gly Gly Cys Ser Ser Ala Tyr Thr<br>590                    595                  600 | | 1887 |
| agc tcc cac gtg gaa cga gat gac tta cca tag gtgctcgggc tgcagcgctg<br>Ser Ser His Val Glu Arg Asp Asp Leu Pro<br>    605                    610 | | 1940 |
| tcctggagtg catgagagga attgacacgg ggtgtagcat aaagtcagcc atctaccgta | | 2000 |
| agatgtcgga gttatttgtt tggacttccc agtctttccc caaagagctg aaacgcttta | | 2060 |
| gaggatgcga aagctttggc tgtgtgttag taacagaagc ctctggctct gtgagtaaag | | 2120 |
| gaatgtatgg tgtttggtgg gaaacaaaag cacgagaatg atttcctctt ccgggtactg | | 2180 |
| agaatagcac ttttagggac tgattcttgt aaacattaaa tttttgtccc aagtatggtt | | 2240 |
| ggcattggaa gtttagtctt tacttgaatg tacactgtag atttttaaca aagcagttct | | 2300 |
| atatttatta tgtttagtgt gattttggga ttacctcttt catatgtttt ctgcctgtac | | 2360 |
| ataaatatac atgactatgt taagaggctt taaggtttaa aaatttcaca ccatgctcga | | 2420 |
| gnatagcatt tcatgccaat taaaatgttt tcagtggcat ggtgtttaca gatgtgttag | | 2480 |
| gaccactgcc acatgacagt taagatttta ttttaagcc atttgggcaa taaaaattca | | 2540 |
| aagccacttc ataagctaag ttcagatagc taaaactact aacattacat ttttgagatt | | 2600 |
| tataaagcat tatattttat tttatatatg tgactgttat aatttctaag aggaatgtgg | | 2660 |
| attatgaagc aatgggggaa agacagaagt gactaatagt gcaagagcat tgggtgaagg | | 2720 |
| gacggctgat gaggatatgg gagacctggg tggtgatctt ttccttaccg acggtgcggt | | 2780 |
| gcggcgatct ctgtaccgcc agggctttct atcattgcca atactttgt aattaaagag | | 2840 |
| attttcaact acataccact actaaagtaa gacagtgtaa aactttggct tttgtaattg | | 2900 |
| acactctgga cactggtgtg ttgttcattt ctagaacaat cgtaggctct tttctctgtt | | 2960 |
| tctgctgcat gtttcttcat gagaagtatg ttactattga cagtaatgac actgacagtg | | 3020 |
| actgtagacg taggcccaga cttctcctgg gtggattttc atccagcagc ttttaagtgc | | 3080 |
| ctcgccctgc tcgtctctgc acatagccgc cgacacaagc cctcgcttga tgatgcagat | | 3140 |
| agtccatctg cctttctctc cccttgccct gctatgactg ttgcattaaa ttcat | | 3195 |

<210> SEQ ID NO 4
<211> LENGTH: 613
<212> TYPE: PRT
<213> ORGANISM: Rattus norvegicus

<400> SEQUENCE: 4

```
Met Gly Asp Trp Met Thr Val Thr Asp Pro Val Leu Cys Thr Glu Asn
1               5                   10                  15

Lys Asn Leu Ser Gln Tyr Thr Ser Glu Thr Lys Met Ser Pro Ser Ser
            20                  25                  30

Leu Tyr Ser Gln Gln Val Leu Cys Ser Ala Thr Pro Leu Ser Lys Asn
        35                  40                  45

Val His Gly Val Phe Ser Ala Phe Cys Thr Gly Glu Asn Ile Glu Gln
    50                  55                  60

Ser Ile Ser Tyr Leu Asp Gln Glu Leu Thr Thr Phe Gly Phe Pro Ser
65              70                  75                  80

Leu Tyr Glu Glu Ser Lys Ser Lys Glu Ala Lys Arg Glu Leu Ser Ile
                85                  90                  95

Val Ala Leu Leu Asn Cys Met Asn Glu Leu Leu Val Leu Gln Arg Lys
            100                 105                 110

Asn Leu Leu Ala Gln Glu Ser Val Glu Thr Gln Asn Leu Lys Leu Gly
        115                 120                 125

Ser Asp Met Asp His Leu Gln Ser Cys Tyr Ala Lys Leu Lys Glu Gln
    130                 135                 140

Leu Glu Ala Ser Arg Arg Glu Met Ile Ser Leu Gln Glu Arg Asp Arg
145             150                 155                 160

Gln Leu Gln Cys Lys Asn Arg Asn Leu His Gln Leu Leu Lys Asn Glu
                165                 170                 175

Lys Glu Glu Val Gln Lys Leu Gln Asn Ile Ile Ala Ser Arg Ala Thr
            180                 185                 190

Gln Tyr Asn His Asp Val Lys Arg Lys Glu Arg Glu Tyr Asn Lys Leu
        195                 200                 205

Lys Glu Arg Leu His Gln Leu Val Met Asn Lys Lys Asp Lys Asn Ile
210             215                 220

Ala Met Asp Val Leu Asn Tyr Val Gly Arg Val Asp Gly Lys Arg Gly
225                 230                 235                 240

Ser Trp Arg Thr Asp Lys Thr Glu Ala Arg Asn Glu Asp Glu Met Tyr
                245                 250                 255

Lys Ile Leu Leu Asn Asp Tyr Glu Tyr Arg Gln Lys Gln Ile Leu Leu
            260                 265                 270

Glu Asn Ala Glu Leu Lys Lys Val Leu Gln Gln Met Lys Lys Glu Met
        275                 280                 285

Ile Ser Leu Leu Ser Pro Gln Lys Lys Pro Arg Glu Arg Ala Glu
    290                 295                 300

Asp Ser Thr Gly Thr Val Val Ile Ser Asp Val Glu Asp Ala Gly
305                 310                 315                 320

Glu Leu Ser Arg Asp Gly Val Trp Ser Leu Ser Cys Asp Thr Val Arg
                325                 330                 335

Glu Gln Leu Thr Asn Ser Ile Arg Lys Gln Trp Arg Ile Leu Lys Ser
            340                 345                 350

His Val Glu Lys Leu Asp Asn Gln Ala Ser Lys Val His Ser Glu Gly
        355                 360                 365

Phe His Glu Glu Asp Val Ile Ser Arg Gln Asp His Glu Gln Glu Thr
    370                 375                 380

Glu Lys Leu Glu Leu Glu Ile Glu Arg Cys Lys Glu Met Ile Lys Ala
385                 390                 395                 400

Gln Gln Gln Leu Leu Gln Gln Leu Ala Thr Ala Cys Asp Asp
                405                 410                 415
```

-continued

```
Thr Thr Ser Leu Leu Arg Asp Cys Tyr Leu Glu Glu Lys Glu Arg
            420                 425                 430

Leu Lys Glu Glu Trp Ser Leu Phe Lys Glu Gln Lys Lys Asn Phe Glu
        435                 440                 445

Arg Glu Arg Arg Ser Phe Thr Glu Ala Ala Ile Arg Leu Gly Leu Glu
        450                 455                 460

Arg Lys Ala Phe Glu Glu Glu Arg Ala Ser Trp Val Lys Gln Gln Phe
465                 470                 475                 480

Leu Asn Met Thr Thr Phe Asp His Gln Asn Ser Glu Asn Val Lys Leu
                485                 490                 495

Phe Ser Ala Phe Ser Gly Ser Ser Asp Pro Asp Asn Leu Ile Val His
            500                 505                 510

Pro Arg Pro Arg Gln Lys Lys Pro His Ser Val Ala Asn Gly Val Pro
        515                 520                 525

Ala Cys Thr Ser Lys Leu Ala Lys Ser Leu Pro Thr Ser Pro Ser Asp
    530                 535                 540

Phe Cys Pro Ser Arg Ser Cys Val Ser Glu His Ser Pro Val Ser Ala
545                 550                 555                 560

Leu Thr Val Thr Pro Glu Glu Thr Lys Pro Asn Glu Val Gly Arg Glu
                565                 570                 575

Ser Thr Asp Gln Lys Trp Ser Val Val Ser Arg Pro Ser Ser Arg Glu
            580                 585                 590

Gly Cys Tyr Gly Gly Cys Ser Ser Ala Tyr Thr Ser Ser His Val Glu
        595                 600                 605

Arg Asp Asp Leu Pro
    610

<210> SEQ ID NO 5
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 5
cgtaggagag tgacaggagc tg                                              22

<210> SEQ ID NO 6
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 6
ggttatcgag tttttctaca tgac                                            24

<210> SEQ ID NO 7
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 7
cgtaggagag tgacaggagc tg                                              22

<210> SEQ ID NO 8
<211> LENGTH: 23
<212> TYPE: DNA
```

```
<213> ORGANISM: Artificial
<220> FEATURE:
<223> OTHER INFORMATION: an artificially synthesized primer sequence

<400> SEQUENCE: 8
ttcctgtttt tgcactgtag ctg                                              23
```

What is claimed is:

1. An isolated and purified polynucleotide selected from the group consisting of:
   (a) a polynucleotide encoding a protein consisting of the amino acid sequence of SEQ ID NO: 2; and
   (b) a polynucleotide consisting of the nucleotide sequence set forth at position 80 to 1927 in SEQ ID NO: 1.

2. A vector into which the polynucleotide of claim 1 is inserted.

3. An isolated and purified host cell to which the vector of claim 1 is introduced.

4. A method for producing the polypeptide encoded by the polynucleotide of claim 1, comprising the steps of culturing a host cell expressively carrying either said polynucleotide or a vector into which said polynucleotide is inserted, and recovering the produced polypeptide from said host cell or culture supematant thereof.

5. The polynucleotide of claim 1, wherein said polynucleotide is the polynucleotide of (a).

6. The polynucleotide of claim 1, wherein said polynucleotide is the polynucleotide of (b).

* * * * *

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

At column 6, line 10, delete "Functional" and insert therefor --Junctional--.

At column 11, line 7, delete "MADIP-M" and insert therefor --mADIP-M--.

At column 13, line 55, delete "acids" and insert therefor --acid-- and delete "the an" and insert therefor --an--.

At column 14, line 57, delete "Examples" and insert therefor --Example--.

At column 18, line 3, delete "ascites is" and insert therefor --ascites are--.

At column 19, line 15, delete "myocaroditis" and insert therefor --myocarditis--; and line 63, delete "myocaroditis" and insert therefor --myocarditis--.

At column 20, line 52, delete "DNAS" and insert therefor --DNAs--.

At column 25, line 34, delete "nectin-2α-AC-L cells" and insert therefor --nectin-2α-ΔC-L cells--.

At column 26, line 43, delete "MADIP" and insert therefor --mADIP--.

At column 28, line 50, delete "MBP-MADIP" and insert therefor --MBP-mADIP--.

At column 30, line 16, delete "j. Cell Biol." and insert therefor --J. Cell Biol.--; and lines 34-35, delete "nectin-2α-αC-L cells" and insert therefor --nectin-2α-ΔC-L cells--.

At column 31, line 2, delete "concentrated" and insert therefor --concentrate--.

At column 33, lines 41-42, delete "2 mM Ca" and insert therefor --2 mM Ca$^{2+}$--.

UNITED STATES PATENT AND TRADEMARK OFFICE
CERTIFICATE OF CORRECTION

PATENT NO.         : 7,364,876 B2
APPLICATION NO. : 10/644084
DATED                 : April 29, 2008
INVENTOR(S)       : Takai et al.

It is certified that error appears in the above-identified patent and that said Letters Patent is hereby corrected as shown below:

At column 35 through column 54, please delete the sequence listing and insert therefor the following sequence listing:

```
                         SEQUENCE LISTING

<110>   EISAI CO., LTD.

<120>   ADIP PROTEIN AND USE THEREOF

<130>   2144.0100000

<140>   US 10/644,084
  <141>   2003-08-20

<150>   JP 2002-284263
  <151>   2002-09-27

<160>   9

<170>   PatentIn version 3.3
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
<210>  1
<211>  2692
<212>  DNA
<213>  Mus musculus

<220>
<221>  CDS
<222>  (80)..(1927)
<223>  /note="afadin-and alpha-actinin-binding protein"

<400>  1
cgtaggagag tgacaggagc tgttgtaagc gtcgcagcac tgagccgcct cctcaggtat      60
cctggctctg gaacttgct atg gga gat tgg atg act gtg aca gat cca gtt     112
                    Met Gly Asp Trp Met Thr Val Thr Asp Pro Val
                     1               5                      10 ctg tgt aca gaa aac aaa aat ctc tct caa tat acc tca gaa aca aag     160
Leu Cys Thr Glu Asn Lys Asn Leu Ser Gln Tyr Thr Ser Glu Thr Lys
             15                  20                  25 atg tct ccg tcc agt ttg tac tcc cag caa gtt ctg tgc tct tca gta     208
Met Ser Pro Ser Ser Leu Tyr Ser Gln Gln Val Leu Cys Ser Ser Val
         30                  35                  40 cct tta tcc aaa aac gtg cat ggt gtt ttc ggt gtc ttc tgc aca gga     256
Pro Leu Ser Lys Asn Val His Gly Val Phe Gly Val Phe Cys Thr Gly
     45                  50                  55
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
gag aac att gaa caa agt att tcc tat ctt gat cag gag ctg acc acc    304
Glu Asn Ile Glu Gln Ser Ile Ser Tyr Leu Asp Gln Glu Leu Thr Thr
 60              65                  70                  75 ttc ggg ttt cct tcc ttg tat gaa gaa tcc aaa agt aaa gag gca aag    352
Phe Gly Phe Pro Ser Leu Tyr Glu Glu Ser Lys Ser Lys Glu Ala Lys
             80                  85                  90 aga gaa tta aat ata gtc gct gtt ctg aac tgt atg aac gag ctg ctc    400
Arg Glu Leu Asn Ile Val Ala Val Leu Asn Cys Met Asn Glu Leu Leu
             95                  100                 105 gtg ctt cag cgg aag aac ctg ctg gcc cag gag agc gtg gag aca cag    448
Val Leu Gln Arg Lys Asn Leu Leu Ala Gln Glu Ser Val Glu Thr Gln
             110                 115                 120 aac ttg aag ctg ggc agt gac atg gac cac ctg cag agc tgc tac gcc    496
Asn Leu Lys Leu Gly Ser Asp Met Asp His Leu Gln Ser Cys Tyr Ala
     125                 130                 135
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

| | | | | | | | | | | | | | | | |
|---|---|---|---|---|---|---|---|---|---|---|---|---|---|---|---|
| aaa | ctt | aag | gag | cag | ttg | gaa | acg | tcc | agg | cgg | gag | atg | atc | ggg | ctt | 544 |
| Lys | Leu | Lys | Glu | Gln | Leu | Glu | Thr | Ser | Arg | Arg | Glu | Met | Ile | Gly | Leu |
| 140 | | | | 145 | | | | | 150 | | | | | 155 | |
| caa | gag | aga | gac | agg | cag | ctg | cag | tgc | aag | aac | agg | agt | ttg | cat | cag | 592 |
| Gln | Glu | Arg | Asp | Arg | Gln | Leu | Gln | Cys | Lys | Asn | Arg | Ser | Leu | His | Gln |
| | | | 160 | | | | | 165 | | | | | 170 | | |
| ctc | ctg | aag | aat | gag | aaa | gat | gag | gta | caa | aaa | tta | caa | aat | atc | ata | 640 |
| Leu | Leu | Lys | Asn | Glu | Lys | Asp | Glu | Val | Gln | Lys | Leu | Gln | Asn | Ile | Ile |
| | | 175 | | | | | 180 | | | | | 185 | | | |
| gcc | agc | cgg | gct | act | cag | tat | aat | cat | gat | gtg | aag | agg | aag | gag | cgt | 688 |
| Ala | Ser | Arg | Ala | Thr | Gln | Tyr | Asn | His | Asp | Val | Lys | Arg | Lys | Glu | Arg |
| | | 190 | | | | | 195 | | | | | 200 | | | |
| gaa | tat | aat | aag | cta | aag | gag | cgc | ctg | cat | cag | ctc | gtt | atg | aac | aag | 736 |
| Glu | Tyr | Asn | Lys | Leu | Lys | Glu | Arg | Leu | His | Gln | Leu | Val | Met | Asn | Lys |
| | | 205 | | | | | 210 | | | | | 215 | | | |
| aag | gat | aaa | aac | ata | gcc | atg | gat | gtt | tta | aat | tat | gtg | ggt | cga | gct | 784 |
| Lys | Asp | Lys | Asn | Ile | Ala | Met | Asp | Val | Leu | Asn | Tyr | Val | Gly | Arg | Ala |
| 220 | | | | 225 | | | | | 230 | | | | | 235 | |

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
gat ggc aaa cga ggc tca tgg agg act gac aaa aca gaa gcc agg aat     832
Asp Gly Lys Arg Gly Ser Trp Arg Thr Asp Lys Thr Glu Ala Arg Asn
            240             245             250 gaa gat gag atg tac aaa att ctg ttg aat gat tat gag tac cgc cag     880
Glu Asp Glu Met Tyr Lys Ile Leu Leu Asn Asp Tyr Glu Tyr Arg Gln
            255             260             265 aag cag atc ctg atg gag aac gcg gag ctg aag aag gtc ctc cag cag     928
Lys Gln Ile Leu Met Glu Asn Ala Glu Leu Lys Lys Val Leu Gln Gln
            270             275             280 atg aag aag gag atg atc tct ctc ctg tct cct cag aag aag aag ccc     976
Met Lys Lys Glu Met Ile Ser Leu Leu Ser Pro Gln Lys Lys Lys Pro
            285             290             295 agg gaa aga gca gag gac ggc aca ggc act gtt gct atc tcc gat ata    1024
Arg Glu Arg Ala Glu Asp Gly Thr Gly Thr Val Ala Ile Ser Asp Ile
300             305             310             315 gaa gat gac tct ggg gaa ctg agc aga gac agc gtg tgg ggc ctt tcc    1072
Glu Asp Asp Ser Gly Glu Leu Ser Arg Asp Ser Val Trp Gly Leu Ser
            320             325             330
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
tgt gac act gtg aga gag cag ctg aca aac agc atc agg aaa cag tgg      1120
Cys Asp Thr Val Arg Glu Gln Leu Thr Asn Ser Ile Arg Lys Gln Trp
            335                 340                 345 aga att ttg aaa agt cat gta gaa aaa ctc gat aac caa gct tcg aag      1168
Arg Ile Leu Lys Ser His Val Glu Lys Leu Asp Asn Gln Ala Ser Lys
            350                 355                 360 gta cac tca gag ggc ctt aat gag gag gac gtc atc tca cga caa gac      1216
Val His Ser Glu Gly Leu Asn Glu Glu Asp Val Ile Ser Arg Gln Asp
            365                 370                 375 cat gag caa gag act gag aaa ctg gag ctg gag att gag cgg tgt aaa      1264
His Glu Gln Glu Thr Glu Lys Leu Glu Leu Glu Ile Glu Arg Cys Lys
380                 385                 390                 395 gag atg atc aag gct cag cag cag ctc tta cag cag cag ctg gcc acc      1312
Glu Met Ile Lys Ala Gln Gln Gln Leu Leu Gln Gln Gln Leu Ala Thr
                400                 405                 410 acg tgt gat gat gac acc acc tca ctg ttg cga gac tgt tac ttg ctg      1360
Thr Cys Asp Asp Asp Thr Thr Ser Leu Leu Arg Asp Cys Tyr Leu Leu
                415                 420                 425
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
gaa gaa aag gaa cgc ctt aaa gaa gag tgg acc ctt ttt aaa gag caa      1408
Glu Glu Lys Glu Arg Leu Lys Glu Glu Trp Thr Leu Phe Lys Glu Gln
        430                 435                 440 aaa aag aat ttt gag aga gaa agg cga agc ttt aca gaa gct gcc att      1456
Lys Lys Asn Phe Glu Arg Glu Arg Arg Ser Phe Thr Glu Ala Ala Ile
        445                 450                 455 cga ttg ggg ttg gag aga aag gcg ttt gaa gaa gag cga gcc agc tgg      1504
Arg Leu Gly Leu Glu Arg Lys Ala Phe Glu Glu Glu Arg Ala Ser Trp
460                 465                 470                 475 gta aag cag cag ttt tta aac atg acg aac ttt gac cac cag aac tca      1552
Val Lys Gln Gln Phe Leu Asn Met Thr Asn Phe Asp His Gln Asn Ser
                480                 485                 490 gaa aat gtg aaa ctt ttc agt gcc ttc tca gga agt tct gat cca gac      1600
Glu Asn Val Lys Leu Phe Ser Ala Phe Ser Gly Ser Ser Asp Pro Asp
                495                 500                 505 aat ctt ata gtc cac tca cgg cca cgg caa aag aag cta cac agt gtg      1648
Asn Leu Ile Val His Ser Arg Pro Arg Gln Lys Lys Leu His Ser Val
                510                 515                 520
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
gct aat ggg gtg cca gct tgc aca tca aaa ctg act aaa tct ctt cct    1696
Ala Asn Gly Val Pro Ala Cys Thr Ser Lys Leu Thr Lys Ser Leu Pro
    525                 530                 535 gcc tca cct tct act tca gac ttt cgc cag aca cat tca tgt gtg tct    1744
Ala Ser Pro Ser Thr Ser Asp Phe Arg Gln Thr His Ser Cys Val Ser
540                 545                 550                 555 gaa cac agt tcc atc agt gtg ctg aat ata act cct gaa gaa agt aaa    1792
Glu His Ser Ser Ile Ser Val Leu Asn Ile Thr Pro Glu Glu Ser Lys
                560                 565                 570 cca agt gag gtt gca aga gaa agc acg gat cag aag tgg agc gtg cag    1840
Pro Ser Glu Val Ala Arg Glu Ser Thr Asp Gln Lys Trp Ser Val Gln
        575                 580                 585 tcg agg ccc agc tcg cgg gag ggg tgc tac agc gga tgc tcc tcg gcc    1888
Ser Arg Pro Ser Ser Arg Glu Gly Cys Tyr Ser Gly Cys Ser Ser Ala
            590                 595                 600
```

UNITED STATES PATENT AND TRADEMARK OFFICE
CERTIFICATE OF CORRECTION

PATENT NO.          : 7,364,876 B2
APPLICATION NO. : 10/644084
DATED                    : April 29, 2008
INVENTOR(S)         : Takai et al.

It is certified that error appears in the above-identified patent and that said Letters Patent is hereby corrected as shown below:

```
ttc agg agc gct cac ggg gac cga gat gac tta cct taa atgtgcgggc      1937
Phe Arg Ser Ala His Gly Asp Arg Asp Asp Leu Pro
    605                 610                 615 tgcagtgctg ttcccagatg tgcgctagag gagttgacac agggtgtagc ataaagtcag   1997
tcgtctaact taagatgctc agagttgttt gtttggactt cgctgtcttc cccaaagag    2057 ctgaaatgct aagctactta aaaggatgca aagctttggt tgtgtgttag taacagaagc   2117
ccctggctct gtgactgcag gaatgcatgg cgtttggatg gaaacagaag cgctggaatg   2177
attgcctcgc caggtaccga gaagagcact tttagggact ggttcctgta aacattaaat   2237
attcgtccca agtgtggttg gcattggaag tgtagccttt acttgaatgt atactgtaga   2297
tttttaacaa agcaggttct atatttatta tgtttagtgt gattttggga ttacctcttt   2357
catatgtttt gtgtctgtac ataaatatac atgactatgt taagaggctt taaggtttaa   2417
aaacttcaca ccatgcttga gtatagcatt tcatgccaat taaaatgttt tcagtggcat   2477
```

UNITED STATES PATENT AND TRADEMARK OFFICE
CERTIFICATE OF CORRECTION

PATENT NO.        : 7,364,876 B2
APPLICATION NO.   : 10/644084
DATED             : April 29, 2008
INVENTOR(S)       : Takai et al.

It is certified that error appears in the above-identified patent and that said Letters Patent is hereby corrected as shown below:

```
ggtgtttaca gaggttagga ccactgccac atgacagtta agactttatt tttaagccat    2537
ctgggcaata aaaattcaaa gcccttcat aagctgagtt cagataacta gaactactaa    2597
cgttacattt ttgagatttt taaagcattg tattttattt tatatatgtg aatgttataa   2657
tttctaagag gaatattgat tatggagtaa tgggg                              2692

<210>  2
<211>  615
<212>  PRT
<213>  Mus musculus

<400>  2

Met Gly Asp Trp Met Thr Val Thr Asp Pro Val Leu Cys Thr Glu Asn
1               5                   10                  15

Lys Asn Leu Ser Gln Tyr Thr Ser Glu Thr Lys Met Ser Pro Ser Ser
            20                  25                  30

Leu Tyr Ser Gln Gln Val Leu Cys Ser Ser Val Pro Leu Ser Lys Asn
        35                  40                  45
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Val His Gly Val Phe Gly Val Phe Cys Thr Gly Glu Asn Ile Glu Gln
    50              55              60

Ser Ile Ser Tyr Leu Asp Gln Glu Leu Thr Thr Phe Gly Phe Pro Ser
65              70              75              80

Leu Tyr Glu Glu Ser Lys Ser Lys Glu Ala Lys Arg Glu Leu Asn Ile
                85              90              95

Val Ala Val Leu Asn Cys Met Asn Glu Leu Leu Val Leu Gln Arg Lys
            100             105             110

Asn Leu Leu Ala Gln Glu Ser Val Glu Thr Gln Asn Leu Lys Leu Gly
            115             120             125

Ser Asp Met Asp His Leu Gln Ser Cys Tyr Ala Lys Leu Lys Glu Gln
        130             135             140

Leu Glu Thr Ser Arg Arg Glu Met Ile Gly Leu Gln Glu Arg Asp Arg
145             150             155             160
```

UNITED STATES PATENT AND TRADEMARK OFFICE
CERTIFICATE OF CORRECTION

PATENT NO.      : 7,364,876 B2
APPLICATION NO. : 10/644084
DATED           : April 29, 2008
INVENTOR(S)     : Takai et al.

It is certified that error appears in the above-identified patent and that said Letters Patent is hereby corrected as shown below:

```
Gln Leu Gln Cys Lys Asn Arg Ser Leu His Gln Leu Leu Lys Asn Glu
                165             170                 175

Lys Asp Glu Val Gln Lys Leu Gln Asn Ile Ile Ala Ser Arg Ala Thr
            180             185                 190

Gln Tyr Asn His Asp Val Lys Arg Lys Glu Arg Glu Tyr Asn Lys Leu
        195             200                 205

Lys Glu Arg Leu His Gln Leu Val Met Asn Lys Lys Asp Lys Asn Ile
    210             215                 220

Ala Met Asp Val Leu Asn Tyr Val Gly Arg Ala Asp Gly Lys Arg Gly
225             230                 235                     240

Ser Trp Arg Thr Asp Lys Thr Glu Ala Arg Asn Glu Asp Glu Met Tyr
                245             250                 255

Lys Ile Leu Leu Asn Asp Tyr Glu Tyr Arg Gln Lys Gln Ile Leu Met
            260             265                 270
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Glu Asn Ala Glu Leu Lys Lys Val Leu Gln Gln Met Lys Lys Glu Met
            275             280             285

Ile Ser Leu Leu Ser Pro Gln Lys Lys Lys Pro Arg Glu Arg Ala Glu
            290             295             300

Asp Gly Thr Gly Thr Val Ala Ile Ser Asp Ile Glu Asp Asp Ser Gly
305             310             315             320

Glu Leu Ser Arg Asp Ser Val Trp Gly Leu Ser Cys Asp Thr Val Arg
                325             330             335

Glu Gln Leu Thr Asn Ser Ile Arg Lys Gln Trp Arg Ile Leu Lys Ser
            340             345             350

His Val Glu Lys Leu Asp Asn Gln Ala Ser Lys Val His Ser Glu Gly
            355             360             365

Leu Asn Glu Glu Asp Val Ile Ser Arg Gln Asp His Glu Gln Glu Thr
    370             375             380
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Glu Lys Leu Glu Leu Glu Ile Glu Arg Cys Lys Glu Met Ile Lys Ala
385             390             395             400

Gln Gln Gln Leu Leu Gln Gln Leu Ala Thr Thr Cys Asp Asp Asp
            405             410             415

Thr Thr Ser Leu Leu Arg Asp Cys Tyr Leu Leu Glu Glu Lys Glu Arg
            420             425             430

Leu Lys Glu Glu Trp Thr Leu Phe Lys Glu Gln Lys Lys Asn Phe Glu
        435             440             445

Arg Glu Arg Arg Ser Phe Thr Glu Ala Ala Ile Arg Leu Gly Leu Glu
        450             455             460

Arg Lys Ala Phe Glu Glu Glu Arg Ala Ser Trp Val Lys Gln Gln Phe
465             470             475             480

Leu Asn Met Thr Asn Phe Asp His Gln Asn Ser Glu Asn Val Lys Leu
            485             490             495
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Phe Ser Ala Phe Ser Gly Ser Ser Asp Pro Asp Asn Leu Ile Val His
            500             505             510

Ser Arg Pro Arg Gln Lys Lys Leu His Ser Val Ala Asn Gly Val Pro
            515             520             525

Ala Cys Thr Ser Lys Leu Thr Lys Ser Leu Pro Ala Ser Pro Ser Thr
    530             535             540

Ser Asp Phe Arg Gln Thr His Ser Cys Val Ser Glu His Ser Ser Ile
545             550             555             560

Ser Val Leu Asn Ile Thr Pro Glu Glu Ser Lys Pro Ser Glu Val Ala
                565             570             575

Arg Glu Ser Thr Asp Gln Lys Trp Ser Val Gln Ser Arg Pro Ser Ser
            580             585             590

Arg Glu Gly Cys Tyr Ser Gly Cys Ser Ser Ala Phe Arg Ser Ala His
            595             600             605
```

UNITED STATES PATENT AND TRADEMARK OFFICE
CERTIFICATE OF CORRECTION

| | |
|---|---|
| PATENT NO. | : 7,364,876 B2 |
| APPLICATION NO. | : 10/644084 |
| DATED | : April 29, 2008 |
| INVENTOR(S) | : Takai et al. |

It is certified that error appears in the above-identified patent and that said Letters Patent is hereby corrected as shown below:

```
     Gly Asp Arg Asp Asp Leu Pro
         610                 615

<210>  3
<211>  3195
<212>  DNA
<213>  Rattus norvegicus

<220>
<221>  CDS
<222>  (79)..(1920)

<220>
<221>  misc_feature
<222>  (2422)..(2422)
<223>  "n"=any one base of a, t, c, or g <400>  3
gtaggagagt gacaggagct gttgtgcatg ccccagcact gaactgcctt ctcagggacc     60
ctggctctgg gactggct atg gga gat tgg atg act gtt aca gat cca gtt    111
                    Met Gly Asp Trp Met Thr Val Thr Asp Pro Val
                     1               5                  10 ctg tgt aca gaa aac aaa aat ctc tct caa tat acc tca gaa aca aag    159
Leu Cys Thr Glu Asn Lys Asn Leu Ser Gln Tyr Thr Ser Glu Thr Lys
             15                  20                  25
```

UNITED STATES PATENT AND TRADEMARK OFFICE
CERTIFICATE OF CORRECTION

PATENT NO.        : 7,364,876 B2
APPLICATION NO.   : 10/644084
DATED             : April 29, 2008
INVENTOR(S)       : Takai et al.

It is certified that error appears in the above-identified patent and that said Letters Patent is hereby corrected as shown below:

```
atg tct ccg tca agt tta tac tcg cag caa gta ctg tgc tct gca aca        207
Met Ser Pro Ser Ser Leu Tyr Ser Gln Gln Val Leu Cys Ser Ala Thr
        30                      35                  40 cct tta tcc aag aat gtg cat ggt gtt ttc agt gcc ttc tgc aca gga        255
Pro Leu Ser Lys Asn Val His Gly Val Phe Ser Ala Phe Cys Thr Gly
        45                      50                  55 gag aac atc gaa cag agt att tcg tat ctt gat cag gaa ctg act acc        303
Glu Asn Ile Glu Gln Ser Ile Ser Tyr Leu Asp Gln Glu Leu Thr Thr
60                      65                  70                  75 ttc ggt ttc cct tcc ttg tat gaa gaa tcc aaa agt aag gag gcg aag        351
Phe Gly Phe Pro Ser Leu Tyr Glu Glu Ser Lys Ser Lys Glu Ala Lys
                80                      85                  90 cga gag tta agt ata gtt gct ctt ctg aac tgc atg aat gag ctg ctt        399
Arg Glu Leu Ser Ile Val Ala Leu Leu Asn Cys Met Asn Glu Leu Leu
                95                     100                 105 gtg ctt cag cgg aag aac ctc ctg gcc cag gaa agc gtg gag aca cag        447
Val Leu Gln Arg Lys Asn Leu Leu Ala Gln Glu Ser Val Glu Thr Gln
        110                     115                 120 aat ctg aag ctg ggc agt gac atg gac cac ctg cag agc tgc tac gcc        495
Asn Leu Lys Leu Gly Ser Asp Met Asp His Leu Gln Ser Cys Tyr Ala
        125                     130                 135
```

UNITED STATES PATENT AND TRADEMARK OFFICE
CERTIFICATE OF CORRECTION

PATENT NO.        : 7,364,876 B2
APPLICATION NO.   : 10/644084
DATED             : April 29, 2008
INVENTOR(S)       : Takai et al.

It is certified that error appears in the above-identified patent and that said Letters Patent is hereby corrected as shown below:

```
aaa ctt aag gaa cag ttg gag gcc tcc agg cga gag atg atc agc ctt        543
Lys Leu Lys Glu Gln Leu Glu Ala Ser Arg Arg Glu Met Ile Ser Leu
140             145             150             155 cag gag aga gac aga cag cta cag tgc aaa aac agg aat ttg cat cag        591
Gln Glu Arg Asp Arg Gln Leu Gln Cys Lys Asn Arg Asn Leu His Gln
            160             165             170 ctc ctg aaa aac gag aaa gaa gag gta caa aaa tta caa aat atc ata        639
Leu Leu Lys Asn Glu Lys Glu Glu Val Gln Lys Leu Gln Asn Ile Ile
            175             180             185 gcc agt cgg gct act cag tat aat cat gat gtg aag aga aag gag cgg        687
Ala Ser Arg Ala Thr Gln Tyr Asn His Asp Val Lys Arg Lys Glu Arg
            190             195             200 gag tac aat aaa ctg aag gag cgt ctg cat cag ctt gtt atg aac aag        735
Glu Tyr Asn Lys Leu Lys Glu Arg Leu His Gln Leu Val Met Asn Lys
        205             210             215 aag gat aaa aat ata gcc atg gac gtt tta aat tac gtg ggc cga gtg        783
Lys Asp Lys Asn Ile Ala Met Asp Val Leu Asn Tyr Val Gly Arg Val
220             225             230             235 gat gga aag cga ggc tcc tgg agg act gat aaa aca gaa gcc agg aat        831
Asp Gly Lys Arg Gly Ser Trp Arg Thr Asp Lys Thr Glu Ala Arg Asn
            240             245             250
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
gaa gat gaa atg tac aaa att ctg ctg aat gat tat gag tac cgc cag     879
Glu Asp Glu Met Tyr Lys Ile Leu Leu Asn Asp Tyr Glu Tyr Arg Gln
            255                 260                 265 aag cag atc ctg ctg gag aat gcg gag ctg aag aag gtc ctc cag cag     927
Lys Gln Ile Leu Leu Glu Asn Ala Glu Leu Lys Lys Val Leu Gln Gln
            270                 275                 280 atg aag aaa gag atg atc tct ctc ctt tct cct caa aag aag aaa ccc     975
Met Lys Lys Glu Met Ile Ser Leu Leu Ser Pro Gln Lys Lys Lys Pro
            285                 290                 295 aga gaa aga gca gag gac agc aca ggc act gtt gtc atc tcc gat gta    1023
Arg Glu Arg Ala Glu Asp Ser Thr Gly Thr Val Val Ile Ser Asp Val
300             305                 310                 315 gaa gac gac gct ggg gag ctg agc aga gat ggt gtg tgg agc ctt tcc    1071
Glu Asp Asp Ala Gly Glu Leu Ser Arg Asp Gly Val Trp Ser Leu Ser
                320                 325                 330 tgt gac act gtc agg gag cag ctt aca aac agc atc agg aag cag tgg    1119
Cys Asp Thr Val Arg Glu Gln Leu Thr Asn Ser Ile Arg Lys Gln Trp
            335                 340                 345 aga att ctg aaa agc cat gtg gaa aaa ctt gat aac caa gct tca aag    1167
Arg Ile Leu Lys Ser His Val Glu Lys Leu Asp Asn Gln Ala Ser Lys
            350                 355                 360
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
gta cac tca gag ggc ttt cat gaa gag gac gtc atc tca cga caa gac    1215
Val His Ser Glu Gly Phe His Glu Glu Asp Val Ile Ser Arg Gln Asp
    365                 370                 375 cat gag caa gag act gag aaa ctg gag ctg gag att gag cgg tgt aaa    1263
His Glu Gln Glu Thr Glu Lys Leu Glu Leu Glu Ile Glu Arg Cys Lys
380                 385                 390                 395 gag atg atc aag gct cag cag cag ctc tta cag caa cag ctg gcc act    1311
Glu Met Ile Lys Ala Gln Gln Gln Leu Leu Gln Gln Gln Leu Ala Thr
                    400                 405                 410 gcg tgt gat gac gac acc acc tca ctg ttg cga gac tgt tac ttg ctt    1359
Ala Cys Asp Asp Asp Thr Thr Ser Leu Leu Arg Asp Cys Tyr Leu Leu
                415                 420                 425 gaa gaa aag gaa cgc ctt aaa gaa gag tgg tcc ctt ttt aaa gag caa    1407
Glu Glu Lys Glu Arg Leu Lys Glu Glu Trp Ser Leu Phe Lys Glu Gln
            430                 435                 440 aaa aag aat ttt gag aga gaa aga cga agc ttt aca gaa gct gct att    1455
Lys Lys Asn Phe Glu Arg Glu Arg Arg Ser Phe Thr Glu Ala Ala Ile
        445                 450                 455 cgc ttg ggg ttg gag aga aag gcg ttt gag gaa gag cga gcc agc tgg    1503
Arg Leu Gly Leu Glu Arg Lys Ala Phe Glu Glu Glu Arg Ala Ser Trp
460                 465                 470                 475
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
gtg aag cag cag ttt tta aac atg acg acc ttt gat cac cag aac tca     1551
Val Lys Gln Gln Phe Leu Asn Met Thr Thr Phe Asp His Gln Asn Ser
            480                 485                 490 gaa aat gtg aaa ctt ttc agt gcc ttt tca gga agt tct gat cca gac     1599
Glu Asn Val Lys Leu Phe Ser Ala Phe Ser Gly Ser Ser Asp Pro Asp
            495                 500                 505 aat ctt ata gtc cac cca cgg cca cgg caa aag aag cca cac agt gtc     1647
Asn Leu Ile Val His Pro Arg Pro Arg Gln Lys Lys Pro His Ser Val
            510                 515                 520 gct aat ggg gtg cca gct tgc aca tcc aaa ctg gct aag tct ctt ccg     1695
Ala Asn Gly Val Pro Ala Cys Thr Ser Lys Leu Ala Lys Ser Leu Pro
            525                 530                 535 acc tca cct tca gac ttc tgc ccg tct cgc tca tgt gtg tct gag cac     1743
Thr Ser Pro Ser Asp Phe Cys Pro Ser Arg Ser Cys Val Ser Glu His
540                 545                 550                 555 agt ccc gtc agt gcg ctg act gtg act cct gaa gaa acc aaa ccg aat     1791
Ser Pro Val Ser Ala Leu Thr Val Thr Pro Glu Glu Thr Lys Pro Asn
            560                 565                 570 gag gtt gga aga gaa agt acg gac cag aag tgg agc gtg gtg tcc aga     1839
Glu Val Gly Arg Glu Ser Thr Asp Gln Lys Trp Ser Val Val Ser Arg
            575                 580                 585
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
      ccc agc tcc cgg gag ggt tgc tac ggt gga tgc tcc tcg gcc tac aca    1887
      Pro Ser Ser Arg Glu Gly Cys Tyr Gly Gly Cys Ser Ser Ala Tyr Thr
              590                 595                 600 agc tcc cac gtg gaa cga gat gac tta cca tag gtgctcgggc tgcagcgctg   1940
      Ser Ser His Val Glu Arg Asp Asp Leu Pro
              605                 610 tcctggagtg catgagagga attgacacgg ggtgtagcat aaagtcagcc atctaccgta   2000
agatgtcgga gttatttgtt tggacttccc agtctttccc caaagagctg aaacgcttta   2060
gaggatgcga aagctttggc tgtgtgttag taacagaagc ctctggctct gtgagtaaag   2120
gaatgtatgg tgtttggtgg gaaacaaaag cacgagaatg atttcctctt ccgggtactg   2180
agaatagcac ttttagggac tgattcttgt aaacattaaa tttttgtccc aagtatggtt   2240
ggcattggaa gtttagtctt tacttgaatg tacactgtag atttttaaca aagcagttct   2300
atatttatta tgtttagtgt gattttggga ttacctcttt catatgtttt ctgcctgtac   2360
ataaatatac atgactatgt taagaggctt taaggtttaa aaatttcaca ccatgctcga   2420
gnatagcatt tcatgccaat taaaatgttt tcagtggcat ggtgtttaca gatgtgttag   2480
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
gaccactgcc acatgacagt taagatttta tttttaagcc atttgggcaa taaaaattca   2540
aagccacttc ataagctaag ttcagatagc taaaactact aacattacat ttttgagatt   2600
tataaagcat tatattttat tttatatatg tgactgttat aatttctaag aggaatgtgg   2660
attatgaagc aatgggggaa agacagaagt gactaatagt gcaagagcat tgggtgaagg   2720
gacggctgat gaggatatgg gagacctggg tggtgatctt ttccttaccg acggtgcggt   2780
gcggcgatct ctgtaccgcc agggctttct atcattgcca atactttgt aattaaagag    2840 attttcaact acataccact actaaagtaa gacagtgtaa aactttggct tttgtaattg   2900
acactctgga cactggtgtg ttgttcattt ctagaacaat cgtaggctct tttctctgtt   2960
tctgctgcat gtttcttcat gagaagtatg ttactattga cagtaatgac actgacagtg   3020
actgtagacg taggcccaga cttctcctgg gtggattttc atccagcagc ttttaagtgc   3080
ctcgccctgc tcgtctctgc acatagccgc cgacacaagc cctgcttga tgatgcagat    3140 agtccatctg cctttctctc cccttgccct gctatgactg ttgcattaaa ttcat         3195
```

UNITED STATES PATENT AND TRADEMARK OFFICE
CERTIFICATE OF CORRECTION

PATENT NO.        : 7,364,876 B2
APPLICATION NO. : 10/644084
DATED             : April 29, 2008
INVENTOR(S)      : Takai et al.

It is certified that error appears in the above-identified patent and that said Letters Patent is hereby corrected as shown below:

```
<210>  4
<211>  613
<212>  PRT
<213>  Rattus norvegicus

<400>  4

Met Gly Asp Trp Met Thr Val Thr Asp Pro Val Leu Cys Thr Glu Asn
1               5                   10                  15

Lys Asn Leu Ser Gln Tyr Thr Ser Glu Thr Lys Met Ser Pro Ser Ser
                20                  25                  30

Leu Tyr Ser Gln Gln Val Leu Cys Ser Ala Thr Pro Leu Ser Lys Asn
                35                  40                  45

Val His Gly Val Phe Ser Ala Phe Cys Thr Gly Glu Asn Ile Glu Gln
            50                  55                  60

Ser Ile Ser Tyr Leu Asp Gln Glu Leu Thr Thr Phe Gly Phe Pro Ser
65                  70                  75                  80

Leu Tyr Glu Glu Ser Lys Ser Lys Glu Ala Lys Arg Glu Leu Ser Ile
                85                  90                  95
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Val Ala Leu Leu Asn Cys Met Asn Glu Leu Leu Val Leu Gln Arg Lys
                100             105             110

Asn Leu Leu Ala Gln Glu Ser Val Glu Thr Gln Asn Leu Lys Leu Gly
                115             120             125

Ser Asp Met Asp His Leu Gln Ser Cys Tyr Ala Lys Leu Lys Glu Gln
        130             135             140

Leu Glu Ala Ser Arg Arg Glu Met Ile Ser Leu Gln Glu Arg Asp Arg
145             150             155             160

Gln Leu Gln Cys Lys Asn Arg Asn Leu His Gln Leu Leu Lys Asn Glu
                165             170             175

Lys Glu Glu Val Gln Lys Leu Gln Asn Ile Ile Ala Ser Arg Ala Thr
                180             185             190

Gln Tyr Asn His Asp Val Lys Arg Lys Glu Arg Glu Tyr Asn Lys Leu
            195             200             205
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Lys Glu Arg Leu His Gln Leu Val Met Asn Lys Lys Asp Lys Asn Ile
    210             215                 220

Ala Met Asp Val Leu Asn Tyr Val Gly Arg Val Asp Gly Lys Arg Gly
225                 230                 235                 240

Ser Trp Arg Thr Asp Lys Thr Glu Ala Arg Asn Glu Asp Glu Met Tyr
                245                 250                 255

Lys Ile Leu Leu Asn Asp Tyr Glu Tyr Arg Gln Lys Gln Ile Leu Leu
            260                 265                 270

Glu Asn Ala Glu Leu Lys Lys Val Leu Gln Gln Met Lys Lys Glu Met
                275                 280                 285

Ile Ser Leu Leu Ser Pro Gln Lys Lys Lys Pro Arg Glu Arg Ala Glu
            290                 295                 300

Asp Ser Thr Gly Thr Val Val Ile Ser Asp Val Glu Asp Asp Ala Gly
305                 310                 315                 320
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
Glu Leu Ser Arg Asp Gly Val Trp Ser Leu Ser Cys Asp Thr Val Arg
            325                 330                 335

Glu Gln Leu Thr Asn Ser Ile Arg Lys Gln Trp Arg Ile Leu Lys Ser
            340                 345                 350

His Val Glu Lys Leu Asp Asn Gln Ala Ser Lys Val His Ser Glu Gly
            355                 360                 365

Phe His Glu Glu Asp Val Ile Ser Arg Gln Asp His Glu Gln Glu Thr
            370                 375                 380

Glu Lys Leu Glu Leu Glu Ile Glu Arg Cys Lys Glu Met Ile Lys Ala
385                 390                 395                 400

Gln Gln Gln Leu Leu Gln Gln Gln Leu Ala Thr Ala Cys Asp Asp Asp
            405                 410                 415

Thr Thr Ser Leu Leu Arg Asp Cys Tyr Leu Leu Glu Glu Lys Glu Arg
            420                 425                 430
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Leu Lys Glu Glu Trp Ser Leu Phe Lys Glu Gln Lys Lys Asn Phe Glu
        435             440             445

Arg Glu Arg Arg Ser Phe Thr Glu Ala Ala Ile Arg Leu Gly Leu Glu
    450             455             460

Arg Lys Ala Phe Glu Glu Glu Arg Ala Ser Trp Val Lys Gln Gln Phe
465             470             475             480

Leu Asn Met Thr Thr Phe Asp His Gln Asn Ser Glu Asn Val Lys Leu
            485             490             495

Phe Ser Ala Phe Ser Gly Ser Ser Asp Pro Asp Asn Leu Ile Val His
        500             505             510

Pro Arg Pro Arg Gln Lys Lys Pro His Ser Val Ala Asn Gly Val Pro
        515             520             525

Ala Cys Thr Ser Lys Leu Ala Lys Ser Leu Pro Thr Ser Pro Ser Asp
    530             535             540
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
Phe Cys Pro Ser Arg Ser Cys Val Ser Glu His Ser Pro Val Ser Ala
545                 550                 555                 560

Leu Thr Val Thr Pro Glu Glu Thr Lys Pro Asn Glu Val Gly Arg Glu
                565                 570                 575

Ser Thr Asp Gln Lys Trp Ser Val Val Ser Arg Pro Ser Ser Arg Glu
                580                 585                 590

Gly Cys Tyr Gly Gly Cys Ser Ser Ala Tyr Thr Ser Ser His Val Glu
                595                 600                 605

Arg Asp Asp Leu Pro
        610

<210>  5
<211>  22
<212>  DNA
<213>  Artificial Sequence
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
<220>
<223>  an artificially synthesized primer sequence

<400>  5
cgtaggagag tgacaggagc tg                                        22

<210>  6
<211>  24
<212>  DNA
<213>  Artificial Sequence

<220>
<223>  an artificially synthesized primer sequence

<400>  6
ggttatcgag tttttctaca tgac                                      24

<210>  7
<211>  22
<212>  DNA
<213>  Artificial Sequence

<220>
<223>  an artificially synthesized primer sequence
```

UNITED STATES PATENT AND TRADEMARK OFFICE
CERTIFICATE OF CORRECTION

| | |
|---|---|
| PATENT NO. | : 7,364,876 B2 |
| APPLICATION NO. | : 10/644084 |
| DATED | : April 29, 2008 |
| INVENTOR(S) | : Takai et al. |

It is certified that error appears in the above-identified patent and that said Letters Patent is hereby corrected as shown below:

```
<400>  7
cgtaggagag tgacaggagc tg                                              22

<210>  8
<211>  23
<212>  DNA
<213>  Artificial Sequence

<220>
<223>  an artificially synthesized primer sequence

<400>  8
ttcctgtttt tgcactgtag ctg                                             23

<210>  9
<211>  626
<212>  PRT
<213>  Homo sapiens
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
<400>  9

Thr Ser Ser Ser Gly Ile Leu Ala Leu Glu Ile Ala Met Gly Asp Trp
1               5                   10                  15

Met Thr Val Thr Asp Pro Gly Leu Ser Ser Glu Ser Lys Thr Ile Ser
                20                  25                  30

Gln Tyr Thr Ser Glu Thr Lys Met Ser Pro Ser Ser Leu Tyr Ser Gln
            35                  40                  45

Gln Val Leu Cys Ser Ser Ile Pro Leu Ser Lys Asn Val His Ser Phe
        50                  55                  60

Phe Ser Ala Phe Cys Thr Glu Asp Asn Ile Glu Gln Ser Ile Ser Tyr
65                  70                  75                  80

Leu Asp Gln Glu Leu Thr Thr Phe Gly Phe Pro Ser Leu Tyr Glu Glu
                85                  90                  95

Ser Lys Gly Lys Glu Thr Lys Arg Glu Leu Asn Ile Val Ala Val Leu
                100                 105                 110
```

UNITED STATES PATENT AND TRADEMARK OFFICE
CERTIFICATE OF CORRECTION

PATENT NO.        : 7,364,876 B2
APPLICATION NO.   : 10/644084
DATED             : April 29, 2008
INVENTOR(S)       : Takai et al.

It is certified that error appears in the above-identified patent and that said Letters Patent is hereby corrected as shown below:

```
Asn Cys Met Asn Glu Leu Leu Val Leu Gln Arg Lys Asn Leu Leu Ala
        115                 120             125

Gln Glu Asn Val Glu Thr Gln Asn Leu Lys Leu Gly Ser Asp Met Asp
        130                 135             140

His Leu Gln Ser Cys Tyr Ser Lys Leu Lys Glu Gln Leu Glu Thr Ser
145                 150             155                     160

Arg Arg Glu Met Ile Gly Leu Gln Glu Arg Asp Arg Gln Leu Gln Cys
            165                 170                 175

Lys Asn Arg Asn Leu His Gln Leu Leu Lys Asn Glu Lys Asp Glu Val
            180                 185                 190

Gln Lys Leu Gln Asn Ile Ile Ala Ser Arg Ala Thr Gln Tyr Asn His
            195                 200             205

Asp Met Lys Arg Lys Glu Arg Glu Tyr Asn Lys Leu Lys Glu Arg Leu
        210                 215             220
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

```
His Gln Leu Val Met Asn Lys Lys Asp Lys Lys Ile Ala Met Asp Ile
225             230             235             240

Leu Asn Tyr Val Gly Arg Ala Asp Gly Lys Arg Gly Ser Trp Arg Thr
                245             250             255

Gly Lys Thr Glu Ala Arg Asn Glu Asp Glu Met Tyr Lys Ile Leu Leu
            260             265             270

Asn Asp Tyr Glu Tyr Arg Gln Lys Gln Ile Leu Met Glu Asn Ala Glu
            275             280             285

Leu Lys Lys Val Leu Gln Gln Met Lys Lys Glu Met Ile Ser Leu Leu
            290             295             300

Ser Pro Gln Lys Lys Lys Pro Arg Glu Arg Val Asp Asp Ser Thr Gly
305             310             315             320
```

UNITED STATES PATENT AND TRADEMARK OFFICE
CERTIFICATE OF CORRECTION

PATENT NO.        : 7,364,876 B2
APPLICATION NO.   : 10/644084
DATED             : April 29, 2008
INVENTOR(S)       : Takai et al.

It is certified that error appears in the above-identified patent and that said Letters Patent is hereby corrected as shown below:

```
Thr Val Ile Ser Asp Val Glu Glu Asp Ala Gly Glu Leu Ser Arg Glu
            325                 330                 335

Ser Met Trp Asp Leu Ser Cys Glu Thr Val Arg Glu Gln Leu Thr Asn
            340                 345                 350

Ser Ile Arg Lys Gln Trp Arg Ile Leu Lys Ser His Val Glu Lys Leu
            355                 360                 365

Asp Asn Gln Val Ser Lys Val His Leu Glu Gly Phe Asn Asp Glu Asp
            370                 375                 380

Val Ile Ser Arg Gln Asp His Glu Gln Glu Thr Glu Lys Leu Glu Leu
385                 390                 395                 400

Glu Ile Gln Gln Cys Lys Glu Met Ile Lys Thr Gln Gln Gln Leu Leu
            405                 410                 415

Gln Gln Gln Leu Ala Thr Ala Tyr Asp Asp Thr Thr Ser Leu Leu
            420                 425                 430
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
Arg Asp Cys Tyr Leu Leu Glu Glu Lys Glu Arg Leu Lys Glu Glu Trp
        435             440             445

Ser Leu Phe Lys Glu Gln Lys Lys Asn Phe Glu Arg Glu Arg Arg Ser
        450             455             460

Phe Thr Glu Ala Ala Ile Arg Leu Gly Leu Glu Arg Lys Ala Phe Glu
465             470             475             480

Glu Glu Arg Ala Ser Trp Leu Lys Gln Gln Phe Leu Asn Met Thr Thr
            485             490             495

Phe Asp His Gln Asn Ser Glu Asn Val Lys Leu Phe Ser Ala Phe Ser
            500             505             510

Gly Ser Ser Asp Trp Asp Asn Leu Ile Val His Ser Arg Gln Pro Gln
        515             520             525

Lys Lys Pro His Ser Val Ser Asn Gly Ser Pro Val Cys Met Ser Lys
        530             535             540
```

UNITED STATES PATENT AND TRADEMARK OFFICE
CERTIFICATE OF CORRECTION

PATENT NO.       : 7,364,876 B2
APPLICATION NO.  : 10/644084
DATED            : April 29, 2008
INVENTOR(S)      : Takai et al.

It is certified that error appears in the above-identified patent and that said Letters Patent is hereby corrected as shown below:

```
Leu Thr Lys Ser Leu Pro Ala Ser Pro Ser Thr Ser Asp Phe Cys Gln
545             550             555                     560

Thr Arg Ser Cys Ile Ser Glu His Ser Ser Ile Asn Val Leu Asn Ile
            565             570                     575

Thr Ala Glu Glu Ile Lys Pro Asn Gln Val Gly Gly Glu Cys Thr Asn
        580             585                     590

Gln Lys Trp Ser Val Ala Ser Arg Pro Gly Ser Gln Glu Gly Cys Tyr
        595             600             605

Ser Gly Cys Ser Leu Ser Tyr Thr Asn Ser His Val Glu Lys Asp Asp
        610             615             620

Leu Pro
625
```

UNITED STATES PATENT AND TRADEMARK OFFICE
CERTIFICATE OF CORRECTION

PATENT NO. : 7,364,876 B2
APPLICATION NO. : 10/644084
DATED : April 29, 2008
INVENTOR(S) : Takai et al.

It is certified that error appears in the above-identified patent and that said Letters Patent is hereby corrected as shown below:

In claim 3, at column 53, line 22, please delete "claim 1" and insert therefor --claim 2--.

In claim 4, at column 54, line 17, please delete "supematant" and insert therefor --supernatant--.

Signed and Sealed this

Twenty-fourth Day of February, 2009

JOHN DOLL
*Acting Director of the United States Patent and Trademark Office*